US008030279B2

(12) United States Patent
Joullie

(10) Patent No.: US 8,030,279 B2
(45) Date of Patent: Oct. 4, 2011

(54) TAMANDARIN ANALOGS AND FRAGMENTS THEREOF AND METHODS OF MAKING AND USING

(75) Inventor: Madeleine M. Joullie, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 1258 days.

(21) Appl. No.: 10/550,196

(22) PCT Filed: Mar. 19, 2004

(86) PCT No.: PCT/US2004/008275
§ 371 (c)(1),
(2), (4) Date: Jan. 12, 2007

(87) PCT Pub. No.: WO2004/084812
PCT Pub. Date: Oct. 7, 2004

(65) Prior Publication Data
US 2007/0149446 A1    Jun. 28, 2007

Related U.S. Application Data

(60) Provisional application No. 60/456,967, filed on Mar. 21, 2003.

(51) Int. Cl.
*A61K 38/00* (2006.01)
*A61P 35/00* (2006.01)
(52) U.S. Cl. ...................................... 514/19.3
(58) Field of Classification Search ................ None
See application file for complete search history.

(56) References Cited

U.S. PATENT DOCUMENTS

| | | | |
|---|---|---|---|
| 4,160,452 A * | 7/1979 | Theeuwes | |
| 4,256,108 A * | 3/1981 | Theeuwes | |
| 4,265,874 A * | 5/1981 | Bonsen et al. | |
| 4,493,796 A | 1/1985 | Rinehart, Jr. | |
| 4,782,135 A | 11/1988 | Rinehart, Jr. | |
| 5,137,870 A | 8/1992 | Rinehart | |
| 5,504,189 A | 4/1996 | Emling et al. | |
| 6,509,315 B1 * | 1/2003 | Joullié et al. | |
| 7,064,105 B2 | 6/2006 | Joullié et al. | |
| 7,122,519 B2 | 10/2006 | Joullié et al. | |
| 7,651,997 B2 * | 1/2010 | Joullié et al. | |
| 7,678,265 B2 * | 3/2010 | Fabrell | |
| 7,737,114 B2 * | 6/2010 | Joullie et al. | 514/21.1 |
| 2003/0104991 A1 | 6/2003 | Joullie et al. | |
| 2007/0129289 A1 | 6/2007 | Joullie et al. | |

FOREIGN PATENT DOCUMENTS

| | | |
|---|---|---|
| ES | 2 102 322 A1 | 7/1997 |
| WO | WO 98/17275 A1 | 4/1998 |
| WO | WO 98/17302 A1 | 4/1998 |
| WO | WO 01/76616 A1 * | 10/2001 |
| WO | WO 02/02596 A2 | 1/2002 |

OTHER PUBLICATIONS

Liang et al. Total Synthesis of [(2S)-Hiv2]Didemnin M. J Org Chem, 2000, vol. 65, pp. 4762-4765.*
Bren. Fluorescent and photochromic chemosensors. Russian Chemical Reviews. 2001. vol. 70, No. 12, pp. 1017-1036.*
Bundgaard, H., *Design of Prodrugs* pp. 7-9, 21-24, Elsevier Science Publishers B.V., The Netherlands (1985).
Depenbrock, et al., "In vitro activity of aplidine, a new marine-derived anti-cancer compound, on freshly explanted clonogenic human tumour cells and haematopoietic precursor cells," *Brit. J. Cancer* 78:739-744, Cancer Research Campaign, UK (1998).
Grubb, et al., "Didemnin B induces cell death by apoptosis: the fastest induction of apoptosis ever described," *Biochem. Biophys. Res. Commun.* 215:1130-1136, Academic Press, Inc., United States (1995).
Johnson, et al., "Protein tyrosine kinase inhibitors prevent didemnin B-induced apoptosis in HL-60 cells," *FEBS Lett.* 383:1-5, Federation of European Biochemical Societies, UK (1996).
Johnson, et al., "Rapamycin inhibits didemnin B-induced apoptosis in human HL-60 cells: Evidence for the possible involvement of FK506-binding protein 25," *Immunol. Cell Biol.* 77:242-248, Nature Publishing Group, United States (1999).
Johnson, et al., "Unspecific Activation of Caspases During the Induction of Aapoptosis by Didemnin B in Human Cell Lines," *J. Cell. Biochem.* 72:269-278, Wiley-Liss, Inc., United States (1999).
Li, at al., "Total Synthesis and Structural Investigations of Didemnins A, B, and C," *J. Am. Chem. Soc.* 112:7659-7672, American Chemical Society, United States (1990).
Liang, et al., "The First Total Synthesis of (−)—Tamandarin A," *Org. Lett.* 1:1319-1322, American Chemical Society, United States (1999).
Liang, et al., "Total Synthesis of [(2S)-Hiv$^2$]Didemnin M," *J. Org. Chem.* 65:4762-4765, American Chemical Society, United States (2000).
Liang, at al., "Total Syntheses and Biological Investigations of Tamandarins A and B and Tamandarin A Analogs," *J. Am. Chem. Soc.* 123:4469-4474, American Chemical Society, United States (2001).
MacLean, et al., "Glossary of Terms Used in Combinatorial Chemistry," *Pure Appl. Chem.* 71:2349-2365, IUPAC, United States (1999).
Petit & Larcheveque, "Ethyl Glycidate from (S)-Serine; Ethyl (R)-(+)-2,3-Epoxypropanoate (Oxiranecarboxylic acid, ethyl ester, (R)-)," *Organic Syntheses* vol. 75, pp. 37-44, ed. Amos B. Smith, III, John Wiley & Sons, Inc, United States (1998).
Pfizenmayer, et al., "Synthesis and Biological Activity of [Tic$^5$] Didemnin B," *Bioorg. Med. Chem. Lett.* 8:3653-3656, Elsevier Science Ltd., UK (1998).
Sakai, at al., "Structure-Activity Relationships of the Didemnins[1,2]," *J. Med. Chem.* 39:2819-2834, American Chemical Society, United States (1996).

(Continued)

*Primary Examiner* — Marcela M Cordero Garcia
(74) *Attorney, Agent, or Firm* — Sterne, Kessler, Goldstein & Fox P.L.L.C.

(57) ABSTRACT

The present invention is directed to a compound of Formula I wherein $R^1$, $R^2$, $R^3$, $R^4$, $R^5$, $R^6$, W, X, Y, and Z are defined herein. The compounds of the present invention are useful as anticancer agents. Specifically, the compounds are useful for treating or preventing cancer and tumor growth. The present invention is also directed to compositions comprising a compound according to the above formula. The present invention is also directed to methods of using a compound according to the above formula.

34 Claims, 1 Drawing Sheet

OTHER PUBLICATIONS

Skehan, et al., "New Colorimetric Cytotoxicity Assay for Anticancer-Drug Screening," *J. Natl. Cancer Inst.* 82:1107-1112, Oxford University Press, United States (1990).

International Search Report for International Application No. PCT/US04/08275, United States Patent and Trademark Office, United States, mailed on Aug. 9, 2005, published Oct. 6, 2005.

Nakamura, et al., "Dehydrooligopeptides. XVII. Practical Synthesis of All of the Diastereomers of N,N-Protected 2,3-Diaminobutanoic Acids from L- and D-Threonine Derivatives," *Bull. Chem. Soc. Jpn* 68:1369-1377, The Chemical Society of Japan, Japan (1995).

Sifferlen, T., at al., " β-Thiopeptides: Synthesis, NMR Solution Structure, CD Spectra and Photochemistry," *Helv. Chim. Acta* 82:2067-2093, Neue Schweizerische Chemische Gesellschaft, Switzerland (1999).

Shalaby, M.A, et al., "Thiopeptide Synthesis. α-Amino Thionoacid Derivatives of Nitrobenzotriazole as Thioacylating Agents," *J. Org. Chem.* 61:9045-9048, American Chemical Society, United States (1996).

Sakai, R., et al., "Seven New Didemnins from the Marine Tunicate *Trididemnum solidum*," *J. Am. Chem. Soc.* 117:3734-3748, American Chemical Society, United States (1995).

Hossain, M. B, et al., "Crystal and molecular structure of didemnin B, an antiviral and cytotoxic depsipeptide," *Proc. Natl. Acad. Sci. USA* 85:4118-4122, National Academy of Sciences, United States (1988).

Roush, W.R., et al., "Design, Synthesis and Evaluation of D-Homophenylalanyl Epoxysuccinate Inhibitors of the Trypanosomal Cysteine Protease Cruzain," *Tetrahedron* 56:9747-9762, Elsevier Science Ltd., UK (2000).

Armstrong, R.N., "Nucleophilic Epoxide Openings," *Comprehensive Natural Products Chemistry vol. 5*, pp. 51-70, ed. C. Dale Poulter, Elsevier Science, Ltd., UK (1999).

Wróblewski, A.E. & Balcerzak, K.B., "Synthesis of diethyl (1R,2R)- and (1S,2R)-3- acetamido-1,2-dihydroxypropylphosphonates," *Tetrahedron: Asymmetry* 13:845-850, Elsevier Science Ltd., UK (2002).

Lindberg, J., et al., "Efficient Synthesis of Phospholipids from Glycidyl Phosphates," *J. Org. Chem.* 67:194-199, American Chemical Society, United States (2002).

Sata, N.U., et al., "Synthesis of all isomers of pulcherrimine, a bitter principle in the sea urchin ovary," *Tetrahedron Letters* 43:115-118, Elsevier Science Ltd., UK (2002).

Kwon, S. J. & Ko, S.Y., "Synthesis of statine employing a general *syn*-amino alcohol building block," *Tetrahedron Letters.* 43:639-641, Elsevier Science Ltd., UK (2002).

Koviach, J. L., et al., "Design and Synthesis of Conformationally Constrained Glycosylated Amino Acids," *J. Org. Chem.* 66:2318-2326, American Chemical Society, United States (2001).

Gravier-Pelletier, C., et al., "Liposidomycins—Synthetic Studies Towards the Ribosyldiazepanone Moiety," *Eur. J. Org. Chem.* 16:3089-3096, Wiley-VCH Verlag GmbH, Germany (2001).

Bardi, R., et al., "Molecular and Crystal Structures of Three Monothiated Analogues of the Terminally Blocked Ala-Aib-Ala Sequence of Peptaibol Antiobiotics," *Bipolymers* 27:747-761, John Wiley & Sons, Inc., United States (1988).

Meyer, J.-P., et al., "Synthesis Using a Fmoc-Based Strategy and Biological Activites of Some Reduced Peptide Bond Pseudopeptide Analogues of Dynorphin A[1]," *J. Med. Chem.* 38:3462-3468, American Chemical Society, United States (1995).

Tran, T. T., et al., "Effects of Thioamide Substitutions on the Conformation and Stability of α-and $3_{10}$-Helices," *J. Am. Chem. Soc.* 124:5222-5230, American Chemical Society, United States (2002).

Gauthier, J.Y & Lebel, H., "A remarkably simple conversion of nitriles to thioamides," *Phosphurus, Sulfur, and Silicon* 95-96:325-326, OPA Amsterdam B.V., Holland (1994).

Davidsen, S.K., et al., "Di-*tert*-butyl N-Acylimidodicarbonates as Isolable Acylating Agents: Mild Conversion of Primary Carboxamides to Substituted Amides," *J. Org. Chem.* 56:5482-5485, American Chemical Society, United States (1991).

Pozdnev, V.F., "Activation of carboxylic acids by pyrocarbonates. Application of di-tert-butyl pyrocarbonate as condensing reagent in the synthesis of amides of protected amino acids and peptides," *Tetrahedron Letters* 36:7115-7118, Elsevier Science Ltd., UK (1995).

Rinehart, Jr., K. L., et al., "Didemnins: Antiviral and Antitumor Depsipeptides from a Carriban Tunicate," *Science* 212:933-935, AAAS, United States (1981).

Supplementary Partial European Search Report, Application No. EP 01924886.3, Jul. 12, 2004.

Abou-Mansour, E., et al., "[Tyr[5]]didemnin B and [D-Pro[4]]didemnin B ; Two New Natural Didemnins with a Modified Macrocycle," *Tetrahedron* 51:12591-12600, Elsevier Science Ltd., UK (1995).

Rose, N.G.W., et al., "Synthesis of enantiomerically enriched β,γ-unsaturated-α-amino acids," *Tetrahedron* 57:1497-1507, Elsevier Science Ltd., UK (2001).

Blaskovich, M. A., et al., "Stereoselective Synthesis of *Threo* and *Erythro* β-Hydroxy and β-Hydroxy and β-Disubstituted-βHydroxy α-Amino Acids," *J. Org. Chem.* 63:3631-3646, American Chemical Society, United States (1998).

Spero, D.M. & Kapadia, S.R., "Enantioselective Synthesis of α,α-Disubstituted Amino Acid Derivatives *via* Enzymatic Resolution: Preparation of a Thiazolyl-Substituted α-Methyl α-Benzyl Amine," *J. Org. Chem.* 61:7398-7401, American Chemical Society, United States (1996).

Adrio, J., et al., "Total Synthesis and Biological Evaluation of Tamandarin B Analogues," *J. Org. Chem.* 72:5129-5138, American Chemical Society, United States (2007).

Pfizenmayer, A.J., et al., "Synthesis and Biological Activities of [N-MeLeu[5]]- and [N-MePhe[5]]-Didemnin B," *Tetrahedron* 55:313-334, Elsevier Science Ltd., UK (1999).

Schmidt, U., et al., "Synthesis and cytostatic activities of didemnin derivatives*," *Journal of Peptide Research* 54:146-161, Munksgaard International Publishers Ltd, Denmark (1999).

Grieco, P.A. & Bahsas, A., "Immonium Ion Based Synthetic Methodology: A Novel Method for the N-Methylation of Dipeptides and Aminco Acid Derivatives via Retro Aza Diels-Alder Reactions," *J. Org. Chem.* 52:5746-5749, American Chemical Society, United States (1987).

Wipf, P & Venkatraman, S., "Total Synthesis of (−)—Muscoride A," *J. Org. Chem.* 61:6517-6522, American Chemical Society, United States (1996).

Kim, H.-O., et al., "Copper(I)-Promoted Condensation of α-Amino Acids with β-Keto Thio Esters: Synthesis of N-Acylated L-Leucine Derivatives Containing (S)-4-Hydroxy-5-methyl- and (S)-4-Hydroxy-2,5-dimethyl-3-oxohexanoic Acid," *J. Org. Chem.* 52:4531-4536, American Chemical Society, United States (1987).

Abdel-Magid, A.F., et al., "Reductive Amination of Aldehydes and Ketones by Using Sodium Tricetoxyborohydride," *Tetrahedron Lett.* 31:5595-5598, Pergamon Press plc, UK (1990).

Abdel-Magid, A.F. & Maryanoff, C.A. "Reductive Amination of Aldehydes and Ketones with Weakly Basic Anilines Using Sodium Triacetoxyborohydride," *Synlett.* 537-539, Germany (1990).

Ahuja, D., et al., "Inhibition of Protein Synthesis by Didemnin B: How EF-1α Mediates Inhibition of Translocation," *Biochemistry* 39:4339-4346, American Chemical Society, United States (2000).

Ahuja, D., et al., "Inhibition of Protein Synthesis by Didemnins: Cell Potency and SAR," *J. Med. Chem.* 43:4212-4218, American Chemical Society, United States (2000).

Campbell, M.J., et al., "Growth inhibition of DU-145 prostate cancer cells by a *Bcl-2* antisense oligonucelotide is enhanced by *N*-(2-hydroxyphenyl.)all-*trans* retinamide." *Brit. J. of Cancer* 77:739-744, Cancer Research Campaign, UK (1998).

Crews, C.M., et al., "Didemnin binds to the protein palmitoyl thioesterase responsible for infantile neuronal ceroid lipofuscinosis," *Proc. Natl. Acad. Sci. USA* 93:4316-4319, Natl. Acad. Sci., United States (1996).

Ding, X., et al., "Structure-Activity Relationships of Side-Chain Modified Didemnins," *Bioorg. Med. Chem. Lett.* 11:231-234, Elsevier Science Ltd., United States (2001).

Ewing, W.R., et al., "Synthetic Studies of Didemnins. 1. Revision of the Stereochemistry of the Hydroxyisovalerylpropionyl (HIP) Unit.," *Tetrahedron* 42:5863-5868, Pergamon Journals Ltd., UK (1986).

Ewing, W.R., et al., "Synthetic Studies of Didemnind. IV. Synthesis of the Macrocycle," *Tetrahedron Lett.* 30:3757-3760, Maxwell Pergamon Macmillan plc, UK (1989).

Harris, B.D., et al., "Synthetic Studies of Didemnins. II. Approaches to Statine Diastereomers," *Tetrahedro Lett. 28*:2837-2840, Pergamon Journals Ltd., UK (1987).

Harris, B.D., et al., "Synthetic Studies of Didemnins. III: Synthesis of Statine and Isostatine Stereoisomers," *Tetrahedron 44*:3489-3500, Pergamon Press plc, UK (1988).

Jou, G., et al., "Total Synthesis of Dehydrodidemnin B. Use of Uronium and Phosphonium Salt Coupling Reagents in Peptide Synthesis in Solution," *J. Org. Chem. 62*:354-366, American Chemical Society, United States (1997).

Joullié, M.M., et al., "Total Synthesis of (−)—tamandarin B," *Tetrahedron Lett. 41*:9373-9376, Elsevier Science Ltd., UK (2000).

Joullié, M.M., et al., "Chemical Defense in Ascidians of the *Didemnidae* Family," *Biconjugate Chem. 14*:30-37, American Chemical Society, United States (2003).

Li, W.-R. & Joullié, M.M., "The Didemnins: Biological Properties, Chemistry and Total Synthesis," *Studies in Natural Products Chemistry*, 10:241-302, Elsevier Science publishers B.V., The Netherlands (1992).

Mayer, S.C., et al., "Synthesis of New Didemnin B Analogs for Investigations of Structure/Biological Activity Relationships," *J. Org. Chem.*, 59:5192-5205, American Chemical Society, United States (1994).

Mayer, S.C., et al., "Synthetic Routes to a Constrained Ring Analog of Didemnin B," *J. Org. Chem. 61*:1655-1664, American Chemical Society, United States (1996).

Mayer, S.C., et al., "Synthetic Studies of a Constrained Ring Didemnin Analog," *Tetrahedron: Asymmetry 5*:519-522, Elsevier Science Ltd., UK (1994).

Mayer, S.C., et al., "The Cyclic Depsipeptide Backbone of the Didemnins," *Acta. Cryst. C51*:1609-1614, International Union of Crystallography, UK (1995).

Pfizenmayerm A.J., et al., "Synthesis and Biological Activities of [$N$-MeLeu$^5$] Didemnin B," *Biog. Med. Chem. Lett. 6*:2713-2716, Elsevier Science Ltd., UK (1996).

Portonova, P., et al., "First Total Synthesis of a Fluorescent Didemnin," *Tetrahedron 56*:3687-3690, Elsevier Science Ltd., UK (2000).

Ramanjulu, J.M., et al., "A Facile Synthesis of Benzyl 2-Amino-3-Azido-4-*O*-p-Methoxybenzyl-6-*O*-Benzyl-2,3-dideoxy-α-D-FGlucopyranoside: A Key Intermediate in the Formation of a Didemnin B Analog," *J. Carbohydrate Chemistry 15*:371-381, Marcel Dekker, Inc., United States (1996).

Ramanjulu, J.M., et al., "Analogs of the β-Turn of the Cyclodepsipeptide Didemnin B," *Tetrahedron Letters 37*:311-314, Elsevier Science Ltd., UK (1996).

Ramanjulu, J.M., et al., "Synthesis of Acyclic Analogs of Didemnin B," *Synthetic Communications 27*:3259-3272, Marcel Dekker, Inc., United States (1997).

Ramanjulu, J.M., et al., "Synthesis of a Reduced Ring Analog of Didemnin B," *J. Org. Chem. 62*:4961-4969, American Chemical Society, United States (1997).

Ramanjulu, J.M., et al., "Synthesis Studies of a Didemnin B Analog Based on a 2,3-Diamino Sugar Scaffolding," *J. Chin. Chem. Soc. 48*:1-4, The Chemical Society, Taiwan (2001).

Schumaher, K.K., et al., "Synthetic studies toward astins A, B and C. Efficient syntheses of *cis*-3,4-dihydroxyprolines and (−)—(3$S$,4$R$)-dichloroproline esters." *Tetrahedron: Asymmetry 9*:47-53, Elsevier Science Ltd., UK (1998).

Tarver Jr., J.E., et al., "Total Syntheses of Conformationally Constrained Didemnin B Analogues. Replacements of $N,O$-Dimethyltyrosine with L-1,2,3,4-Tetrahydroisoquinoline and L-1,2,3,4-Tetrahydro-7-methoxyisoquinoline," *J. Org. Chem. 66*:7575-7587, American Chemical Society, United States (2001).

Vera, M.D., et al., "[Lys$^3$] Didemnins as Potential Affinity Ligands," *Biorg. Med. Chem. Lett. 11*:13-16, Elsevier Science Ltd., UK (2001).

Vera, M.D. & Joullié, M.M., "Natural Products as Probes of Cell Biology: 20 Years of Didemnin Research," *Medicinal Research Reviews 22*:102-145, John Wiley & Sons, Inc., United States (2002).

Vera, M.D., et al., "Synthesis and Biological Evaluation of Didemnin Photoaffinity Analogues," *Biorg. Med. Chem. Lett. 11*:1871-1874, Elsevier Science Ltd., UK (2001).

Vervoort, H. & Fenical, W., "Tamandarins A and B: New Cytotoxic Depsipeptides from a Brazilian Ascidian of the Family Didemnidae," *J. Org. Chem. 65*:782-792, American Chemical Society, United States (2000).

Wipf, P., "Synthetic Studies of Biologically Active Marine Cyclopeptides," *Chem. Rev. 95*:2115-2134, American Chemical Society, United States (1995).

Xiao, D., et al., "Total Synthesis of a Conformationally Constrained Didemnin B," *J. Org. Chem. 66*:2734-2742, American Chemical Society, United States (2001).

STNEasy/CAplus English Language Abstract of Spanish Patent Publications No. ES 2 102 322 A1 (1997), document FP1, Accession No. 1998:169709.

\* cited by examiner

TAMANDARIN ANALOGS AND FRAGMENTS THEREOF AND METHODS OF MAKING AND USING

The present application is a National Phase of PCT/US2004/008275, with an international filing date of Mar. 19, 2004, which claims the benefit under 35 U.S.C. §119(e) of Provisional Application No. 60/456,967, filed Mar. 21, 2003, now abandoned.

BACKGROUND OF THE INVENTION

1. Field of the Invention

The present invention relates to macrocyclic depsipeptides, including didemnin and tamandarin analogs and fragments thereof, which are useful as anti-cancer agents and for other purposes. Methods of using these compounds as inhibitors of protein synthesis, cell growth, tumorigenesis, and viral infection, and for immunosuppresive therapy, and as enhancers of apoptosis are also provided. Methods of making the tamandarin analogs are also provided.

2. Background Art

Tamandarins A and B are naturally occurring didemnin analogs which have been isolated from a marine tunicate. Tamandarins A and B belong to a family of compounds (didemnins—from organisms of the Didemnidae family) which potently inhibit protein synthesis and cell cycle progression and induce rapid apoptosis (Grubb et al., *Biochem. Biophys, Res. Commun.* 215:1130-1136 (1995); Johnson et al., *FEBS Lett.* 383:1-5 (1996); Johnson et al., *Immunol. Cell Biol.* 77:242-248 (1999); Johnson et al., *J. Cell. Biochem.* 72:269-278 (1999)). Other didemnins, including didemnin B, didemnin M, and dehydrodidemnin B, exhibit cytotoxic and cytostatic effects as well.

Tamandarins A and B exhibit biological activity which is similar to the activities exhibited by didemnin B. See, e.g., Liang, et al., *J. Am. Chem. Soc.* 123:4469-4474 (2001). For example, tamandarin A is a potent inhibitor of protein synthesis, cell growth, and tumorigenesis. Tamandarin A exhibits significant in vitro activity against pancreatic carcinoma (Liang et al., *Org. Lett.* 1: 1319-1322 (1999)).

A significant limitation on the use of the tamandarins and didemnins, either for research or for other applications, is the limited supply of tamandarins that is available from natural sources and the difficulty and expense of isolating these compounds. A need exists for a method of synthesizing tamandarins A and B and other didemnin analogs.

Furthermore, very few derivatives or analogs of tamandarins A and B have been prepared and examined. Additional derivatives and analogs of tamandarins A and B and didemnins are needed. Additionally, compound which are useful in the synthesis of tamandarins and didemnins are needed. Additional compounds that are useful as inhibitors of protein synthesis, cell growth, tumorigenesis, and viral infection, and for immunosuppresive therapy, and/or as enhancers of apoptosis are also needed.

SUMMARY OF THE INVENTION

A first aspect of the present invention is directed to a compound of Formula I, IA, or II.

A second aspect of the present invention is directed to a composition, for example a pharmaceutical composition, comprising a compound of Formula I, IA, or II and a suitable carrier or excipient.

A third aspect of the present invention is directed to a method of inhibiting or preventing the growth of a cancer cell or tumor, said method comprising contacting a cancer cell with an effective amount of a compound of Formula I, IA, or II. In one embodiment, the method is directed to treating or preventing cancer in a subject in need of such treatment, comprising administering to said subject an effective amount of Formula I, IA, or II.

A fourth aspect of the present invention is directed to a method of inhibiting or preventing tumorigenesis, said method comprising contacting a cell or cellular component with an effective amount of a compound of Formula I, IA, or II. In one embodiment, the method is directed to inhibiting or preventing tumorigenesis in a subject in need of such treatment, comprising administering to said subject an effective amount of Formula I, IA, or II.

A fifth aspect of the present invention is directed to a method of inhibiting or preventing protein synthesis, said method comprising contacting a cell or cellular component with an effective amount of a compound of Formula I, IA, or II. In one embodiment, the method is directed to inhibiting or preventing protein synthesis in a subject in need of such treatment, comprising administering to said subject an effective amount of Formula I, IA, or II.

A sixth aspect of the present invention is directed to a method of enhancing apoptosis, said method comprising contacting a cell or cellular component with an effective amount of a compound of Formula I, IA, or II. In one embodiment, the method is directed to enhancing apoptosis in a subject in need of such treatment, comprising administering to said subject an effective amount of Formula I, IA, or II.

A seventh aspect of the present invention is directed to a method of providing immunosuppresive therapy, said method comprising contacting a cell or cellular component with an effective amount of a compound of Formula I, IA, or II. In one embodiment, the method is direct to providing immunosuppresive therapy to a subject in need of such treatment, comprising administering to said subject an effective amount of Formula I, IA, or II.

A eighth aspect of the present invention is directed to the use of a compound according to Formula I, IA, or II in the preparation of a pharmaceutical composition useful for inhibiting or preventing the growth of a cancer cell or tumor.

A ninth aspect of the present invention is directed to a method of preventing or treating a viral infection, said method comprising administering to a subject in need of such treatment an effective amount of a compound of Formula I, IA, or II.

A tenth aspect of the present invention is directed to the use of a compound according to Formula I, IA, or II in the preparation of a pharmaceutical composition useful for one or more of the methods described herein.

An eleventh aspect of the present invention is directed to a method of preparing a compound according to Formula I, IA, or II.

DETAILED DESCRIPTION OF THE INVENTION

Figure 1:
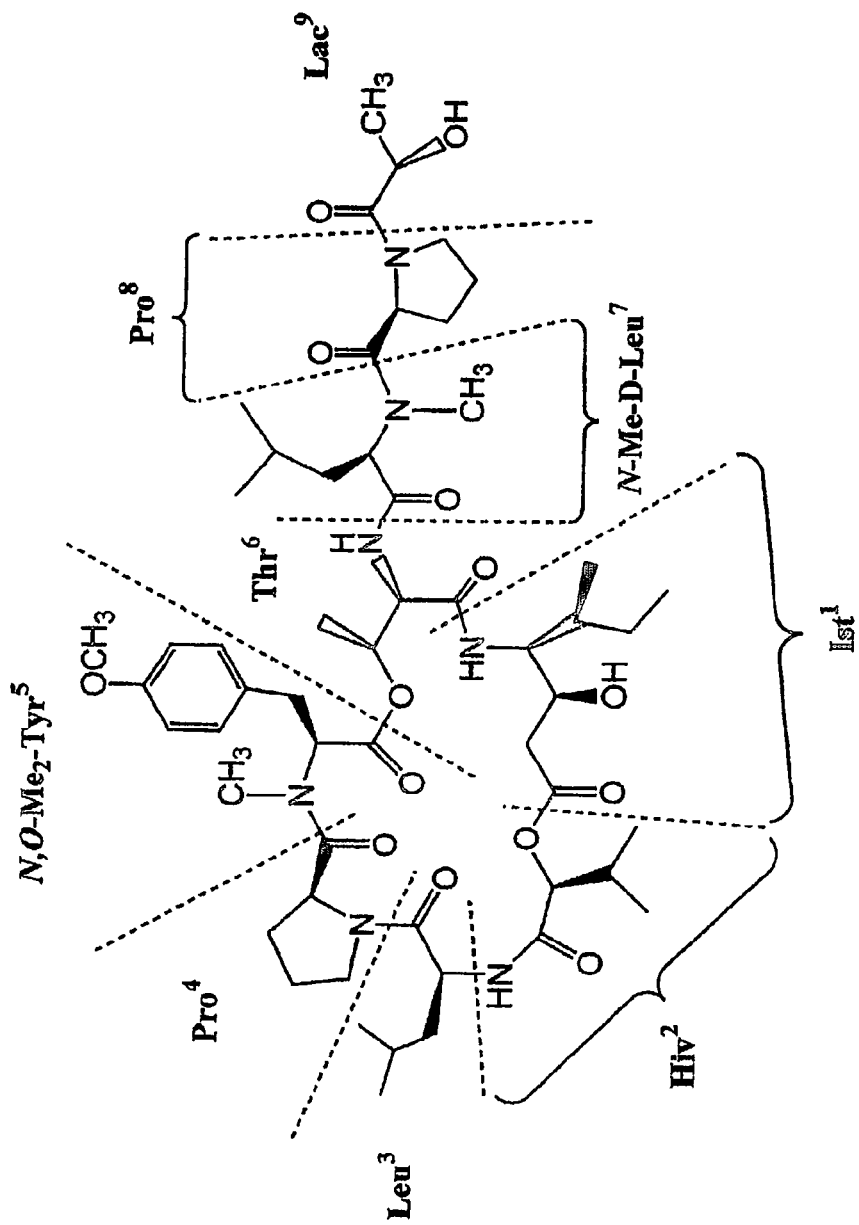
FIG. 1 is the structure of Tamandarin A illustrating the numbering convention used herein and in Sakai et al., *J. Med. Chem.* 39:2819-2834 (1996).

A first aspect of the present invention is directed to a compound of Formula I:

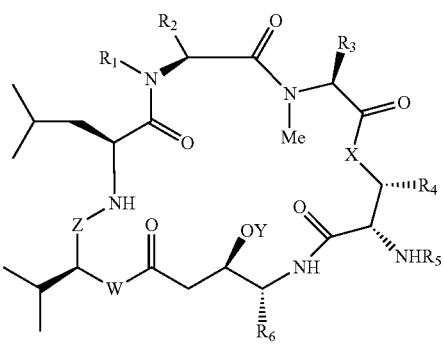

wherein

R$^1$ and R$^2$ are independently H or C$_{1-4}$ alkyl, or R$^1$ and R$^2$ together form the alkyl ring of a proline or homoproline residue;

R$^3$ is selected from the group consisting of a side chain of an amino acid, a naphthylmethyl group, and a first fluorophore;

R$^4$ is H or CH$_3$;

R$^5$ is H, an amine protecting group, an amino acid residue, a polypeptide, a peptide which contains a second fluorophore, a chemical moiety bound to a solid support, or a moiety containing from about 1 to about 50 non-hydrogen atoms;

R$^6$ is an isoleucine side chain or a valine side chain;

W is O or NH;

X is O or NH;

Y is H or a hydroxyl protecting group; and

Z is C(O) or C(O)—CH(CH$_3$)—C(O);

provided that if R$^1$ and R$^2$ together form the alkyl ring of a proline residue, R$^4$ is methyl, W is O, X is O, and Z is C(O), then R$^3$ is not an isoleucine side chain, a valine side chain, an alanine side chain, a norleucine side chain, a norvaline side chain, leucine side chain, a histidine side chain, a tryptophan side chain, an arginine side chain, a lysine side chain, a second fluorophore, or a benzyl optionally substituted with OH, —OCH$_3$, —CO(C$_6$H$_5$), —Br, —I, —F, —Cl, —CH$_3$, and —C$_2$H$_5$; or alternatively provided that provided that if R$^1$ and R$^2$ together form the alkyl ring of a proline residue, R$^4$ is methyl, and X is O, then R$^3$ is naphthylmethyl.

In one embodiment, R$^1$ and R$^2$ are H. In another embodiment, R$^1$ and R$^2$ are C$_{1-4}$ alkyl, for example methyl. In another embodiment, R$^1$ is H and R$^2$ is methyl. In another embodiment, R$^1$ is methyl and R$^2$ is H. In a further embodiment, R$^1$ and R$^2$ together form the alkyl ring of a proline residue. That is, in one embodiment, R$^1$ and R$^2$ together form a 1,3-propanediyl group.

In one embodiment, R$^3$ is side chain of an amino acid, in particular a naturally occurring amino acid. In one embodiment, R$^3$ is amino acid side chain such as an isoleucine side chain, i.e., a 2-butyl moiety, preferably having (R) stereochemistry, a valine side chain, i.e., a 2-propyl moiety, an alanine side chain, i.e., a methyl moiety, a norleucine side chain, i.e., a 1-butyl moiety, a norvaline side chain, i.e., a 1-propyl moiety, a leucine side chain, i.e., an isobutyl moiety, preferably having (S) stereochemistry, a phenylalanine side chain, i.e., a benzyl moiety, a histidine side chain, i.e., a 4-imidazolylmethyl moiety, a tryptophan side chain, i.e., a 3-indolylmethyl moiety, a tyrosine side chain, i.e., a 4-hydroxybenzyl moiety, an arginine side chain, i.e., a 4-guanidinylbutyl moiety, and a lysine side chain, i.e., a 4-aminobutyl moiety.

In another embodiment, R$^3$ is a side chain of a non-naturally occurring amino acid. Non-naturally occurring amino acids are known in the art. In one embodiment, R$^3$ is a naphthylmethyl group. Alternatively, R$^3$ is a benzyl group substituted with OH, C$_{1-4}$ alkoxy such as OCH$_3$ and OCH$_2$CH$_3$, CO(C$_6$H$_5$), F, Cl, Br, I, or C$_{1-4}$ alkyl such as CH$_3$ and CH$_2$CH$_3$.

In another embodiment, R$^3$ is a first fluorophore. Moieties which are fluorophores are known in the art. In one embodiment, the fluorophore is an amino acid side chain as described above further containing a fluorophore moiety (e.g., a fluorophore linked with one of the amino acid side chains described above). Such a fluorophore includes

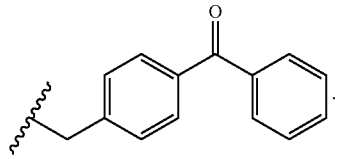

In one embodiment, R$^5$ is H, an amine protecting group, an amino acid residue, a polypeptide, or a peptide which contains a second fluorophore.

In one embodiment, the invention comprises a compound of Formula I wherein R$^5$ is a hydrogen atom or an amine protecting group suitable for protection of amino acids. Such protecting groups are known in the art and referred to throughout this disclosure. A suitable protecting group for R$^5$ includes, for example, tert-butoxycarbonyl. Examples of suitable protecting groups can be found in references such as Green and Wuts (1991, Protective Groups in Organic Synthesis, Wiley, New York, 2$^{nd}$ Edition) and Bodansky (1993, Principles of Peptide Synthesis, Springer, Berlin).

In one embodiment, R$^5$ is an amino acid residue, e.g., a leucine residue, or a polypeptide comprising two or more amino acid residues. In certain embodiments, the R$^5$ group contains 1-10 amino acid residues. In another embodiment, the R$^5$ group contains 1, 2, 3, 4, or 5 amino acid residues. In certain instances, the amino acid residue or polypeptide contains one or more suitable protecting groups. Examples of such amino acid residues and polypeptides include:

—(N-methyl)leucine;
—(N-methyl)leucine-proline;
—(N-CBz-N-methyl)leucine;
—(N-methyl)leucine-proline-lactate;
—(N-methyl)leucine-proline-pyruvate;
—(N-methyl)leucine-proline-lactate-glutamine-pyroglutamate;
—(N-methyl)leucine-proline-lactate-glutamine-cyclopentanoate;
—(N-methyl)leucine-proline-lactate-leucine-pyroglutamate;
—(N-methyl)leucine-proline-lactate-glutamine-cyclopentanoate;
—(N-methyl)leucine-proline-alanine-leucine-pyroglutamate; and
—(N-methyl)leucine-proline-(N-methyl)alanine-leucine-pyroglutamate.

In another embodiment, R$^5$ contains an N-glycidyl-L-proline residue.

A suitable value of R$^5$ is —(N-methyl-R-leucine)-S-proline-glycidate.

Other suitable R$^5$ groups include those having the structure shown below.

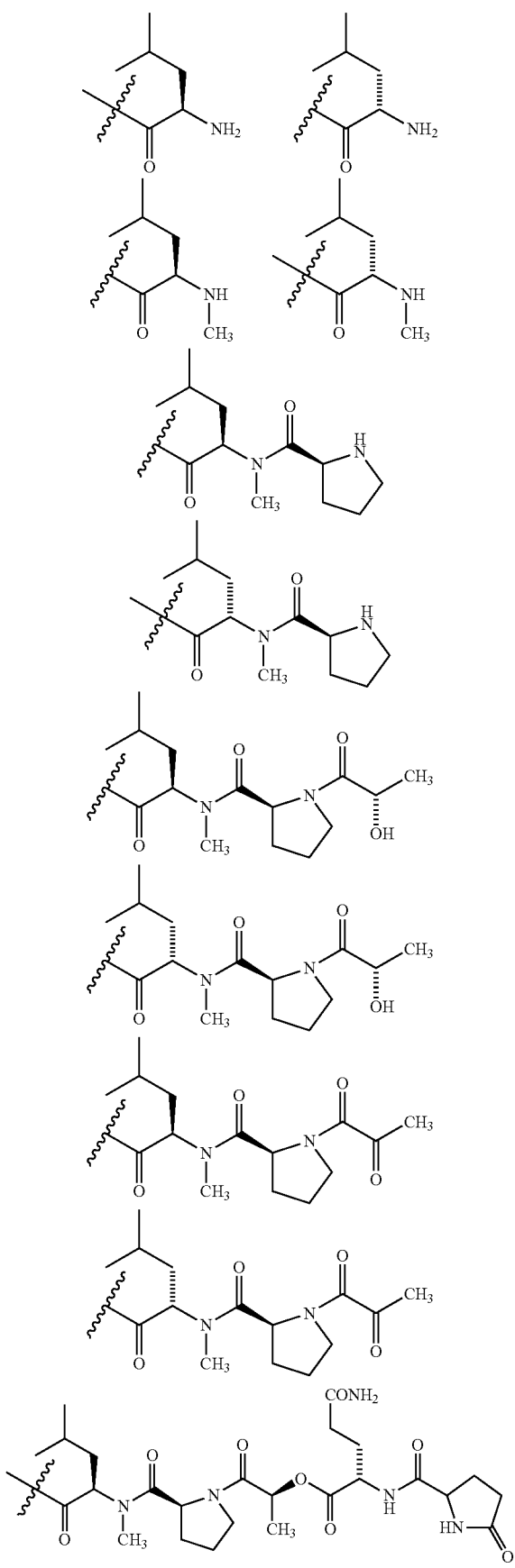
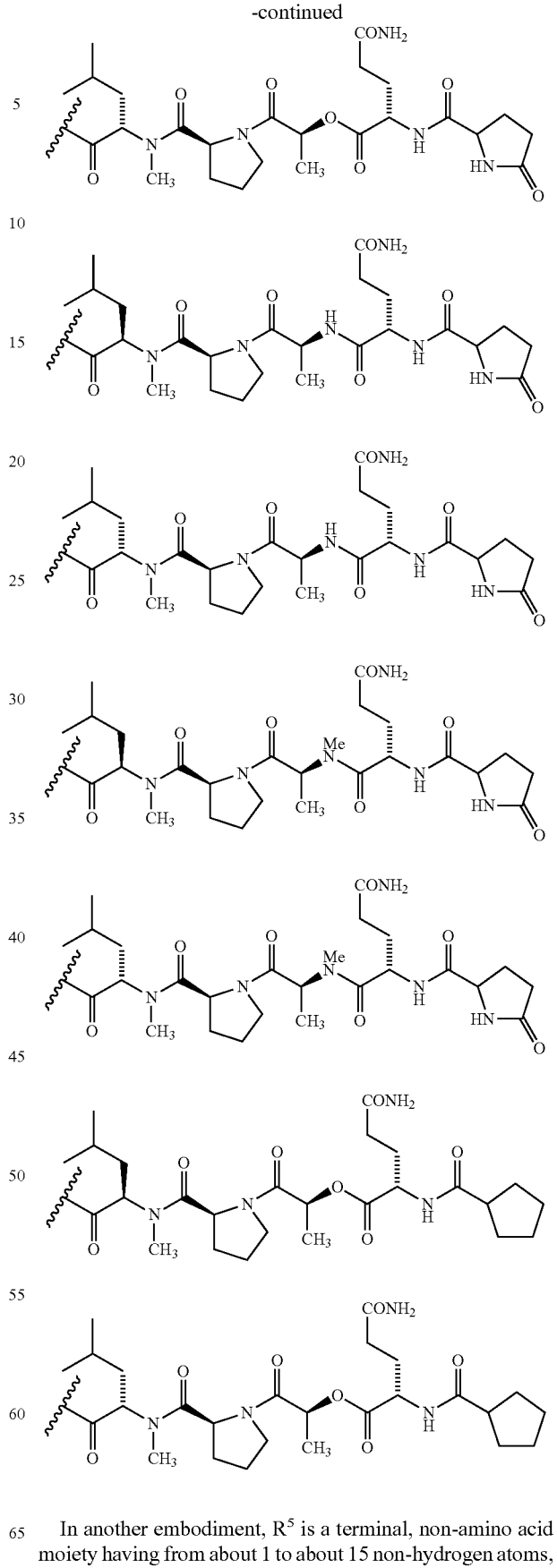
In another embodiment, $R^5$ is a terminal, non-amino acid moiety having from about 1 to about 15 non-hydrogen atoms, e.g., carbon, oxygen, nitrogen, sulfur, halogens, and combi nations thereof. Exemplary groups include those having the following structure:
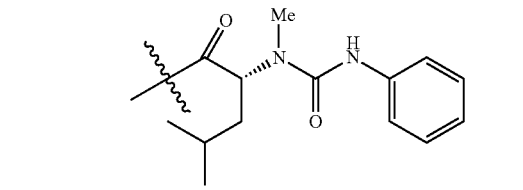
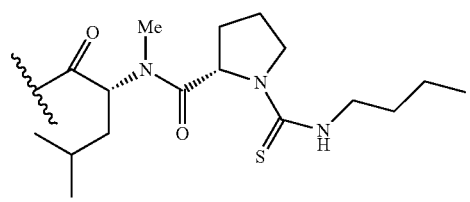
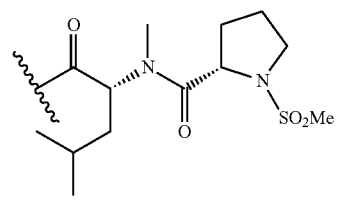
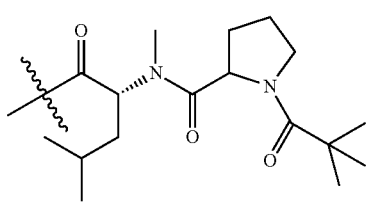
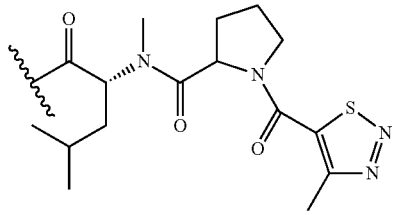
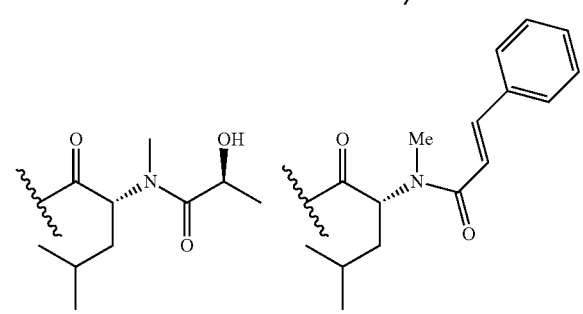
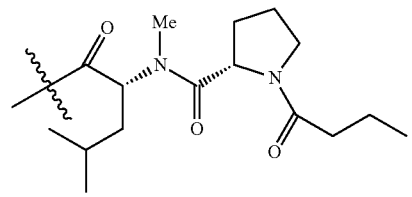
-continued
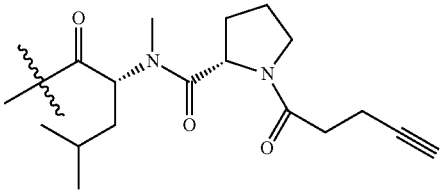
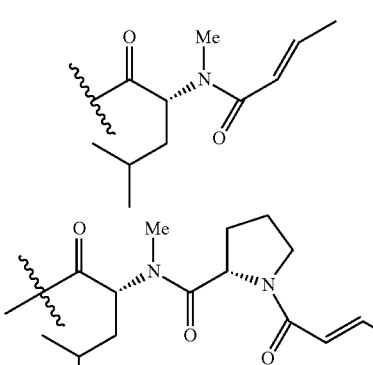
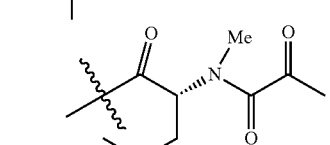
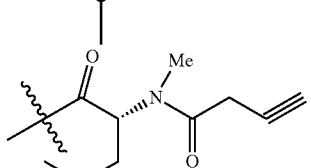
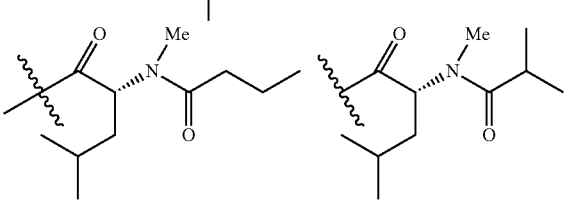
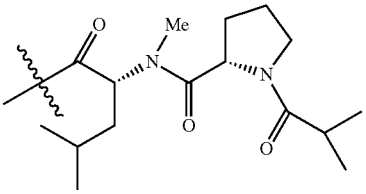
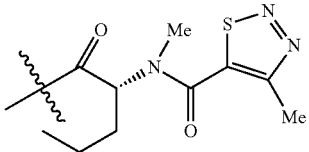
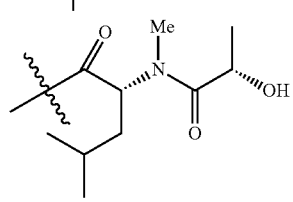

Other suitable R⁵ groups include those having the following structure:

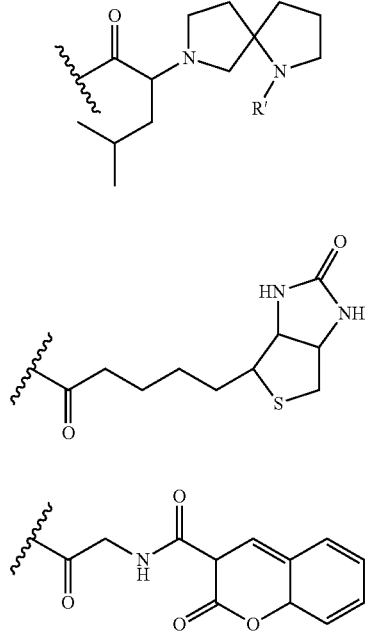

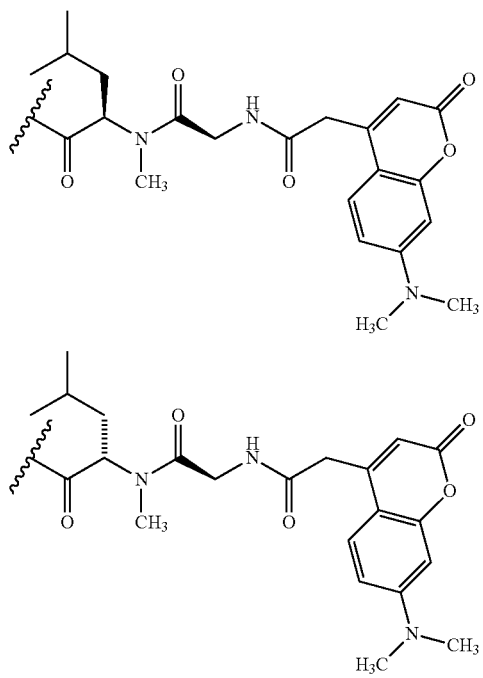

wherein R' is H, Boc, isobutyryl, pyruvyl, or acryloyl.

In another embodiment, R⁵ is a peptide comprising a fluorophore. Another suitable group for R⁵ includes —(N-methyl)leucine-proline-lactate-(fluorophore). Other suitable R⁵ groups having a fluorophore include those having the structure shown below.

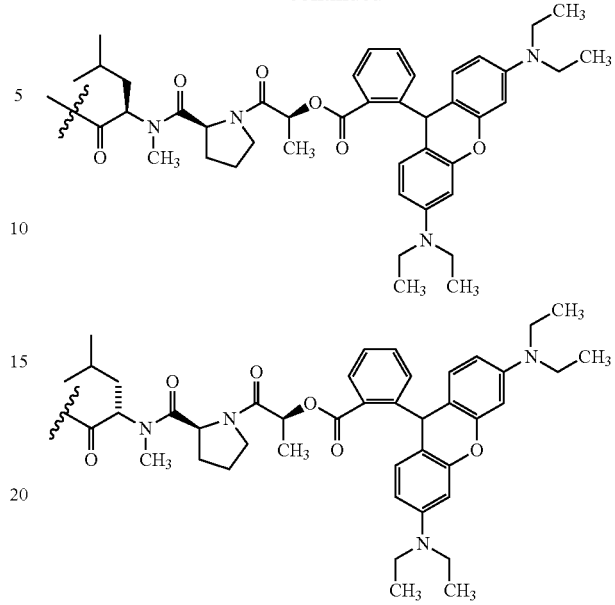

In another embodiment, R⁵ is an amino acid residue, a polypeptide, or a chemical moiety, or linker, bound, e.g., covalently attached, with a support, e.g., a glass or silica plate, an agarose bead, or other polymeric bead, etc. In one embodiment, R⁵ is a group having the formula:

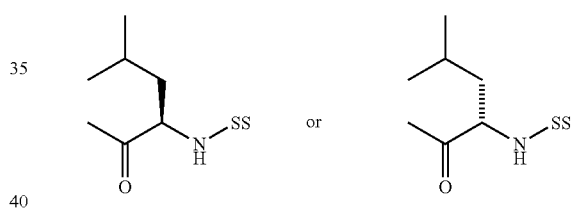

wherein SS represents a solid support. In another embodiment, the chemical linker or moiety is an organic linking group, such as an alkylene or alkenylene group, for example, comprising 1-20 carbon atoms. In another embodiment, R⁵ can be represented as L-SS, wherein L is a bivalent organic linking group and SS is a solid support. Solid supports are known in the art. For example, see MacLean et al., *Pure Appl. Chem.* 71(12):2349-2365 (1999).

When R⁵ comprises an N-methyl-leucine residue, the alpha-carbon atom of that residue can have either (R) or (S) stereochemistry. Other amino acid residues within R⁵ can have either (R) or (S) stereochemistry, but, in one embodiment, they have (S) stereochemistry at their alpha-carbon atom. When R⁵ comprises a lactate residue, the lactate residue is preferably an (S)-lactate residue. In another embodiment, every amino acid residue within R⁵ other than the leucine (or N-methyl-leucine) residue (if present) attached directly to the nitrogen atom of the ring of Formula I has (S) stereochemistry.

In another embodiment, R⁵ contains a fluorophore moiety, e.g., a fluorophore linked with one of the amino acid side chains described above.

In one embodiment, Y is H. In another embodiment, Y is a hydroxyl protecting group. Examples of hydroxyl protecting groups which can be present at Y include an alkyl-substituted silyl moiety, an aryl-substituted silyl moiety, or a silane substituted with both alkyl and aryl moieties. An example of a useful hydroxyl protecting group is a triisopropylsilyl moiety (TIPS). Another suitable protecting group includes trimethylsilyl. Other hydroxyl protecting groups which can be used at Y in Formula I are known in the art and are described in references such as Green and Wuts (1991, Protective Groups in Organic Synthesis, $2^{nd}$ Edition, Wiley, New York).

A first subclass of compounds is a compound according to Formula IA wherein $R^5$ is a moiety having the structure:

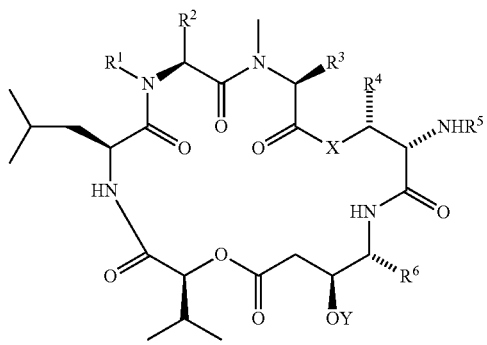

wherein $R^1$ and $R^2$ are independently H or $C_{1-4}$ alkyl, or $R^1$ and $R^2$ together form the alkyl ring of a proline residue;

$R^3$ is selected from the group consisting of a side chain of an amino acid and a first fluorophore;

$R^4$ is H or $CH_3$;

$R^5$ is H, an amine protecting group, an amino acid residue, a polypeptide, a peptide which contains a second fluorophore, a chemical moiety bound to a solid support, or a moiety containing from about 1 to about 30 non-hydrogen atoms;

$R^6$ is an isoleucine side chain or a valine side chain;

X is O or NH; and

Y is H or a hydroxyl protecting group;

provided that if $R^1$ and $R^2$ together form the alkyl ring of a proline residue, $R^4$ is methyl, W is O, X is O, and Z is C(O), then $R^3$ is not an isoleucine side chain, a valine side chain, an alanine side chain, a norleucine side chain, a norvaline side chain, leucine side chain, a histidine side chain, a tryptophan side chain, an arginine side chain, a lysine side chain, a second fluorophore, or a benzyl optionally substituted with OH, —$OCH_3$, —$CO(C_6H_5)$, —Br, —I, —F, —Cl, —$CH_3$, and —$C_2H_5$; or alternatively provided that provided that if $R^1$ and $R^2$ together form the alkyl ring of a proline residue, $R^4$ is methyl, and X is O, then $R^3$ is naphthylmethyl.

In one embodiment in this first subclass, $R^1$ and $R^2$ are H. In another embodiment, $R^1$ and $R^2$ are $C_{1-4}$ alkyl, for example methyl. In another embodiment, $R^1$ is H and $R^2$ is methyl. In another embodiment, $R^1$ is methyl and $R^2$ is H. In a further embodiment, $R^1$ and $R^2$ together form the alkyl ring of a proline residue. That is, in one embodiment, $R^1$ and $R^2$ together form a 1,3-propanediyl group.

In one embodiment within this first subclass, $R^3$ is side chain of an amino acid, in particular a naturally occurring amino acid. In one embodiment, $R^3$ is amino acid side chain such as an isoleucine side chain, i.e., a 2-butyl moiety, preferably having (R) stereochemistry, a valine side chain, i.e., a 2-propyl moiety, an alanine side chain, i.e., a methyl moiety, a norleucine side chain, i.e., a 1-butyl moiety, a norvaline side chain, i.e., a 1-propyl moiety, a leucine side chain, i.e., an isobutyl moiety, preferably having (S) stereochemistry, a phenylalanine side chain, i.e., a benzyl moiety, a histidine side chain, i.e., a 4-imidazolylmethyl moiety, a tryptophan side chain, i.e., a 3-indolylmethyl moiety, a tyrosine side chain, i.e., a 4-hydroxybenzyl moiety, an arginine side chain, i.e., a 4-guanidinylbutyl moiety, and a lysine side chain, i.e., a 4-aminobutyl moiety.

In another embodiment within this first subclass, $R^3$ is a side chain of a non-naturally occurring amino acid. Non-naturally occurring amino acids are known in the art. For example, suitable non-naturally occurring amino acids include, but are not limited to, cycloleucine, homocycloleucine, 9-anthracenyl-alanine, 3-(3-benzothienyl)alanine, 3-cyclohexylalanine, 3,3-diphenylalanine, 3-pyridylalanine, 3-(2-furyl)alanine, and 3-sytrylalanine, 3-(2-thienyl)alanine, 2-phenylglycine, allylglycine, 2-cyclohexylglycine, propargylglycine, 2-(trifluormethyl)phenylalanine, the like. In one embodiment, $R^3$ is a naphthylmethyl group. Alternatively, $R^3$ is a benzyl group substituted with OH, $OCH_3$ and $OCH_2CH_3$, $CO(C_6H_5)$, F, Cl, Br, I, or $CH_3$ and $CH_2CH_3$.

In another embodiment within this first subclass, $R^3$ is a first fluorophore. In another embodiment, $R^3$ contains a fluorophore. Moieties which are fluorophores are known in the art. In one embodiment, the fluorophore is an amino acid side chain as described above further containing a fluorophore moiety (e.g., a fluorophore linked with one of the amino acid side chains described above). Such a fluorophore includes

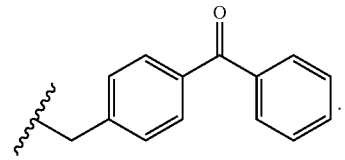

In one embodiment within this first subclass, $R^5$ is H, an amine protecting group, an amino acid residue, a polypeptide, or a peptide which contains a second fluorophore.

In one embodiment within this first subclass, the invention comprises a compound of Formula IA wherein $R^5$ is a hydrogen atom or an amine protecting group suitable for protection of amino acids. Such protecting groups are known in the art and referred to throughout this disclosure. A suitable protecting group for $R^5$ includes, for example, tert-butoxycarbonyl. Examples of suitable protecting groups can be found in references such as Green and Wuts (1991, Protective Groups in Organic Synthesis, Wiley, New York, $2^{nd}$ Edition) and Bodansky (1993, Principles of Peptide Synthesis, Springer, Berlin).

In one embodiment within this first subclass, $R^5$ is an amino acid residue, e.g., a leucine residue, or a polypeptide comprising two or more amino acid residues. In certain embodiments, the $R^5$ group contains 1-10 amino acid residues. In another embodiment, the $R^5$ group contains 1, 2, 3, 4, or 5 amino acid residues. In certain instances, the amino acid residue or polypeptide contains one or more suitable protecting groups. Examples of such amino acid residues and polypeptides include:

—(N-methyl)leucine;
—(N-methyl)leucine-proline;
—(N-CBz-N-methyl)leucine;
—(N-methyl)leucine-proline-lactate;
—(N-methyl)leucine-proline-pyruvate;
—(N-methyl)leucine-proline-lactate-glutamine-pyroglutamate;
—(N-methyl)leucine-proline-lactate-glutamine-cyclopentanoate;

—(N-methyl)leucine-proline-lactate-leucine-pyroglutamate;
—(N-methyl)leucine-proline-lactate-glutamine-cyclopentanoate;
—(N-methyl)leucine-proline-alanine-leucine-pyroglutamate; and
—(N-methyl)leucine-proline-(N-methyl)alanine-leucine-pyroglutamate.

In another embodiment within this first subclass, $R^5$ contains an N-glycidyl-L-proline residue. A suitable value of $R^5$ is —(N-methyl-R-leucine)-S-proline-glycidate.

Other suitable $R^5$ groups include those having the structure shown below.

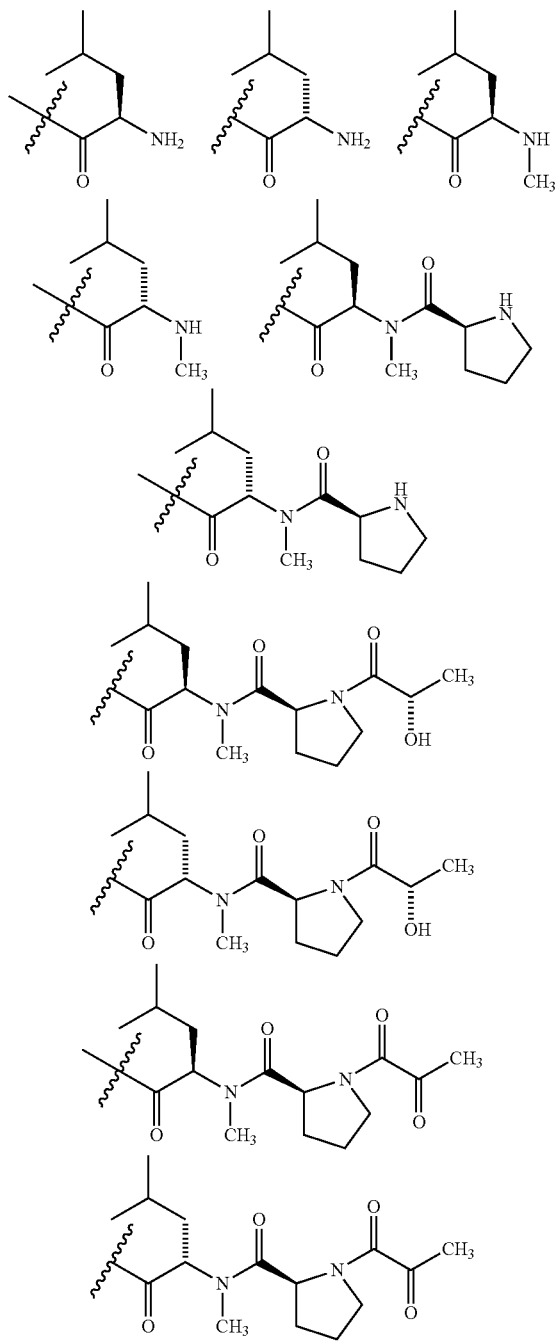

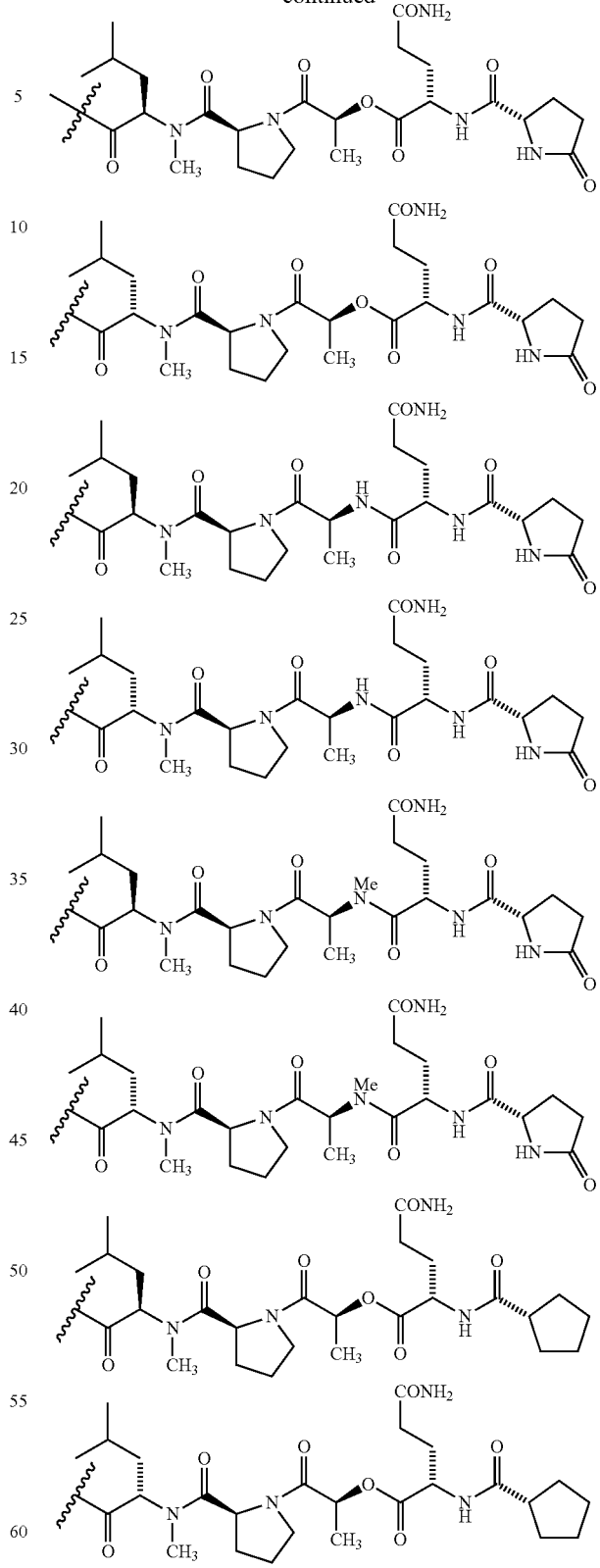

Other suitable groups for $R^5$ include those having an amino acid residue other than one of the common twenty amino acids. Suitable examples of such amino acids are known in the art and include, for example, hydroxyproline, dehydroproline, 4-carboxyglutamic acid, hydroxylysine, N,N-dimethylarginine, iodotyrosine, β-alanine, and the like. In another embodiment, R⁵ is a peptide comprising a fluorophore. Another suitable group for R⁵ includes —(N-methyl)leucine-proline-lactate-(fluorophore). Other suitable R⁵ groups having a fluorophore include those having the structure shown below.

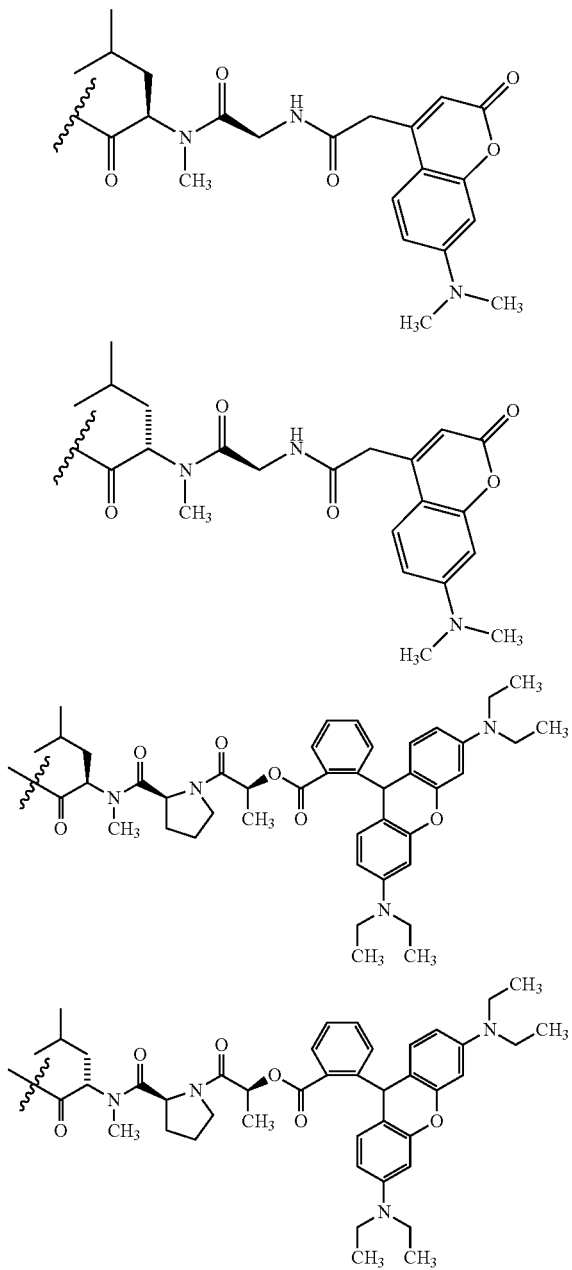

In another embodiment, R⁵ contains a moiety having the formula

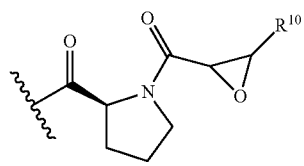

wherein $R^{10}$ is H, $C_{1-4}$ alkyl, or phenyl. In one example of this subclass, $R^{10}$ is H. In this embodiment, the moiety is bound directly to the amine group of the macrocycle forming an amide linkage, i.e., R⁵ is the group shown above. In another embodiment, the moiety is in the terminal position of the R⁵ group. That is, the moiety is connected to the amine group by another moiety, for example, an amino acid residue, a peptide residue, or a linker. In a further embodiment, the moiety shown above is connected to the rest of the R⁵ group by an ester linkage. For example, N-glycidyl-L-proline is used to prepare suitable R⁵ moieties to prepare a compound according to Formula I, IA, or II, or alternatively, N-glycidyl-L-proline is coupled directly with the free amine of the macrocycle, e.g., compound 35, deprotected 61, deprotected 74, deprotected 85, or deprotected 92. In another embodiment, N-glycidyl-L-proline is reacted with the terminus of the R⁵ group, for example, reacted with deprotected free amine of compound 63 shown in Scheme 17.

In another embodiment within this first subclass, R⁵ is an amino acid residue, a polypeptide, or a chemical moiety, or linker, bound, e.g., covalently attached, with a support, e.g., a glass or silica plate, an agarose bead, or other polymeric bead, etc. In one embodiment, R⁵ is a group having the formula:

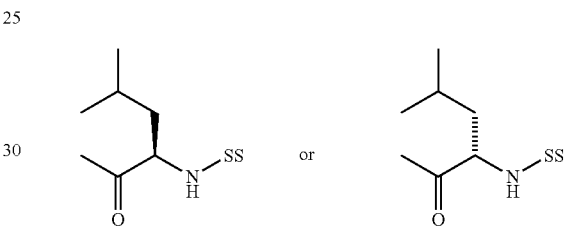

wherein SS represents a solid support. In another embodiment, the chemical linker or moiety is an organic linking group, such as an alkylene or alkenylene group, for example, comprising 1-20 carbon atoms. In another embodiment, R⁵ can be represented as L-SS, wherein L is a bivalent organic linking group and SS is a solid support. Solid supports are known in the art. For example, see MacLean et al., *Pure Appl. Chem.* 71(12):2349-2365 (1999).

When R⁵ comprises an N-methyl-leucine residue, the alpha-carbon atom of that residue can have either (R) or (S) stereochemistry. Other amino acid residues within R⁵ can have either (R) or (S) stereochemistry, but, in one embodiment, they have (S) stereochemistry at their alpha-carbon atom. When R⁵ comprises a lactate residue, the lactate residue is preferably an (S)-lactate residue. In another embodiment, every amino acid residue within R⁵ other than the leucine (or N-methyl-leucine) residue (if present) attached directly to the nitrogen atom of the ring of Formula I has (S) stereochemistry.

In another embodiment within this first subclass, R⁵ contains a fluorophore moiety, e.g., a fluorophore linked with one of the amino acid side chains described above.

In another embodiment within this first subclass, R⁵ is a moiety having from about 1 to about 50 non-hydrogen atoms, e.g., carbon, nitrogen, oxygen, sulfur, halogens, and mixtures thereof. In another embodiment within this first subclass, R⁵ is a moiety having from about 1 to about 40 non-hydrogen atoms. In another embodiment within this first subclass, R⁵ is a moiety having from about 1 to about 30 non-hydrogen atoms. In another embodiment within this first subclass, R⁵ is a moiety having from about 1 to about 20 non-hydrogen atoms. In another embodiment within this first subclass, R⁵ is a moiety having from about 1 to about 10 non-hydrogen atoms. Suitable moieties include, but are not limited to, peptides, carbohydrates, saccharides, oligosaccharides, steroids, bioactive molecules, lipids, nucleotides, nucleosides, vitamins, and the like. Such moieties are bound directly to the amine of the macrocycle, or are connected to the macrocycle amine by an organic linker. Other suitable moieties containing from about 1 to about 50 non-hydrogen atoms include, but are not limited to, moieties having one or more of the following groups: alkyl, alkenyl, alkynyl, cycloalkyl, alkoxy, cycloalkoxy, halogen, amino, thio, keto, aryl, heteroaryl, halo, haloalkyl, aryl, heterocycle, cycloalkyl, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, hydroxy, thiol, acyloxy, azido, alkoxy, carboxy, aminocarbonyl, alkylthiol groups, and combinations thereof.

In one embodiment within this first subclass, Y is H. In another embodiment, Y is a hydroxyl protecting group. Examples of hydroxyl protecting groups which can be present at Y include an alkyl-substituted silyl moiety, an aryl-substituted silyl moiety, or a silane substituted with both alkyl and aryl moieties. An example of a useful hydroxyl protecting group is a triisopropylsilyl moiety (TIPS). Another suitable protecting group includes trimethylsilyl. Other hydroxyl protecting groups which can be used at Y in Formula IA are known in the art and are described in references such as Green and Wuts (1991, Protective Groups in Organic Synthesis, $2^{nd}$ Edition, Wiley, New York).

A second subclass of compounds is a compound according to Formula IA wherein $R^5$ is a moiety such that the compound has the structure

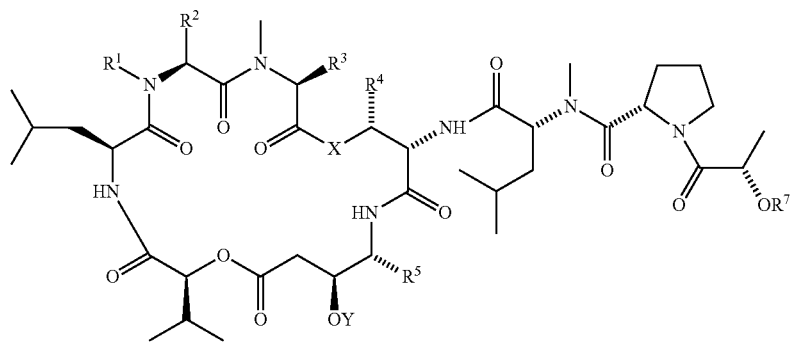

wherein $R^7$ is hydrogen or a chemical moiety which can be enzymatically cleavable (i.e., an enzyme-cleavable moiety). As used herein, an enzyme-cleavable moiety can include any chemical moiety which can be cleaved (i.e., chemically detached from) in the presence of a specific enzyme. Examples of enzymes capable of chemically detaching an enzyme-cleavable moiety include carboxypeptidases, β-lactamase, β-galactosidase, penicillin V-amidase, cytosine deaminase, nitroreductase, alkaline phosphatase, beta-glucuronidase, and catalytic antibodies. Examples of enzyme-cleavable moieties which can be incorporated in a compound described herein include cephalosporins, beta-glucosides, phosphate, pyrophosphate, β-D-galactosides, nitrobenzamidine, cytosine, carbamates, peptides, and amino acids.

In another embodiment within this subclass, $R^7$ is an enzyme-cleavable moiety such as a dipeptide linked with glutamine-pyroglutamate, or a moiety having the structure of one of the following

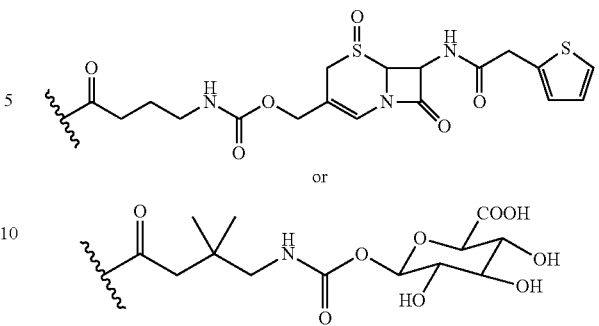

The cephalosporin moiety shown above is cleaved by contact with the enzyme, β-lactamase. An $R^7$ substituent having the structure of the carbohydrate moiety above, for example, is, in one embodiment, in the form of a sodium or potassium salt.

After cleavage of an enzyme-cleavable moiety by an enzyme, the resulting tamandarin analog exhibits one or more of the physiological activities described herein. A tamandarin analog of the present invention having an enzyme-cleavable moiety can, optionally, exhibit these activities before the cleavage of the enzyme-cleavable moiety. However, in a preferred embodiment, the analog exhibits therapeutic activity only following cleavage of the enzyme-cleavable moiety therefrom.

As described above, a tamandarin analog having the structure of Formula I can be bound with a support. The identity of the support is not critical. The support can be substantially any material with which such an analog can be bound, e.g., by covalent attachment through the $R^5$ moiety. Examples of support materials include bonded silicates, cross-linked agarose, polyacrylamide, dextran, and allyl dextran. Such support materials can be chemically modified using reactive chemical moieties in order to facilitate covalent attachment of the analog with the support. Chemical modifications of this type are known in the art, and can, for example, include modification of a support with cyanogen bromide groups, epoxide groups, tresyl groups, and carboxyhexyl groups. Protocols for preparation of a support and subsequent attachment of a compound to the support are available in the art, and can be modified by one skilled in the art for use with a tamandarin analog described herein.

A subclass of useful compounds according to Formula IA are compounds comprising a fluorescent substituent, a photoreactive moiety, such as a moiety having the structure

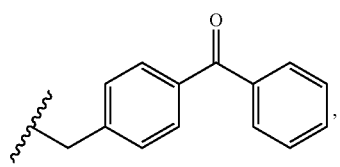

or a moiety bound with a support, e.g., at $R^3$ or $R^5$. Compounds having a such a photoreactive moiety are useful or labeling proteins, for example. Fluorescent substituents and photoreactive moieties are known in the art. Other suitable photoreactive $R^5$ groups include

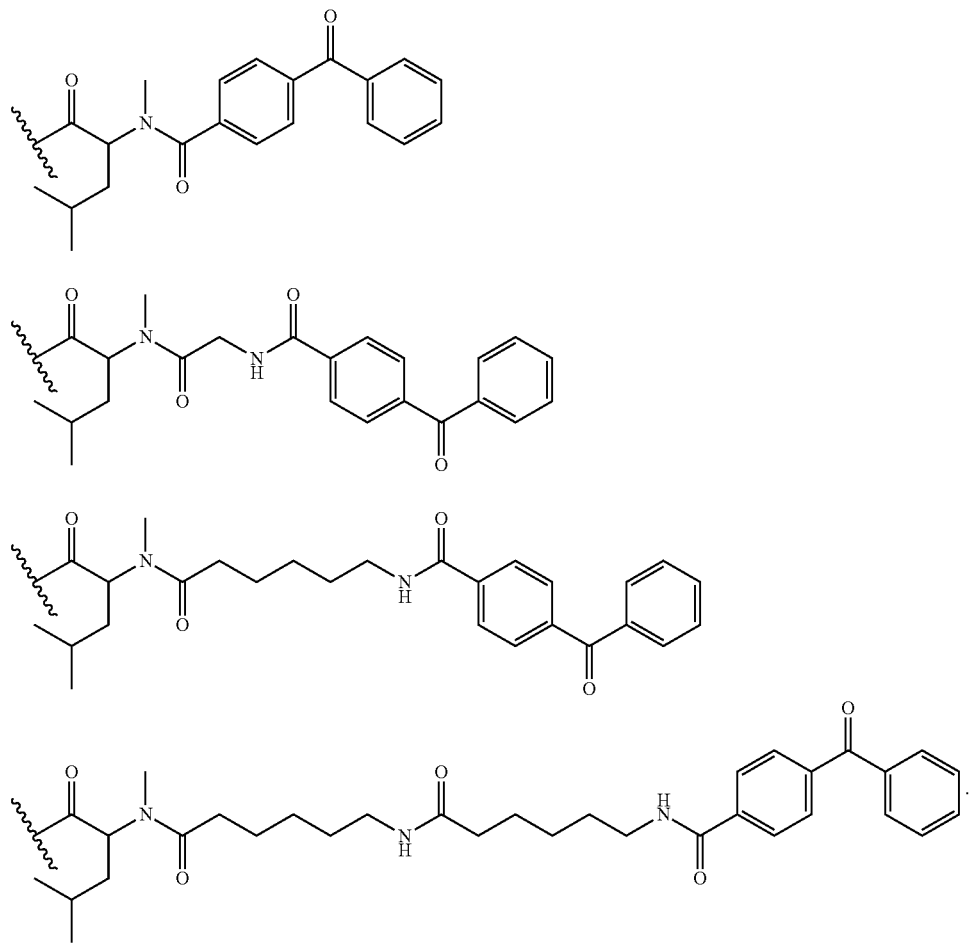

Another subclass of useful compounds is a compound according to Formula IA, wherein $R^1$ is H; $R^2$ is $CH_3$; $R^3$ is a benzyl group optionally substituted with one or more selected from the group consisting of OH, $OCH_3$, $CO(C_6H_5)$, F, Cl, Br, I, $CH_3$, and $CH_2CH_3$, and preferably is $OCH_3$; $R^4$ is $CH_3$; $R^5$ is anyone of the embodiments defined above; $R^6$ is a valine side chain; X is O; and Y is H.

Another subclass of useful compounds is a compound according to Formula IA, wherein $R^1$ is $CH_3$; $R^2$ is $CH_3$; $R^3$ is a benzyl group optionally substituted with one or more selected from the group consisting of OH, $OCH_3$, $CO(C_6H_5)$, F, Cl, Br, I, and $CH_3$, and $CH_2CH_3$, and preferably is $OCH_3$; $R^4$ is $CH_3$; $R^5$ is anyone of the embodiments defined above; $R^6$ is a valine side chain; X is O; and Y is H.

Another subclass of useful compounds is a compound according to Formula IA, wherein $R^1$ and $R^2$ together form the alkyl ring of a proline residue; $R^3$ is a benzyl group optionally substituted with one or more selected from the group consisting of OH, $OCH_3$, $CO(C_6H_5)$, F, Cl, Br, I, $CH_3$, and $C_2H_5$, preferably $OCH_3$; $R^4$ is H; $R^5$ is anyone of the embodiments defined above; $R^6$ is a valine side chain; X is O; and Y is H.

Another subclass of useful compounds is a compound according to Formula IA, wherein $R^1$ and $R^2$ together form the alkyl ring of a proline residue; $R^3$ is a naphthylmethyl group; $R^4$ is $CH_3$; $R^5$ is anyone of the embodiments defined above; $R^6$ is a valine side chain; X is O; and Y is H.

Another subclass of useful compounds of Formula IA is a compound having the formula

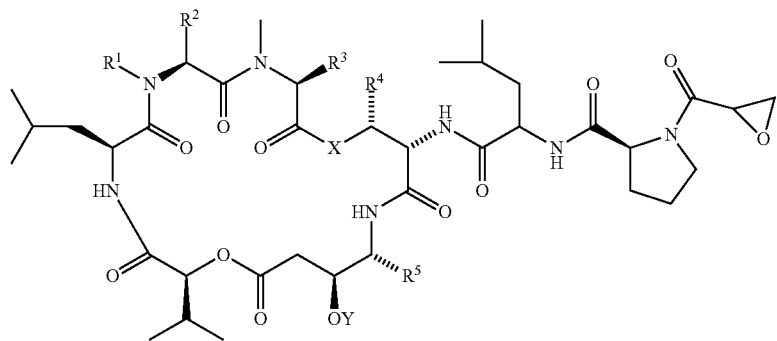

wherein $R^1$-$R^6$, X, and Y are defined as for a compound of Formula IA.

A further aspect of the invention is a compound according to Formula II

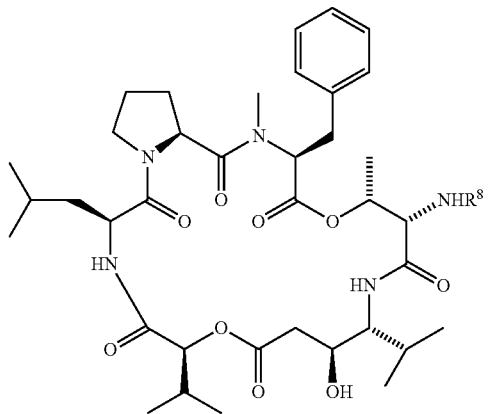

wherein $R^8$ is defined as for $R^5$. In one embodiment, $R^8$ is H, an amine protecting group, or —(N-methyl)leucine-proline-lactate.

Examples of suitable, novel compounds, which are useful in the methods and compositions disclosed herein, include a compound according to Formula I, IA, or II wherein:

$R^1$ and $R^2$ together form the alkyl ring of a proline residue, $R^3$ is benzyl, $R^4$ is $CH_3$, $R^5$ is (N-methyl-R-leucine)-S-proline-S-lactate, $R^6$ is a valine side chain, X is O, and Y is H (compound 36);

$R^1$ and $R^2$ together form the alkyl ring of a proline residue, $R^3$ is benzyl, $R^4$ is $CH_3$, $R^5$ is H, $R^6$ is a valine side chain, X is O, and Y is H;

$R^1$ and $R^2$ together form the alkyl ring of a proline residue, $R^3$ is benzyl, $R^4$ is $CH_3$, $R^5$ is H.HCl, $R^6$ is a valine side chain, X is O, and Y is H (compound 35);

$R^1$ and $R^2$ together form the alkyl ring of a proline residue, $R^3$ is benzyl, $R^4$ is $CH_3$, $R^5$ is Boc, $R^6$ is a valine side chain, X is O, and Y is TIPS (compound 34);

$R^1$ and $R^2$ together form the alkyl ring of a proline residue, $R^3$ is benzyl, $R^4$ is $CH_3$, $R^5$ is Boc, $R^6$ is a valine side chain, X is O, and Y is H;

$R^1$ and $R^2$ together form the alkyl ring of a proline residue, $R^3$ is 4-methoxybenzyl, $R^4$ is H, $R^5$ is (N-methyl-R-leucine)-S-proline-S-lactate, $R^6$ is a valine side chain, X is O, and Y is H (compound 62);

$R^1$ and $R^2$ together form the alkyl ring of a proline residue, $R^3$ is 4-methoxybenzyl, $R^4$ is H, $R^5$ is Boc, $R^6$ is a valine side chain, X is O, and Y is H (compound 61);

$R^1$ and $R^2$ together form the alkyl ring of a proline residue, $R^3$ is 4-methoxybenzyl, $R^4$ is H, $R^5$ is H, $R^6$ is a valine side chain, X is O, and Y is H;

$R^1$ and $R^2$ together form the alkyl ring of a proline residue, $R^3$ is 4-methoxybenzyl, $R^4$ is H, $R^5$ is (N-methyl-R-leucine)-S-proline-S-pyruvate, $R^6$ is a valine side chain, X is O, and Y is H (compound 64);

$R^1$ and $R^2$ together form the alkyl ring of a proline residue, $R^3$ is 4-methoxybenzyl, $R^4$ is H, $R^5$ is (N-methyl-R-leucine), $R^6$ is a valine side chain, X is O, and Y is H;

$R^1$ and $R^2$ together form the alkyl ring of a proline residue, $R^3$ is 4-methoxybenzyl, $R^4$ is H, $R^5$ is N-Cbz-N-methyl-R-leucine, $R^6$ is a valine side chain, X is O, and Y is H (compound 63);

$R^1$ and $R^2$ together form the alkyl ring of a proline residue, $R^3$ is 4-methoxybenzyl, $R^4$ is H, $R^5$ is H.HCl, $R^6$ is a valine side chain, X is O, and Y is H;

$R^1$ is H, $R^2$ is $CH_3$, $R^3$ is 4-methoxybenzyl, $R^4$ is $CH_3$, $R^5$ is (N-methyl-R-leucine)-S-proline-S-lactate, $R^6$ is a valine side chain, X is O, and Y is H (compound 75);

$R^1$ is H, $R^2$ is $CH_3$, $R^3$ is 4-methoxybenzyl, $R^4$ is $CH_3$, $R^5$ is Boc, $R^6$ is a valine side chain, X is O, and Y is H (compound 74);

$R^1$ is H, $R^2$ is $CH_3$, $R^3$ is 4-methoxybenzyl, $R^4$ is $CH_3$, $R^5$ is H, $R^6$ is a valine side chain, X is O, and Y is H;

$R^1$ is $CH^3$, $R^2$ is $CH_3$, $R^3$ is 4-methoxybenzyl, $R^4$ is $CH_3$, $R^5$ is (N-methyl-R-leucine)-S-proline-S-lactate, $R^6$ is a valine side chain, X is O, and Y is H (compound 150);

$R^1$ is $CH_3$, $R^2$ is $CH_3$, $R^3$ is 4-methoxybenzyl, $R^4$ is $CH_3$, $R^5$ is Boc, $R^6$ is a valine side chain, X is O, and Y is H (compound 85);

$R^1$ is $CH^3$, $R^2$ is $CH_3$, $R^3$ is 4-methoxybenzyl, $R^4$ is $CH_3$, $R^5$ is H, $R^6$ is a valine side chain, X is O, and Y is H;

$R^1$ and $R^2$ together form the alkyl ring of a proline residue, $R^3$ is 2-naphthylmethyl, $R^4$ is $CH_3$, $R^5$ is (N-methyl-R-leucine)-S-proline-S-lactate, $R^6$ is a valine side chain, X is O, and Y is H (compound 93);

$R^1$ and $R^2$ together form the alkyl ring of a proline residue, $R^3$ is 2-naphthylmethyl, $R^4$ is $CH_3$, $R^5$ is Boc, $R^6$ is a valine side chain, X is O, and Y is H (compound 92);

$R^1$ and $R^2$ together form the alkyl ring of a proline residue, $R^3$ is 2-naphthylmethyl, $R^4$ is $CH_3$, $R^5$ is H, $R^6$ is a valine side chain, X is O, and Y is H;

$R^1$ and $R^2$ together form the alkyl ring of a proline residue, $R^3$ is 4-methoxybenzyl, $R^4$ is $CH_3$, $R^5$ is (N-methyl-R-leucine)-S-proline-S-lactate, $R^6$ is a valine side chain, X is NH, and Y is H;

$R^1$ and $R^2$ together form the alkyl ring of a proline residue, $R^3$ is 4-methoxybenzyl, $R^4$ is $CH_3$, $R^5$ is H, $R^6$ is a valine side chain, X is NH, and Y is H;

$R^1$ and $R^2$ together form the alkyl ring of a proline residue, $R^3$ is 4-methoxybenzyl, $R^4$ is $CH_3$, $R^5$ is Boc, $R^6$ is a valine side chain, X is NH, and Y is H;

and pharmaceutically acceptable salts thereof.

The present invention also includes a salt of a compound according to Formula I, IA, or II. The term salt refers to an acid- and/or base-addition salt of a compound according to Formula I, IA, or II. Acid-addition salts can be formed by adding an appropriate acid to the compound according to Formula I, IA, or II. Base-addition salts can be formed by adding an appropriate base to the compound according to Formula I, IA, or II. Said acid or base does not substantially degrade, decompose, or destroy said compound according to Formula I, IA, or II. Examples of suitable salts include hydrochloride, hydrobromide, acetate, fumarate, maleate, oxalate, and succinate salts. Other suitable salts include sodium, potassium, carbonate, and tromethamine salts.

It is further understood that the present invention encompasses tautomers of a compound of Formula I, IA, or II. Tautomers are well-known in the art and include keto-enol tautomers.

The compounds of Formula I, IA, or II may also be solvated, including hydrated. Hydration may occur during manufacturing of the compounds or compositions comprising the compounds, or the hydration may occur over time due to the hygroscopic nature of the compounds.

Certain compounds within the scope of Formula I, IA, or II may be derivatives referred to as "prodrugs." The expression "prodrug" denotes a derivative of a known direct acting drug, which derivative has enhanced delivery characteristics and therapeutic value as compared to the drug, and is transformed into the active drug by an enzymatic or chemical process. Prodrugs are derivatives of the compounds of the invention which have metabolically cleavable groups and become by solvolysis or under physiological conditions the compounds of the invention which are pharmaceutically active in vivo. An acid derivative form may offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with an amine.

When any variable occurs more than one time in any constituent or in Formula I, its definition on each occurrence is independent of its definition at every other occurrence, unless otherwise indicated. Also, combinations of substituents and/or variables are permissible only if such combinations result in stable compounds.

It is further understood that compounds disclosed in U.S. Pat. No. 6,509,315 are excluded from the present invention as described in the above provisos.

DEFINITIONS

As used herein, each of the following terms has the meaning associated with it in this section.

As used herein, certain amino acid residues (in particular the twenty common amino acids) are represented by the full name thereof, by the three letter code corresponding thereto, or by the one-letter code corresponding thereto, as indicated by the following:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | N |

As used herein, the term "amino acid side chain" refers to a moiety comprising all of the atoms of an amino acid excluding the alpha-carbon atom, a hydrogen atom bound with the alpha-carbon, the atoms of the alpha-carboxyl moiety and the alpha-amine moiety. By way of example, an "alanine side chain" refers to a methyl group, a "valine side chain" refers to a 2-propyl (or isopropyl) group, and a 3-cyclohexylalanine side chain refers to a cyclohexylmethyl group (i.e., $C_6H_{11}$—$CH_2$—).

"Inhibition" of a process in a cell (e.g., inhibition of protein synthesis, inhibition of cell growth, inhibition of cell cycle progression, inhibition of cell proliferation, or inhibition of tumorigenesis) means reduction (e.g., by at least 10%, 25%, 50%, 75%, 90%, 95%, or even 100%) of the rate at which the process proceeds, reduction (e.g., by at least 10%, 25%, 50%, 75%, 90%, 95%, or even 100%) of the rate at which the process is initiated, or both.

"Enhancement" of a process in a cell (e.g., enhancement of apoptosis) means increasing (e.g. by at least 10%, 25%, 50%, 75%, 90%, 95%, or even 100%) the rate at which the process proceeds, increasing (e.g., by at least 10%, 25%, 50%, 75%, 90%, 95%, or even 100%) the rate at which the process is initiated, or both.

As used herein, the term "pharmaceutically acceptable carrier" means a chemical composition with which a tamandarin analog or fragment, as described herein, can be combined and which, following the combination, can be administered to a subject (e.g., a human or other animal).

As used herein, the term "physiologically acceptable" ester or salt means an ester or salt form of a tamandarin analog or fragment, as described herein, which is compatible with other ingredients of a pharmaceutical composition and which is not deleterious to a subject to which the composition is to be administered.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration can include, but is not limited to, subcutaous, intraperitoneal, intramuscular, intrasternal injection, and kidney dialytic infusion techniques.

As used herein, the term "anti-viral activity" means preventing replication of a virus in the cell, preventing infection of the cell by a virus, or reversing a physiological effect of infection of the cell by a virus. An anti-viral agent is an composition of matter which, when delivered to a cell, exhibits anti-viral activities. Anti-viral agents are well known and described in the literature. By way of example, AZT (zidovudine) is an anti-viral agent which is thought to prevent replication of HIV in human cells.

The terms describing different chemical moieties used herein are terms of the art and are understood by one of ordinary skill in the art.

The term "homoproline," as used herein, refers to a proline moiety containing an additional methylene group in the ring, i.e., having a 6-membered ring.

The term "non-amino acid moiety" as used herein refers to a moiety that does not contain both an amino group and a carboxy group. Such a moiety is exemplified above for $R^5$. A non-amino acid moiety may be a moiety at the terminus of the $R^5$ group, for example, those shown above.

The term "protecting group," as used herein by itself or as part of another group, refers to a chemical moiety that can readily be attached to a particular functional group (and forming a protected functional group) when desired to protect said functional group from undesired chemical reactions and then at a later point be removed from said protected functional group to reveal the original functional group. See, for example, Green and Wuts (1991, Protective Groups in Organic Synthesis, Wiley, New York, $2^{nd}$ Edition, pages 1-9), which is hereby incorporated by reference in its entirety. Examples of protecting groups are well known in the art. Examples of suitable protecting groups can be found in references such as Green and Wuts (1991, Protective Groups in Organic Synthesis, Wiley, New York, $2^{nd}$ Edition) and Bodansky (1993, Principles of Peptide Synthesis, Springer, Berlin). Specific, non-limiting examples of protecting groups include acetyl, benzyl, t-butoxycarbonyl (Boc), benzoyl, dimethylisopropylsilyl, t-butyldimethylsilyl, methoxymethyl, and benzyloxycarbonyl. Protecting groups attached to a solid support are also suitable.

The term "amine protecting group," as used herein by itself or as part of another group, refers to a chemical moiety that can readily be attached to an amine group (and forming a protected amine) when desired to protect said amine from undesired chemical reactions and then at a later point be removed from said protected amine to reveal the original amine. Examples of amine protecting groups are well known in the art. Examples of suitable amine protecting groups can be found in references such as Green and Wuts (1991, Protective Groups in Organic Synthesis, Wiley, New York, $2^{nd}$ Edition) and Bodansky (1993, Principles of Peptide Synthesis, Springer, Berlin). Specific, non-limiting examples of amine protecting groups include carbamates such as t-butoxycarbonyl, methoxycarbonyl, and benzyloxycarbonyl, amides such as formamide and trifluoroacetamide, and cyclic imides such as N-phthalimido.

The term "hydroxy protecting group," as used herein by itself or as part of another group, refers to a chemical moiety that can readily be attached to an hydroxy group (and forming a protected hydroxy) when desired to protect said amine from undesired chemical reactions and then at a later point be removed from said protected hydroxy to reveal the original hydroxy group. Examples of hydroxy protecting groups are well known in the art. Examples of suitable hydroxy protecting groups can be found in references such as Green and Wuts (1991, Protective Groups in Organic Synthesis, Wiley, New York, $2^{nd}$ Edition) and Bodansky (1993, Principles of Peptide Synthesis, Springer, Berlin). Specific, non-limiting examples of amine protecting groups include ethers such as methoxymethyl, tetrahydropyranyl, and benzyl, silyl ethers such as trimethyl silyl and triisopropylsilyl, and carbonates such as 9-fluorenylmethyl and benzyl.

Although detailed definitions have not been provided for every term used herein, each term is understood by one of ordinary skill in the art.

Compositions

A composition according to the present invention includes a pharmaceutical composition comprising a novel compound of Formula I, IA, or II, as defined above, and one or more pharmaceutically acceptable excipients. Preferred compositions of the present invention are pharmaceutical compositions comprising a compound selected from one or more embodiments listed above, and one or more pharmaceutically acceptable excipients. Pharmaceutical compositions that comprise one or more compounds of Formula I, IA, or II may be formulated, as is well known in the prior art, such as by reference to known compilations as Remington's Pharmaceutical Sciences, Mack Publishing Co., Easton, Pa., USA.

In one embodiment of the invention, the composition comprises a compound selected from one or more of the individual embodiments listed above.

The invention encompasses pharmaceutical compositions comprising at least one of the tamandarin analogs and the physiologically active fragments described herein. Such compositions can comprise the analog/fragment and a pharmaceutically acceptable carrier. By way of example, a pharmaceutical composition according to the invention comprises a pharmaceutically acceptable carrier and a tamandarin analog having the structure of either Formula I, IA, or II as an active agent. As a further example, a pharmaceutical composition according to the invention comprises a pharmaceutically-acceptable carrier and one or more of the following compounds:

In another embodiment, a pharmaceutical composition of the invention further comprises one or more additional pharmaceutically active agents such as, other tumor therapy agents, other anti-infective agents, and the like.

Such pharmaceutical compositions can be used, for example, in the methods described herein and for inhibiting one or more of protein synthesis, cell cycle progression, tumorigenesis, growth, and proliferation in a cell. In addition, such compositions can be used in the methods described herein for enhancing apoptosis in a cell.

Pharmaceutical compositions that are useful in the methods of the invention can be administered systemically in oral solid formulations, ophthalmic, suppository, aerosol, topical, or other similar formulations. In addition to the active agent, such pharmaceutical compositions can contain pharmaceutically-acceptable carriers and other ingredients known to enhance and facilitate drug administration. Other possible formulations, such as nanoparticles, liposomes, resealed erythrocytes, and immunologically based systems, can also be used to administer the active agent according to the methods of the invention.

The invention encompasses pharmaceutical compositions which consist of the active agent, in a form suitable for administration to a subject, or the pharmaceutical composition comprises the active agent and one or more pharmaceutically acceptable carriers, one or more additional ingredients, or some combination of these. The active agent can be present in the pharmaceutical composition in the form of a physiologically acceptable ester or salt, such as in combination with a physiologically acceptable cation or anion, as is well known in the art.

The formulations of the pharmaceutical compositions described herein can be prepared by any method known or hereafter developed. In general, such preparatory methods include the step of bringing the active agent into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it is understood by the skilled artisan that such compositions are generally suitable for administration to animals of all sorts. Modification of pharmaceutical compositions suitable for administration to humans in order to render the compositions suitable for administration to various animals is well understood, and the ordinarily skilled artisan can design and perform such modification with merely ordinary, if any, experimentation. Subjects to which administration of the pharmaceutical compositions of the invention is contemplated include, but are not limited to, humans and other primates, and mammals including commercially relevant mammals such as cattle, pigs, horses, sheep, cats, and dogs.

Pharmaceutical compositions that are useful in the methods of the invention can be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active agent, and immunologically-based formulations.

A pharmaceutical composition of the invention can be prepared, packaged, or sold in bulk, as a single unit dose, or as a plurality of single unit doses. As used herein, a "unit dose" is a discrete amount of the pharmaceutical composition comprising a predetermined amount of the active agent. The amount of the active agent is generally equal to the dosage of the active agent which would be administered to a subject or a convenient fraction of such a dosage such as, for example, one-half or one-third of such a dosage.

Controlled- or sustained-release formulations of a pharmaceutical composition of the invention can be made using conventional technology.

A formulation of a pharmaceutical composition of the invention suitable for oral administration can be prepared, packaged, or sold in the form of a discrete solid dose unit including, but not limited to, a tablet, a hard or soft capsule, a cachet, a troche, or a lozenge, each containing a predetermined amount of the active agent. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active agent may, for example, be made by compressing or molding the active agent, optionally with one or more additional ingredients. Compressed tablets can be prepared by compressing, in a suitable device, the active agent in a free-flowing form such as a powder or granular preparation, optionally mixed with one or more of a binder, a lubricant, an excipient, a surface active agent, and a dispersing agent. Molded tablets can be made by molding, in a suitable device, a mixture of the active agent, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginate. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearate, silica, and talc.

Tablets can be non-coated or they can be coated using known methods to achieve delayed disintegration in the gastrointestinal tract of a subject, thereby providing sustained release and absorption of the active agent. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Hard capsules comprising the active agent can be made using a physiologically degradable composition, such as gelatin. Such hard capsules comprise the active agent, and can further comprise additional ingredients including, for example, an inert solid diluent such as calcium carbonate, calcium phosphate, or kaolin.

Soft gelatin capsules comprising the active agent can be made using a physiologically degradable composition, such as gelatin. Such soft capsules comprise the active agent, which can be mixed with water or an oil medium such as peanut oil, liquid paraffin, or olive oil.

Liquid formulations of a pharmaceutical composition of the invention which are suitable for oral administration can be prepared, packaged, and sold either in liquid form or in the form of a dry product intended for reconstitution with water or another suitable vehicle prior to use.

Liquid suspensions can be prepared using conventional methods to achieve suspension of the active agent in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions can further comprise one or more additional ingredients including, but not limited to, suspending agents, dispersing or wetting agents, emulsifying agents, demulcents, preservatives, buffers, salts, flavorings, coloring agents, and sweetening agents. Oily suspensions can further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbate, and sorbate. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active agent in aqueous or oily solvents can be prepared in substantially the same manner as liquid suspensions, the primary difference being that the active agent is dissolved, rather than suspended, in the solvent. Liquid solutions of the pharmaceutical composition of the invention can comprise each of the components described with regard to liquid suspensions, it being understood that suspending agents will not necessarily aid dissolution of the active agent in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention can be prepared using known methods. Such formulations can be administered directly to a subject, used, for example, to form tablets, to fill capsules, or to prepare an aqueous or oily suspension or solution by addition of an aqueous or oily vehicle thereto. Each of these formulations can further comprise one or more of dispersing or wetting agent, a suspending agent, and a preservative. Additional excipients, such as fillers and sweetening, flavoring, or coloring agents, can also be included in these formulations.

In another embodiment, a pharmaceutical composition of the invention is prepared, packaged, or sold in the form of oil-in-water emulsion or a water-in-oil emulsion. The oily phase can be a vegetable oil such as olive or arachis oil, a mineral oil such as liquid paraffin, or a combination of these. Such compositions can further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions can also contain additional ingredients including, for example, sweetening or flavoring agents.

In another embodiment, a pharmaceutical composition of the invention is prepared, packaged, or sold in a formulation suitable for rectal administration. Such a composition can be in the form of, for example, a suppository, a retention enema preparation, and a solution for rectal or colonic irrigation.

Suppository formulations can be made by combining the active agent with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations can further comprise various additional ingredients including, but not limited to, antioxidants and preservatives.

Retention enema preparations or solutions for rectal or colonic irrigation can be made by combining the active agent with a pharmaceutically acceptable liquid carrier. As is well known in the art, enema preparations can be administered using, and can be packaged within, a delivery device adapted to the rectal anatomy of the subject. Enema preparations can further comprise various additional ingredients including, but not limited to, antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation can be made by combining the active agent with a pharmaceutically acceptable liquid carrier. As is well known in the art, douche preparations can be administered using, and can be packaged within, a delivery device adapted to the vaginal anatomy of the subject. Douche preparations can further comprise various additional ingredients including, but not limited to, antioxidants, antibiotics, anti-fungal agents, and preservatives.

Formulations of a pharmaceutical composition suitable for parenteral administration can comprise the active agent combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations can further comprise one or more additional ingredients including, but not limited to, suspending, stabilizing, or dispersing agents. In one embodiment of a formulation for parenteral administration, the active agent is provided in dry (i.e., powder or granular) form for reconstitution with a suitable vehicle (e.g., sterile pyrogen-free water) prior to parenteral administration of the reconstituted composition.

In another embodiment, the pharmaceutical composition is prepared, packaged, or sold in the form of a sterile injectable aqueous or oily suspension or solution. This suspension or solution can be formulated according to the known art, and can comprise, in addition to the active agent, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active agent in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active agent, although the concentration of the active agent can be as high as the solubility limit of the active agent in the solvent. Formulations for topical administration can further comprise one or more of the additional ingredients described herein.

A pharmaceutical composition of the invention can be prepared, packaged, or sold in a formulation suitable for pulmonary administration via the buccal cavity. Such a formulation can comprise dry particles which comprise the active agent and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active agent dissolved or suspended in a low-boiling propellant in a sealed container. In one embodiment, such powders comprise particles wherein at least 98% of the particles by weight have a diameter greater than 0.5 nanometers and at least 95% of the particles by number have a diameter less than 7 nanometers. In another embodiment, at least 95% of the particles by weight have a diameter greater than 1 nanometer and at least 90% of the particles by number have a diameter less than 6 nanometers. Dry powder compositions, in one embodiment, include a solid fine powder diluent such as sugar and are conveniently provided in a unit dose form.

Low boiling propellants generally include liquid propellants having a boiling point of below 65° F. at atmospheric pressure. In one embodiment, the propellant can constitute 50 to 99.9% (w/w) of the composition, and the active agent can constitute 0.1 to 20% (w/w) of the composition. The propellant can further comprise additional ingredients such as a liquid non-ionic or solid anionic surfactant or a solid diluent (preferably having a particle size of the same order as particles comprising the active agent).

Pharmaceutical compositions of the invention formulated for pulmonary delivery can also provide the active agent in the form of droplets of a solution or suspension. Such formulations can be prepared, packaged, or sold as aqueous or dilute alcoholic solutions or suspensions, optionally sterile, comprising the active agent, and can conveniently be administered using any nebulization or atomization device. Such formulations can further comprise one or more additional ingredients including, but not limited to, a flavoring agent such as saccharin sodium, a volatile oil, a buffering agent, a surface active agent, or a preservative such as methylhydroxybenzoate. In one embodiment, the droplets provided by this route of administration have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active agent and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about 0.1% (w/w) to about 100% (w/w) of the active agent, and can further comprise one or more of the additional ingredients described herein.

A pharmaceutical composition of the invention can be prepared, packaged, or sold in a formulation suitable for buccal administration. Such formulations may, for example, be in the form of tablets or lozenges made using conventional methods, and may, for example, contain 0.1 to 20% (w/w) active agent, the balance comprising an orally dissolvable or degradable composition and, optionally, one or more of the additional ingredients described herein. Alternatively, formulations suitable for buccal administration can comprise a powder or an aerosolized or atomized solution or suspension comprising the active agent. Such powdered, aerosolized, or aerosolized formulations, when dispersed, have an average particle or droplet size, in one embodiment, in the range from about 0.1 to about 200 nanometers, and can further comprise one or more of the additional ingredients described herein.

In another embodiment, a pharmaceutical composition of the invention is prepared, packaged, or sold in a formulation suitable for ophthalmic administration. Such formulations may, for example, be in the form of eye drops including, for example, a 0.1-1.0% (w/w) solution or suspension of the active agent in an aqueous or oily liquid carrier. Such drops can further comprise buffering agents, salts, or one or more other of the additional ingredients described herein. Other ophthalmically-administrable formulations which are useful include those which comprise the active agent in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; anti-fungal agents; stabilizing agents; and pharmaceutically acceptable polymeric or hydrophobic materials. Other "additional ingredients" which can be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The relative amounts of the active agent, the pharmaceutically acceptable Carrier, and any additional ingredients in a pharmaceutical composition of the invention will vary, depending upon the identity, size, and the type and severity of condition of the subject treated and further depending upon the route by which the composition is to be administered. By way of example, the composition can comprise between 0.1% and 100% (w/w) active agent.

In another embodiment, the present invention is directed to a composition comprising a compound of Formula I, IA, or II and a carrier, wherein said carrier is suitable for an assay. Such carriers may include solid carriers and liquid carriers. A composition suitable for an assay may, but not necessarily, be sterile. Examples of suitable carriers for assays include dimethylsulfoxide, ethanol, dichloromethane, methanol, chloroform, N,N-dimethylformamide, and the like. In one embodiment, the present invention is directed to a composition consisting essentially of a compound of Formula I, IA, or II and a carrier, wherein said carrier is suitable for an assay.

Uses of the Compounds and Compositions

Tamandarin analogs and physiologically active fragments thereof, as disclosed herein, such as compounds having the structure of Formula I, IA, or II, can be used to affect a variety of physiological processes. Each of these compounds can be used to inhibit protein synthesis. Furthermore, the compounds can be used to inhibit progression of a cell through the cell cycle. While not being bound by any particular theory of operation, it is believed that the cell cycle-inhibiting activity of the compounds can be attributed to inhibition of protein synthesis and possibly also to inhibition of other cellular activities associated with DNA replication or cell division. Tamandarin analogs and their active fragments also induce apoptosis in cells. The physiological activities attributable to tamandarin analogs and fragments make these compounds useful for alleviating a variety of disorders in which one or more of cell growth, proliferation, and survival are aberrant. Examples of such disorders include cancers at various stages, e.g., tumorigenesis, tumor growth, and metastasis, and viral infections at various stages, e.g., infection of cells with virus particles, production of virus particles within a cell, and survival of virus-infected cells. Furthermore, the compounds of the present invention can be used to treat cancers (e.g., breast cancer), viral, fungal, parasitic, and bacterial infections, autoimmune disorders, allergies, other hyper-immune disorders, and atherosclerosis.

The subject of the method disclosed herein is preferably an animal, including, but not limited, a cow, horse, sheep, pig, chicken, turkey, quail, cat, dog, mouse, rat, rabbit, and guinea pig, and is more preferably a mammal, and most preferably a human.

The tamandarin analogs and fragments described herein can be used for anti-proliferative, anti-tumor, anti-viral, and immunosuppressive purposes. Accordingly, a further aspect of the present invention is directed to a method of inhibiting or preventing the growth of a cancer cell, comprising contacting said cancer cell with an effective amount of a compound of Formula I, IA, or II. For example, these compounds can be used in a pharmaceutical preparation or medicament to be administered to a patient afflicted with a disorder in which one or more of protein synthesis, cell growth, proliferation, and survival are aberrant. Such medicaments can be used to treat disorders such as cancers (e.g., breast cancer). Examples of anti-tumor activities that can be exhibited by the compounds described herein include inhibition of tumorigenesis, inhibition of metastasis, inhibition of tumor cell growth, inhibition of tumor cell proliferation, and enhancement of tumor cell apoptosis. Dehydrodidemnin exhibits activity against cell lines derived from several human solid tumor types, including non-small cell lung cancer and colon tumor cell lines, and exhibits selective anti-tumor activity against non-small cell lung cancer, melanomas, ovarian cancer, and colorectal cancer (Depenbrock et al., *Brit. J. Cancer* 78:739-744 (1998)). The tamandarin analogs and fragments described herein exhibit anti-tumor activities in cells of one or more of these lines, as well as in cells of the corresponding tumor type in vivo. Determination of the effectiveness of any particular tamandarin analog or fragment described herein against any particular tumor type can be made using standard methods involving, for example, one or more of the 60 standard tumor cell lines maintained in the U.S. National Cancer Institute drug screening program.

A further aspect of the present invention is directed to a method of inhibiting, treating, or preventing a viral infection comprising administering a compound of Formula I, IA, or II to a subject in need of such treatment. Examples of anti-viral activities that can be exhibited by the tamandarin analogs and fragments described herein include inhibition of binding of a virus with a cellular target, inhibition of infection of a cell by a virus, inhibition of cellular synthesis of virus components, inhibition of intracellular assembly of virus particles, inhibition of release of virus particles from an infected cell, inhibition of growth of a cell infected by a virus, inhibition of proliferation of a cell infected by a virus, and induction of death (i.e., apoptosis) of a cell infected by a virus. The antiviral activity of the compounds described herein can, for example, be used to treat or prevent viral infections of mammals and associated symptoms. By way of illustration, a didemnin analog or fragment described herein can be used to treat or prevent infections by viruses such as Rift Valley Fever virus, Dengue virus, or any of the equine encephalitis viruses.

In a further embodiment, the present invention is directed to method of providing immunosuppressive therapy to a subject in need thereof, comprising administering an effective amount of a compound of Formula I, IA, or II to said subject. Examples of immunosuppressive activities that can be exhibited by the tamandarin analogs and fragments described herein include inhibition of a cellular immune response to an immunogen (e.g., an infectious agent, or a transplanted cell or tissue) and inhibition of a humoral immune response to an immunogen. Examples of disorders in which immunosuppression can be desirable include autoimmune disorders, transplant rejection disorders (e.g., rejection of a solid tissue or bone marrow transplant), development of an immune response to an implanted device (e.g., a stent or a heart valve), immune hypersensitivity, and anaphylaxis.

In another embodiment, a compound according to the present invention is used to treat a tumor, including solid tumors such as bladder, breast, colon, liver, ovary, gastric, pancreas, prostate, renal, retinoblastomas, melanoma, fibrosarcoma, or osteosarcoma. In another embodiment, a compound of the present invention is used to treat a leukemia or lymphoma, such as promyelocytic leukemia, acute lymphoblastic, chronic myelogenous leukemia, T cell lymphoma, cutaneous T cell lymphoma, Burkitt's B cell lymphoma, and B cell lymphoma. In another embodiment, a compound of the present invention is used to treat a cancer or tumor represented by a cell line shown to be inhibited by the compound.

The tamandarin analogs and fragments described herein can be administered in vitro to a cell or tissue (e.g., a cultured cell or tissue, or a cell or tissue harvested from one animal prior to introduction into the same or a different animal). Alternatively, the agents can be administered to the cell or tissue in vivo by administering the agent or a pharmaceutical composition comprising the agent to an animal (e.g., a mammal such as a human) that comprises the cell or tissue.

In one embodiment of the methods described herein, a tamandarin analog described herein and having an enzyme-cleavable group attached thereto is administered to an animal. In one embodiment, upon cleavage of the enzyme-cleavable group, the compound is transformed from an inactive (or less active) form to an active (or more active) form. Thus, the tamandarin analog can be selectively activated at a body location at which the enzyme activity occurs.

The enzyme which is used to cleave a tamandarin analog having an enzyme-cleavable moiety attached can be an enzyme which naturally occurs at a body location in an animal. Alternatively, the enzyme can be provided to the animal, for example as a composition comprising the enzyme or a nucleic acid which encodes the enzyme. As another example, the enzyme can be coupled (e.g., covalently, using a cross-linking agent or by expression as an enzyme-antibody fusion protein) with an antibody that specifically binds with a tissue (e.g., cancerous cells such as leukemic cells or cells of a solid tumor) at a body location in the animal, and the antibody-enzyme complex can be administered to an animal. Administration of a tamandarin analog having an attached enzyme-cleavable group to the same animal results in preferential activation of the compound at the tissue or body location. The physiological effect of the compound can thereby be localized at the tissue or body location, and any side effect attributable to the activated compound can thereby be reduced or minimized.

The compounds of the present invention may be administered in an effective amount within the dosage range of about 0.01 mg/kg to about 300 mg/kg, preferably between 0.1 mg/kg to 100 mg/kg body weight, more preferably from 0.1 mg/kg to 10 mg/kg body weight. A compound of the present invention may be administered in a single daily dose, or the total daily dosage may be administered in divided doses of two, three, or four times daily. The exact dosage and frequency of administration depends on the particular compound of Formula I, IA, or II used, the particular condition being treated, the severity of the condition being treated, the age, weight, and general physical condition of the particular patient as well as other medication the individual may be taking, as is well known to those skilled in the art. The dosages may be varied depending upon the requirements of the patient, the severity of the condition being treated, and the compound being employed.

In all cases of administration, it is understood that the compound of Formula I, IA, or II can be administered as a pharmaceutical composition comprising said compound and a pharmaceutically acceptable excipient, as described herein. Alternatively, the compound of Formula I, IA, or II may be administered as a pure material if appropriate.

In an additional aspect of the present invention, a compound of Formula I, IA, or II may be used alone or in combination with one or more additional pharmaceutical active agents (e.g., an anticancer agent, an antiviral agent.

In another embodiment, a compound of the invention is also useful in a drug discovery assay. A compound of Formula I, IA, or II may be used in an assay to determine the efficacy and/or potency of other compounds as anti-cancer, anti-viral, or immunosuppresive agents. These assays include in vivo and in vitro assays. The compounds of the present invention can be used as controls or can be used as lead compounds to discover new, useful compounds and drugs.

While still not being bound by any particular theory of operation, it is believed that the physiological activities attributable to the tamandarin analogs and fragments described herein result from one or more interactions between such analogs or fragments and at least one cellular component. This interaction(s) leads, directly or indirectly, to the observed cellular response. Accordingly, the invention encompasses use of a compound having the structure of Formula I, IA, or II to identify one or more cellular components which contributes to a disorder phenotype in an individual. Identification of such a cellular component can indicate an effective course of treatment for alleviating the disorder. Examples of compounds useful for this purpose include tamandarin analogs and fragments which have the structure of Formula I, IA, or U and which comprise a fluorescent substituent (e.g., part of $R^5$), photoreactive chemical moiety, or a moiety bound with a support.

Fluorescent and other detectably labeled tamandarin analogs described herein (as well as their physiologically active fragments) can be used to identify cells in which those analogs and fragments can exert their physiological effects. For example, cells which absorb or bind with a fluorescent compound having the structure of one of Formula I, IA, or II can be identified or isolated. Identification or isolation of such cells can be used to diagnose a disorder associated with the presence of such cells. Identification or isolation of these cells can also indicate which of the tamandarin analogs and fragments are efficacious for treating a disorder involving the cells.

Compounds of the present invention having a photoreactive moiety are useful as photoaffinity probes. Photoaffinity probes are useful for identifying, labeling, and/or modifying target proteins. Identification of the target protein is useful for understanding of disease and cellular processes. A photoaffinity probe of the present invention is for such a goal. Additionally, in another embodiment, a photoaffinity probe of the present invention is used to modulate or deactivate a target protein.

A support-bound tamandarin analog (or a support-bound fragment of a tamandarin analog which exhibits a corresponding physiological activity) can be used to identify cells which comprise, on their surfaces or elsewhere, receptor proteins, glycoproteins, and the like, which are capable of interacting or binding with the analog. As an example, a tamandarin analog having the structure of Formula I, IA, or II and attached to a support can, by virtue of its interaction with a particular cellular receptor, be used to identify or physically isolate cells of a particular type (e.g., tumor cells) which are characterized by the presence of the particular receptor.

In one embodiment, a method according to the present invention uses a compound selected from one or more of the individual embodiments listed above. In another embodiment, the method uses a compound is selected from the group consisting of a compound according to Formula I, IA, or II wherein.

$R^1$ and $R^2$ together form the alkyl ring of a proline residue, $R^3$ is benzyl, $R^4$ is $CH_3$, $R^5$ is (N-methyl-R-leucine)-S-proline-S-lactate, $R^6$ is a valine side chain, X is O, and Y is H (compound 36);

$R^1$ and $R^2$ together form the alkyl ring of a proline residue, $R^3$ is benzyl, $R^4$ is $CH_3$, $R^5$ is H, $R^6$ is a valine side chain, X is O, and Y is H;

$R^1$ and $R^2$ together form the alkyl ring of a proline residue, $R^3$ is benzyl, $R^4$ is $CH_3$, $R^5$ is H.HCl, $R^6$ is a valine side chain, X is O, and Y is H (compound 35);

$R^1$ and $R^2$ together form the alkyl ring of a proline residue, $R^3$ is benzyl, $R^4$ is $CH_3$, $R^5$ is Boc, $R^6$ is a valine side chain, X is O, and Y is TIPS (compound 34);

$R^1$ and $R^2$ together form the alkyl ring of a proline residue, $R^3$ is benzyl, $R^4$ is $CH_3$, $R^5$ is Boc, $R^6$ is a valine side chain, X is O, and Y is H;

$R^1$ and $R^2$ together form the alkyl ring of a proline residue, $R^3$ is 4-methoxybenzyl, $R^4$ is H, $R^5$ is (N-methyl-R-leucine)-S-proline-S-lactate, $R^6$ is a valine side chain, X is O, and Y is H (compound 62);

$R^1$ and $R^2$ together form the alkyl ring of a proline residue, $R^3$ is 4-methoxybenzyl, $R^4$ is H, $R^5$ is Boc, $R^6$ is a valine side chain, X is O, and Y is H (compound 61);

$R^1$ and $R^2$ together form the alkyl ring of a proline residue, $R^3$ is 4-methoxybenzyl, $R^4$ is H, $R^5$ is H, $R^6$ is a valine side chain, X is O, and Y is H;

$R^1$ and $R^2$ together form the alkyl ring of a proline residue, $R^3$ is 4-methoxybenzyl, $R^4$ is H, $R^5$ is (N-methyl-R-leucine)-S-proline-S-pyruvate, $R^6$ is a valine side chain, X is O, and Y is H (compound 64);

$R^1$ and $R^2$ together form the alkyl ring of a proline residue, $R^3$ is 4-methoxybenzyl, $R^4$ is H, $R^5$ is (N-methyl-R-leucine), $R^6$ is a valine side chain, X is O, and Y is H;

$R^1$ and $R^2$ together form the alkyl ring of a proline residue, $R^3$ is 4-methoxybenzyl, $R^4$ is H, $R^5$ is N-Cbz-N-methyl-R-leucine, $R^6$ is a valine side chain, X is O, and Y is H (compound 63);

$R^1$ and $R^2$ together form the alkyl ring of a proline residue, $R^3$ is 4-methoxybenzyl, $R^4$ is H, $R^5$ is H.HCl, $R^6$ is a valine side chain, X is O, and Y is H;

$R^1$ is H, $R^2$ is $CH_3$, $R^3$ is 4-methoxybenzyl, $R^4$ is $CH_3$, $R^5$ is (N-methyl-R-leucine)-S-proline-S-lactate, $R^6$ is a valine side chain, X is O, and Y is H (compound 75);

$R^1$ is H, $R^2$ is $CH_3$, $R^3$ is 4-methoxybenzyl, $R^4$ is $CH_3$, $R^5$ is Boc, $R^6$ is a valine side chain, X is O, and Y is H (compound 74);

$R^1$ is H, $R^2$ is $CH_3$, $R^3$ is 4-methoxybenzyl, $R^4$ is $CH_3$, $R^5$ is H, $R^6$ is a valine side chain, X is O, and Y is H;

$R^1$ is $CH^3$, $R^2$ is $CH_3$, $R^3$ is 4-methoxybenzyl, $R^4$ is $CH_3$, $R^5$ is (N-methyl-R-leucine)-S-proline-S-lactate, $R^6$ is a valine side chain, X is O, and Y is H (compound 150);

$R^1$ is $CH_3$, $R^2$ is $CH_3$, $R^3$ is 4-methoxybenzyl, $R^4$ is $CH_3$, $R^5$ is Boc, $R^6$ is a valine side chain, X is O, and Y is H (compound 85);

$R^1$ is $CH^3$, $R^2$ is $CH_3$, $R^3$ is 4-methoxybenzyl, $R^4$ is $CH_3$, $R^5$ is H, $R^6$ is a valine side chain, X is O, and Y is H;

$R^1$ and $R^2$ together form the alkyl ring of a proline residue, $R^3$ is 2-naphthylmethyl, $R^4$ is $CH_3$, $R^5$ is (N-methyl-R-leucine)-S-proline-S-lactate, $R^6$ is a valine side chain, X is O, and Y is H (compound 93);

$R^1$ and $R^2$ together form the alkyl ring of a proline residue, $R^3$ is 2-naphthylmethyl, $R^4$ is $CH_3$, $R^5$ is Boc, $R^6$ is a valine side chain, X is O, and Y is H (compound 92);

$R^1$ and $R^2$ together form the alkyl ring of a proline residue, $R^3$ is 2-naphthylmethyl, $R^4$ is $CH_3$, $R^5$ is H, $R^6$ is a valine side chain, X is O, and Y is H;

$R^1$ and $R^2$ together form the alkyl ring of a proline residue, $R^3$ is 4-methoxybenzyl, $R^4$ is $CH_3$, $R^5$ is (N-methyl-R-leucine)-S-proline-S-lactate, $R^6$ is a valine side chain, X is NH, and Y is H;

$R^1$ and $R^2$ together form the alkyl ring of a proline residue, $R^3$ is 4-methoxybenzyl, $R^4$ is $CH_3$, $R^5$ is H, $R^6$ is a valine side chain, X is NH, and Y is H; and $R^1$ and $R^2$ together form the alkyl ring of a proline residue, $R^3$ is 4-methoxybenzyl, $R^4$ is $CH_3$, $R^5$ is Boc, $R^6$ is a valine side chain, X is NH, and Y is H;

and pharmaceutically acceptable salts thereof.

Methods of Preparation of Compounds

A further aspect of the present invention is a method of synthesizing a compound according to Formula I, IA, or II. The compound of Formula I, IA, or II can be synthesized according to the general method outlined in the following schemes and descriptions. Specific, non-limiting examples of the synthesis are provided in the Examples section below.

In reference to methods of making the analogs and fragments described herein, the substituents $R^1$, $R^2$, $R^3$, $R^4$, $R^5$, $R^6$, W, X, Y, and Z have the same meanings as used above.

As used in the present disclosure, a protection reaction can include any reaction whereby one or more chemical moieties are covalently (but reversibly) attached to one of a nitrogen atom, an oxygen atom, and a sulfur atom of a molecule. Such attachment prevents the atom or atoms from participating in non-desired chemical reactions, i.e., becoming covalently attached to other chemical moieties, and donating or accepting either of protons and electrons to other chemical moieties. A chemical moiety thus attached is referred to as "a protecting group." By way of example, the nitrogen atom of a compound such as D-valine, can be protected using a reagent such as carbobenzyloxy-succinimide (CBZ-succinimide). Use of this reagent in a standard protocol yields a protected D-valine, i.e., D-N-Cbz-valine. In this compound, the CBZ moiety acts as an amine protecting group, and the nitrogen atom to which it is attached cannot readily undergo additional chemical reactions. As an alternative example, the hydroxyl moiety of compound II can be protected using a reagent such as triisopropylsilyltriflate (TIPSOTt) to yield compound 13 (Example 1). In this compound, Y is a triisopropylsilyl (TIPS) moiety and acts as a hydroxyl protecting group, preventing chemical reactions with the oxygen atom to which this moiety is attached.

Protocols for performing protection reactions and comprehensive information about chemical moieties that can be used as protecting groups is known in the art and is found in references such as Green and Wuts (1991, Protective Groups in Organic Synthesis, Wiley, New York) or Bodansky (1993, Principles of Peptide Synthesis, Springer, Berlin).

Certain tamandarin analogs and fragments of the invention can be made by the synthetic pathway shown in Schemes 1 and 2.

Scheme 1

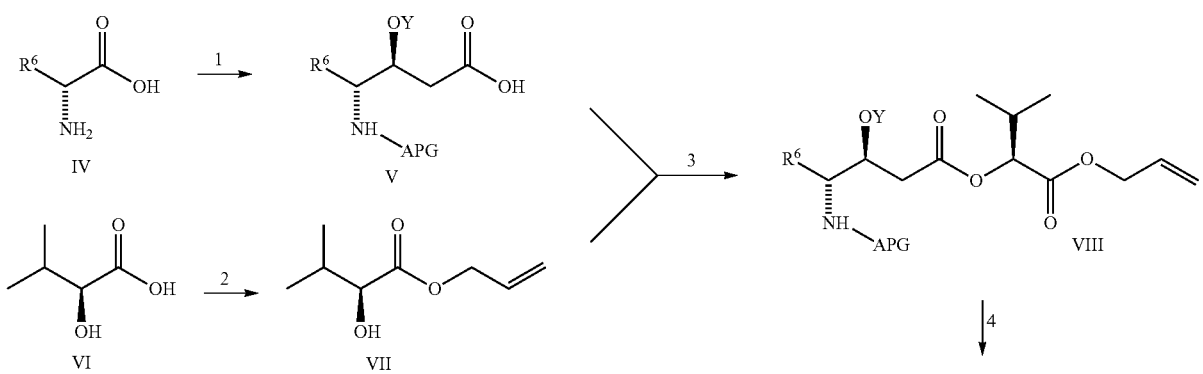

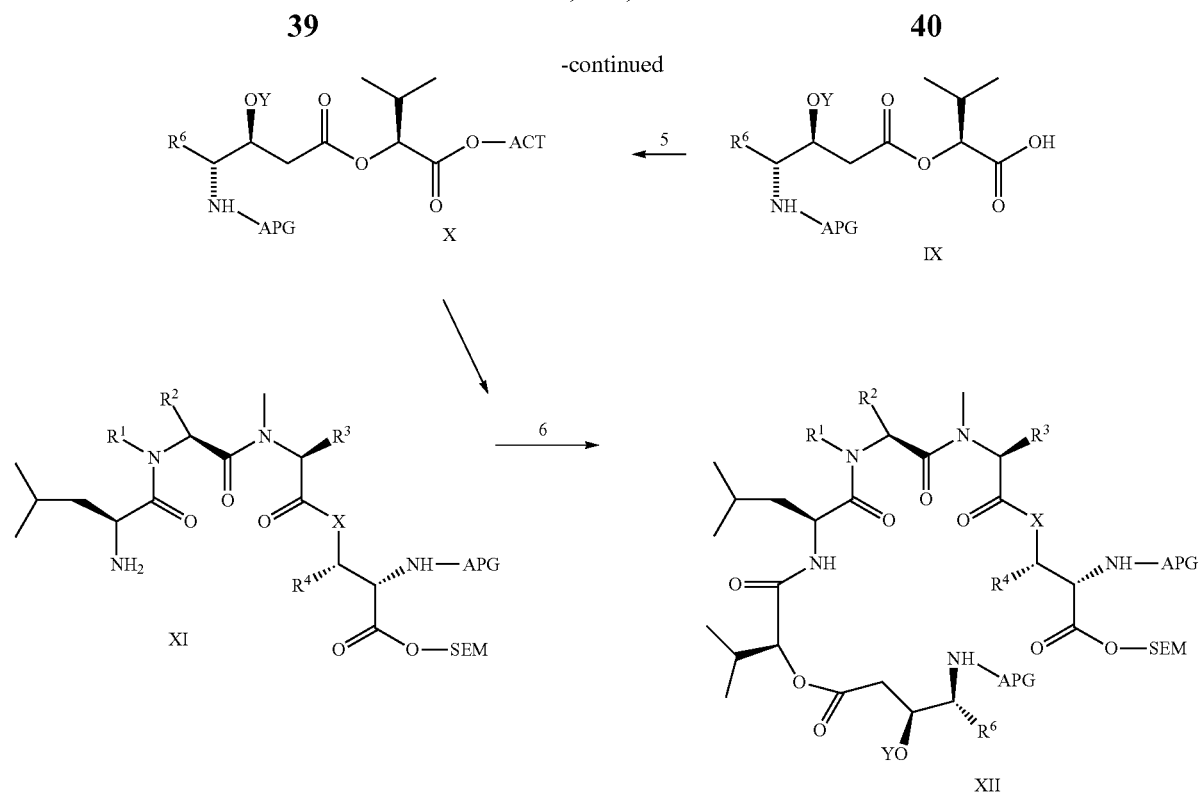
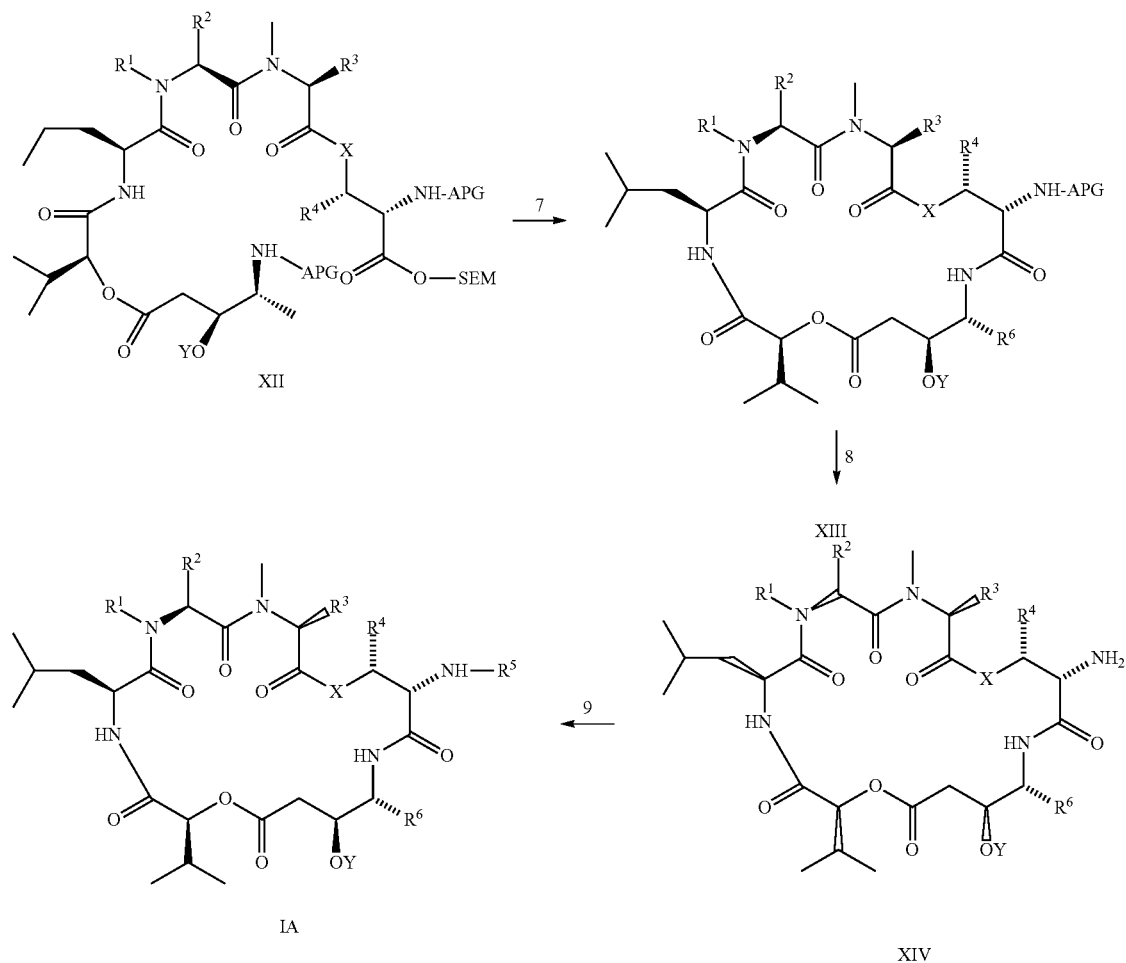
Scheme 2

In the process shown, a compound having the structure of Formula IV is converted to a compound having the structure of Formula V.

Such a series of reactions can include, but is not limited to, a protection reaction, an activation reaction, an esterification reaction, and an ester hydrolysis reaction. The amine group of Formula IV is preferably protected prior to performing the esterification and hydrolysis reactions. A specific example of making a compound having the structure of Formula V is given in Example 1. "APG" refers to an amine protecting group, such as, but not limited to, carbobenzyloxy (CBZ) moiety or tert-butyloxycarbonyl (BOC) moiety. Alternative amine protecting groups can also be used, as described herein and in the art.

An example of an activation reaction included in the method of making a compound having the structure of Formula V is depicted in Example 1. The activation step can involve a reagent such as pentafluorophenol (PFPOH). Esterification reactions which do not require an activated intermediate can also be employed to make a compound having the structure of Formula V.

Any method of ester hydrolysis known in the art that does not comprise harsh conditions which favor racemization can be used to make a compound having the structure of Formula V. By way of example, a compound having the structure of Formula V wherein the carboxy group is esterified to form the alkyl ester, e.g., methyl ester, can be hydrolyzed using a strong base in a solvent mixture. Reagents and conditions suitable for ester hydrolysis under milder conditions (i.e., including conditions which do not favor racemization) can be readily selected by one skilled in the art.

A compound having the structure of Formula VI can be esterified with, for example, allyl bromide (e.g., as described in Example 1), to yield a compound having the structure of Formula VII.

A compound having the structure of Formula V and a compound having the structure of Formula VII can be coupled (e.g., esterified) to yield a compound having the structure of Formula VIII (e.g., Step 3 of Scheme 1). Optionally, such a reaction can be performed using a catalyst, a coupling reagent, or an esterification reagent. Reagents and conditions useful for this type of reaction are known in the art and exemplified in Example 1. Tamandarin fragments having the structure of Formula VIII exhibit one or more of the pharmacological activities described herein.

A compound having the structure of Formula VIII can be hydrolyzed to yield a compound having the structure of Formula IX.

As described elsewhere herein, reaction conditions and reagents suitable for ester hydrolysis are known in the art, and can be readily applied by a skilled artisan. An example of this type of hydrolysis is depicted in Example 1. Tamandarin fragments having the structure of Formula IX exhibit one or more of the pharmacological activities described herein.

The carboxyl group of a compound having the structure of Formula IX can be activated to yield a compound having the structure of Formula X.

In Formula X, "ACT" refers to an activating group, such as a pentafluorophenyl (PFP) moiety. Another example of an activating group is an N-hydroxysuccinimide moiety. Chemical activation can be performed using reagents such as an activating reagent, a catalyst, an activating group donor, or the like. By way of example, compound 8, depicted in Example 2, is activated by covalent attachment of a PFP group to yield compound 18. Protocols for activating a compound in the manner disclosed herein are known in the art. Tamandarin fragments having the structure of Formula X exhibit one or more of the pharmacological activities described herein.

The activated compound having the structure of Formula X can be coupled with a third reactant having the structure of Formula XI to yield a compound having the structure of Formula XII. In Formulas XI and XII, SEM refers to 2-(trimethylsilyl)ethoxycarbonyl. An example of this reaction is depicted in Example 1, in which compound 24 is coupled with compound 18 to yield compound 25. The reagents and conditions necessary for preparation of a protected peptide such as compound 18 are described, for example, in Li et al., *J. Am. Chem. Soc.* 112: 7659-7672 (1990). Tamandarin analogs having the structure of Formula XII exhibit one or more of the pharmacological activities described herein.

A tamandarin analog having one or more of the pharmacological activities described herein can be made by removing one of the amino protecting groups and the carbonyl hydroxyl protecting group of a compound having the structure of Formula XII and cyclizing the compound to yield a compound having the structure of Formula XIII. This process is shown in Step 7 of Scheme 2.

An example of reactions of this type is shown in Example 1. Chemically deprotecting a compound such as one having the structure of Formula XII can be accomplished by reacting the compound with one or more reagents to remove a protecting group of the compound. Exemplary deprotection reactions are disclosed herein. Other protocols for deprotecting a compound are known in the art, and can be readily applied by a skilled artisan to deprotection of a compound having the structure of Formula XII. Cyclization of a deprotected compound otherwise having the structure of the Formula XII can be accomplished using methods known in the art for macrocyclization of peptides. For example, the macrocyclization conditions can be similar or identical to those used in the cyclization that yields compound 34, described in Example 2. Tamandarin analogs having the structure of Formula XIII exhibit one or more of the therapeutic activities described herein.

One or more of the protecting groups of a compound having the structure of the Formula XIII can be removed to yield a compound having the structure of Formula XIV. This deprotection is shown in Step 8 of Scheme 2. Tamandarin analogs having the structure of Formula XIV exhibit one or more of the therapeutic activities described herein.

Yet another active compound can be made by coupling a compound having the structure of Formula XIV and a reagent having the moiety of $R^5$. This reaction is exemplified in Examples 1-4. The $R^5$ substituent group can comprise an enzyme cleavable moiety, preferably at or near the distal end thereof (relative to the macrocycle). Such a moiety can be cleavable by an enzyme, for example, a carboxypeptidase, a β-lactamase, a β-galactosidase, a penicillin V-amidase, a cytosine deaminase, a nitroreductase, an alkaline phosphatase, a β-glucuronidase, and a catalytic antibody. An example of an $R^5$ moiety which comprises an enzyme-cleavable moiety is —(N-methyl)leucine-(S)proline-(S)lactate-(S)glutamine-(S)pyroglutamate. Other examples of enzyme-cleavable moieties are described herein. Other suitable reagents include those having the specific $R^5$ groups shown above wherein the open valence is replaced by a functional group, e.g., OH, such that the moiety contains a functional group, e.g., COOH, suitable for coupling with the amine of the macrocycle.

Other tamandarin analogs and fragments of the invention can be made by the synthetic pathway shown in Scheme 3.

Scheme 3

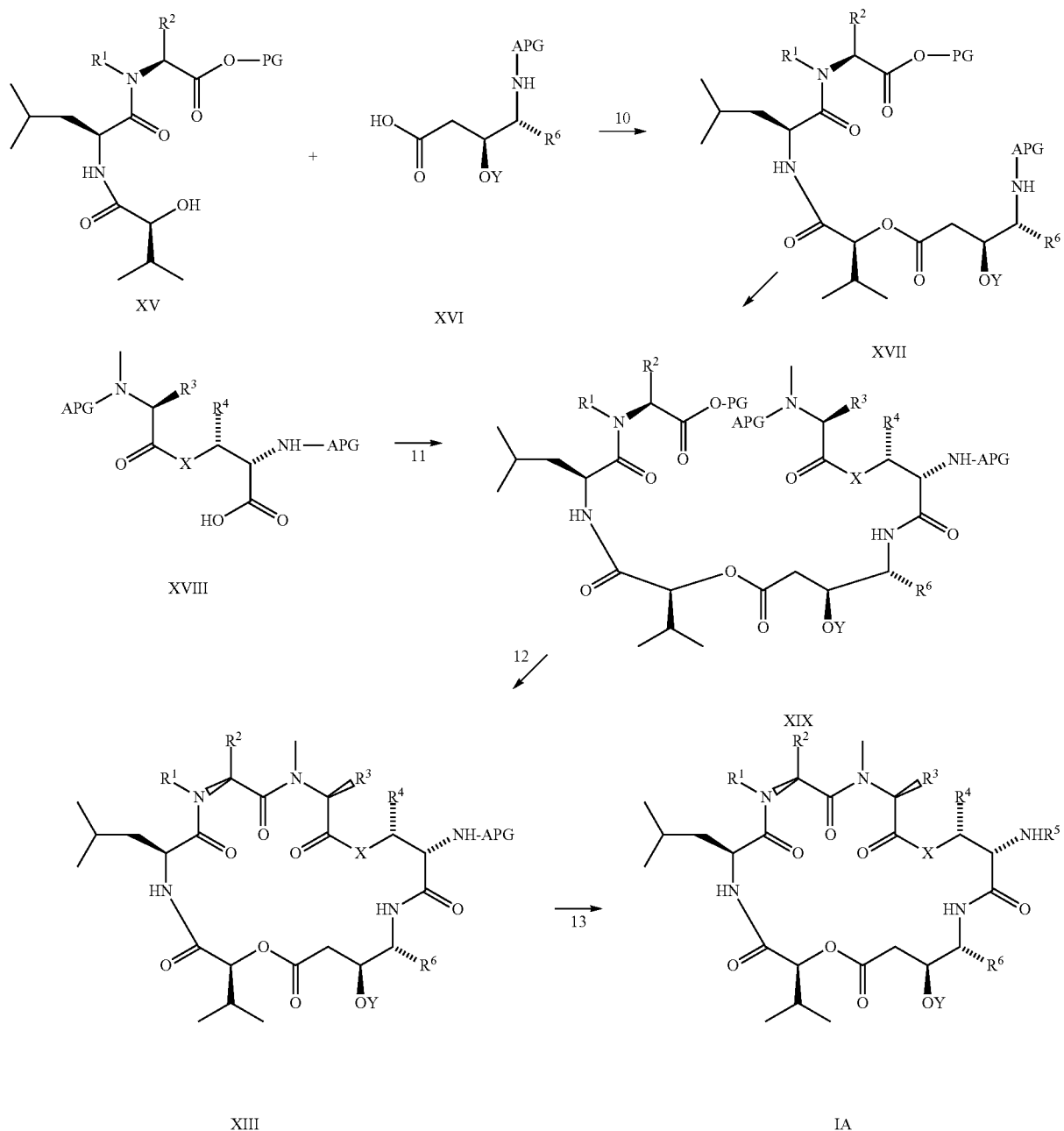

In Scheme 3, a compound of Formula XV is reacted with a compound of Formula XVI to form a compound of Formula XVII. Step 10 can be performed using suitable esterification conditions to form the compound of Formula XVII. The compound of Formula XVII is then condensed with a compound of Formula XVIII to form a compound of Formula XIX. The compound of Formula XIX is then reacted to form the macrocycle of Formula XIII. Step 12 comprises the deprotection of the amine and the carboxylate groups, and further comprises the macrocyclization reaction. The macrocycle of Formula XIII is deprotected (wherein $R^5$ is H) and then reacted with a suitable moiety to form a compound according to Formula I. It is noted that a compound of Formula XIII is within the scope of a Formula I.

When X is NH, such that the ester bond is replaced by an amide bond, the amide fragment containing $R^3$, $R^4$, and $R^5$ can be prepared as shown in Scheme 4.

Scheme 4

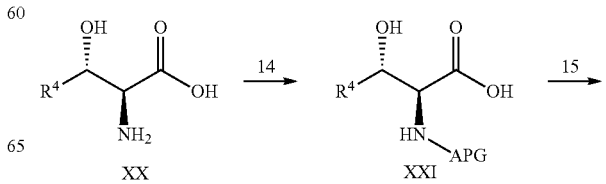

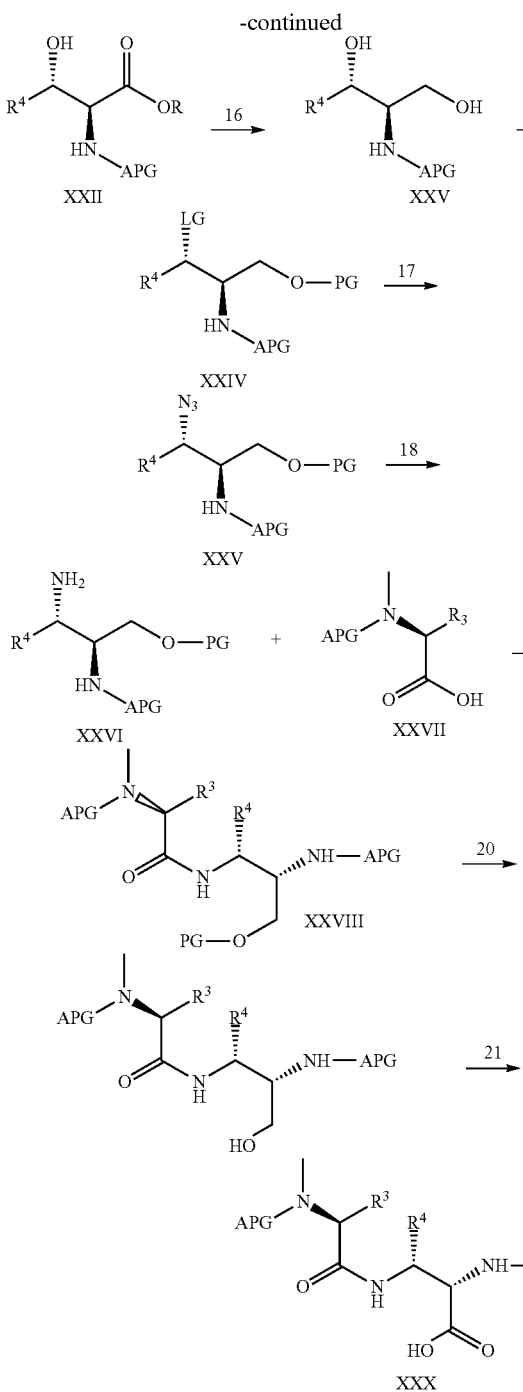

pylsilyl, and LG is an appropriate leaving group, such as mesyl or tosyl group. Preferably, Step 16 comprises two steps, wherein the first step is protecting the primary alcohol and the second step is converting the secondary alcohol to a suitable leaving group. The compound of Formula XXIV is then reacted with an azide compound, such as $NaN_3$, to form a compound of Formula XXV. The compound of Formula XXV is then reduced under suitable conditions, e.g., $H_2$ and Pd on carbon in ethanol, to yield an amine of Formula XXVI. Condensation of the amine of Formula XXVI with an acid for Formula XXVII under suitable conditions yields an amide of Formula XXVIII. The formation of the amide bond may be catalyzed with a suitable coupling reagent(s), for example, DCC, HOBt, and NMM. The amide of Formula XXVIII is then deprotected to yield an alcohol of Formula XXIX, which is oxidized to form the acid of Formula XXX. Suitable reagents and conditions for performing Steps 20 and 21 are well known in the art. The compound of Formula XXX is then used in place of the compound of Formula XVIII shown in Scheme 3 to prepare a compound according to Formula IA wherein X is NH.

A compound according to Formula I is prepared using a method analogous to that used for preparing the compounds of Formula IA described herein. When Z is C(O)—CH(CH$_3$)—C(O) and W is O or NH, a suitable HIP-isostatine moiety can be used in place of a compound of Formula X in Scheme 1. Suitable HIP-isostatine moieties are known. See, e.g., Pfizenmeyer et al., *Bioorg. Med. Chem. Lett.* 8:3653-3656 (1998).

Variation of the substituents of the tamandarin analogs and fragments may require slight modifications in the general methods described herein. It is understood that the invention includes such modifications, as they could be readily designed by one of ordinary skill in the art of synthetic chemistry.

$^1$H-NMR, $^{13}$C-NMR, IR, and MS spectra were recorded according to standard procedures. Significant peaks are tabulated in the order: number of protons, multiplicity (s, singlet; d, doublet; t, triplet; q, quartet; m, multiplet; br s, broad singlet) and coupling constant(s) in Hertz.

EXAMPLES

Example 1

Total Synthesis of Tamandarin B

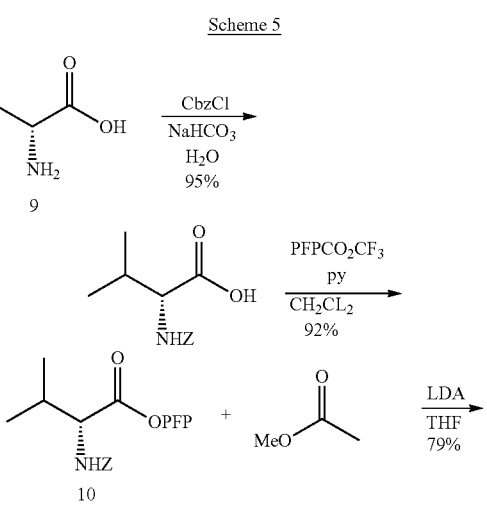

In Scheme 4, a compound of Formula XX is first reacted with a suitable amine protecting group to form a compound of Formula XXI. For example, reaction 14 can use (Boc)$_2$O and NaOH in dioxane. A compound of Formula XXI is then esterified to form a suitable ester of Formula XXII. A suitable ester includes an alkyl ester, such as a methyl ester. The ester may be formed by reacting the compound of Formula XXI with an alkyl halide, such as methyl iodide, and a suitable base, such as KHCO$_3$. The ester is then reduced to form an alcohol of Formula XXIII. The reduction can be carried out using standard conditions and reagents, such as NaBH$_4$. The compound of Formula XXIII is then converted to a compound of Formula XXIV, wherein PG is a suitable protecting group, such as tert-butyldimethylsilyl, trimethylsilyl, or triisopro-

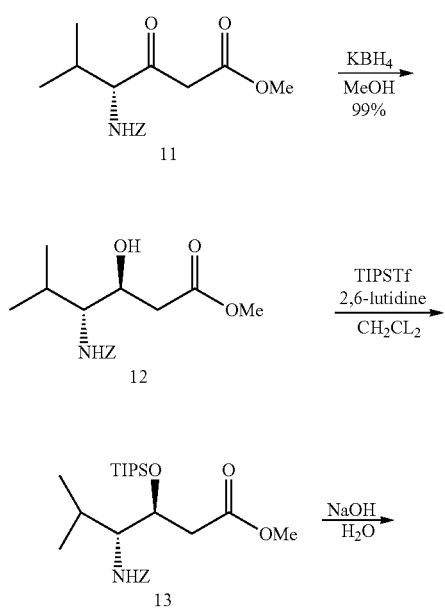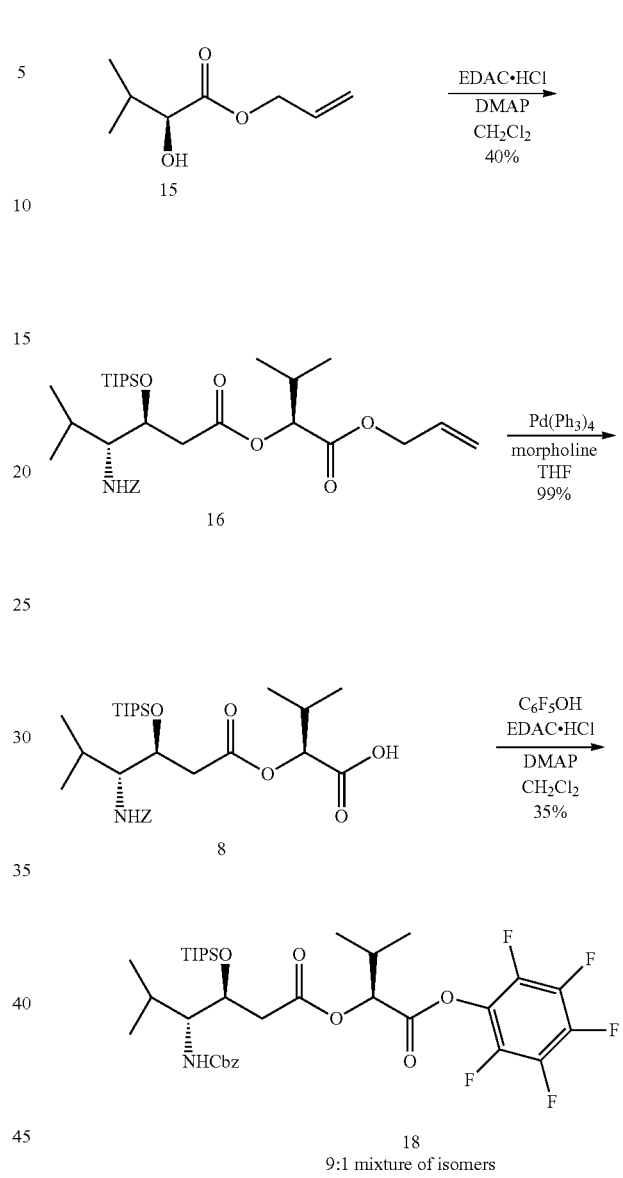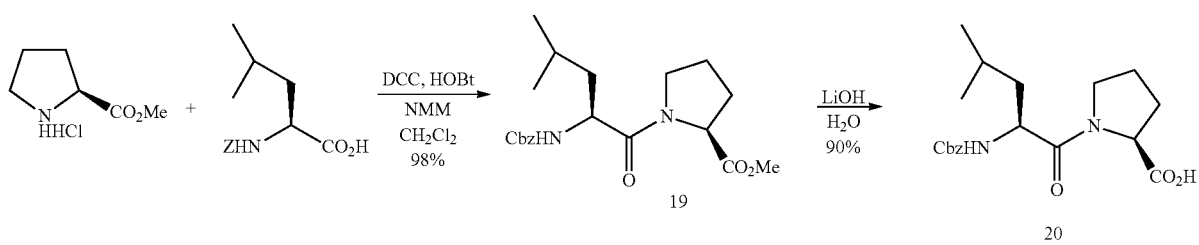

-continued
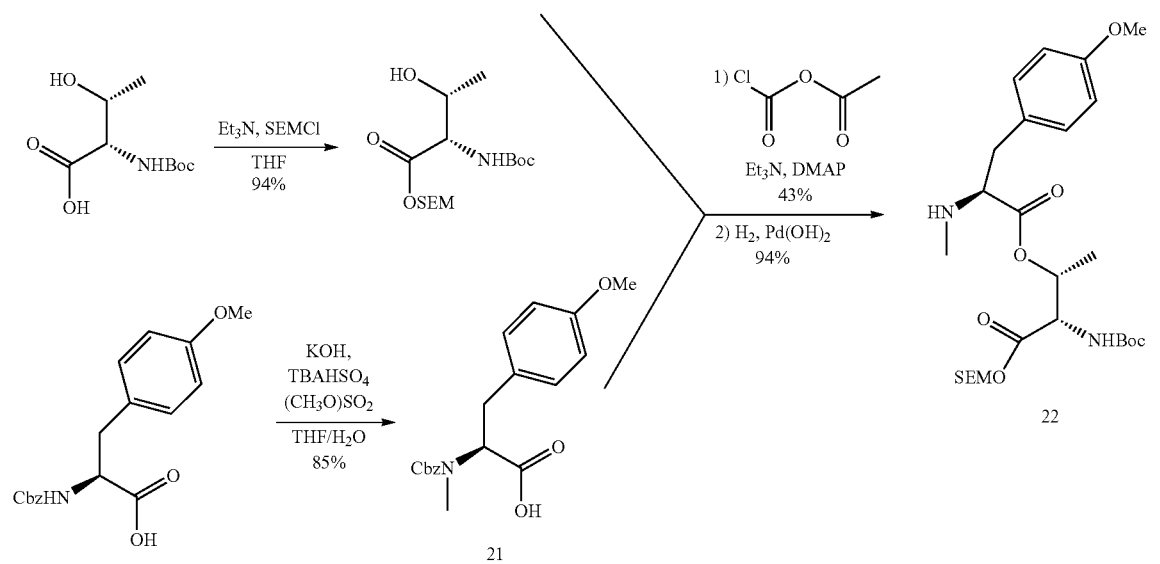
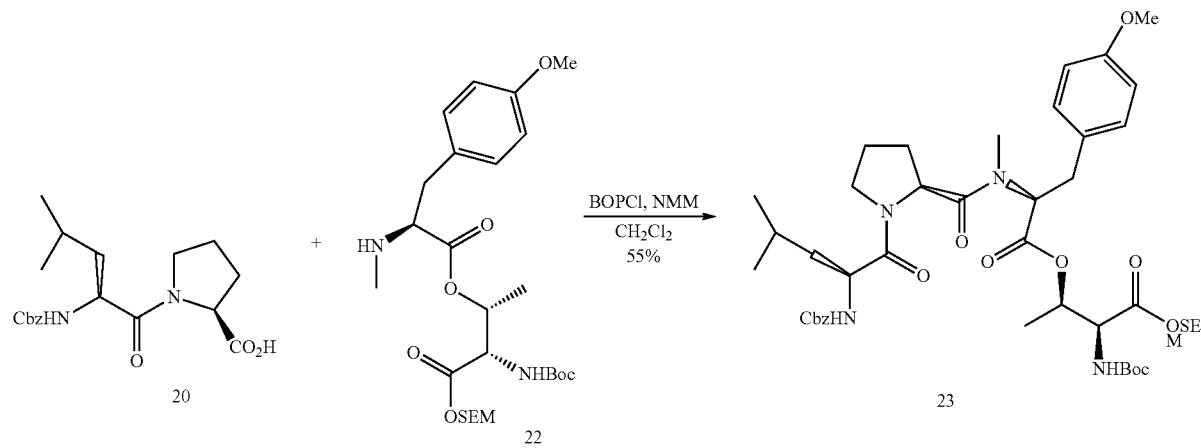
Scheme 8
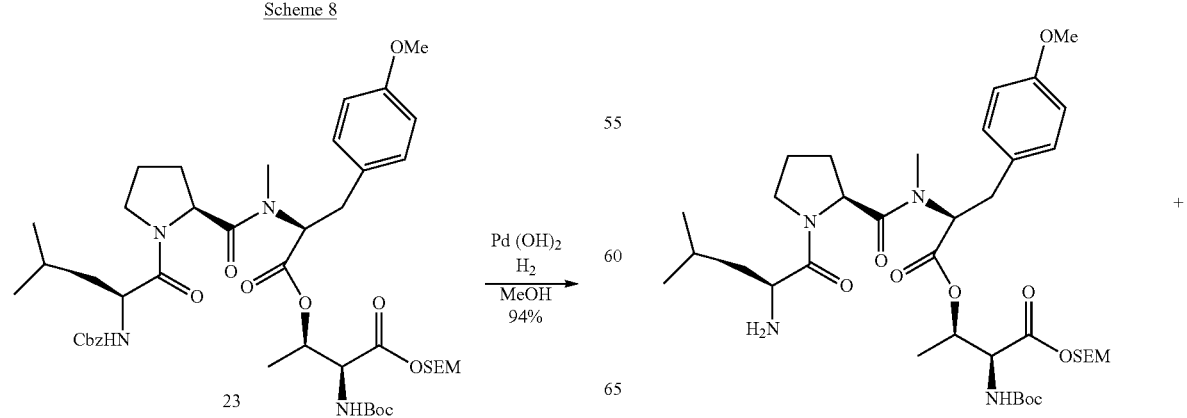

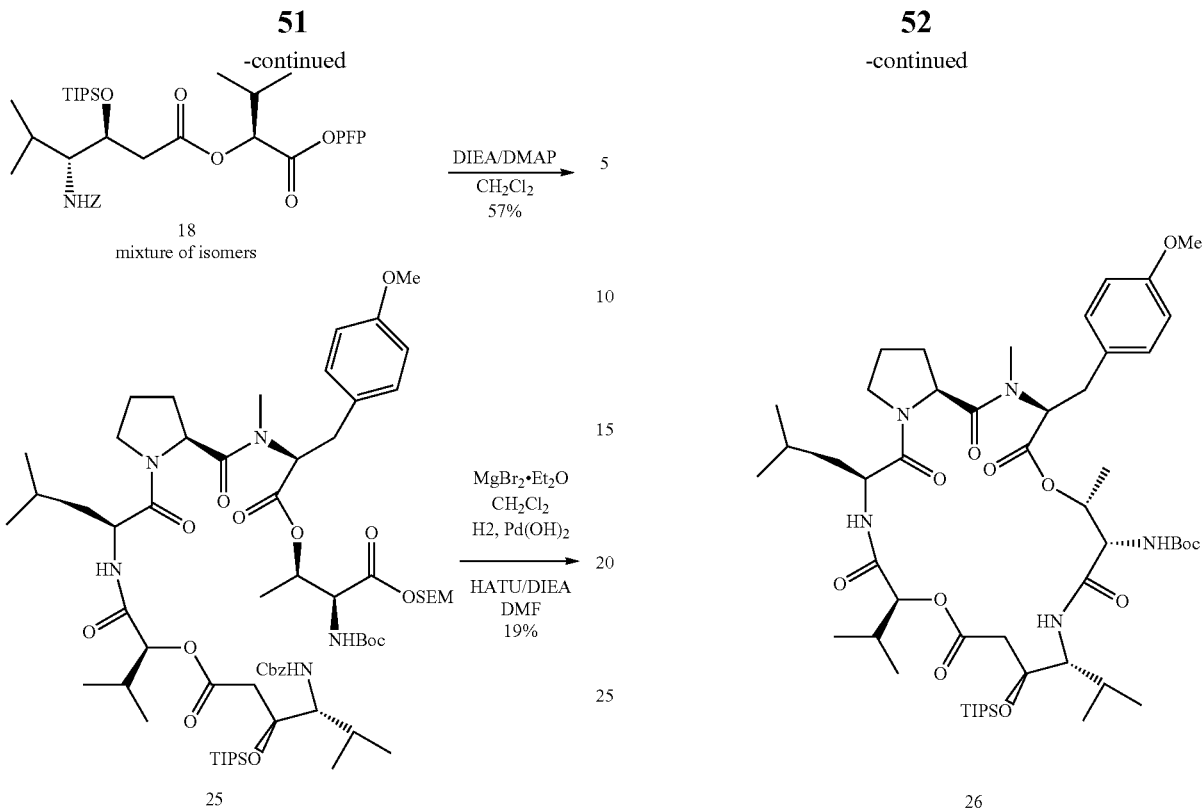
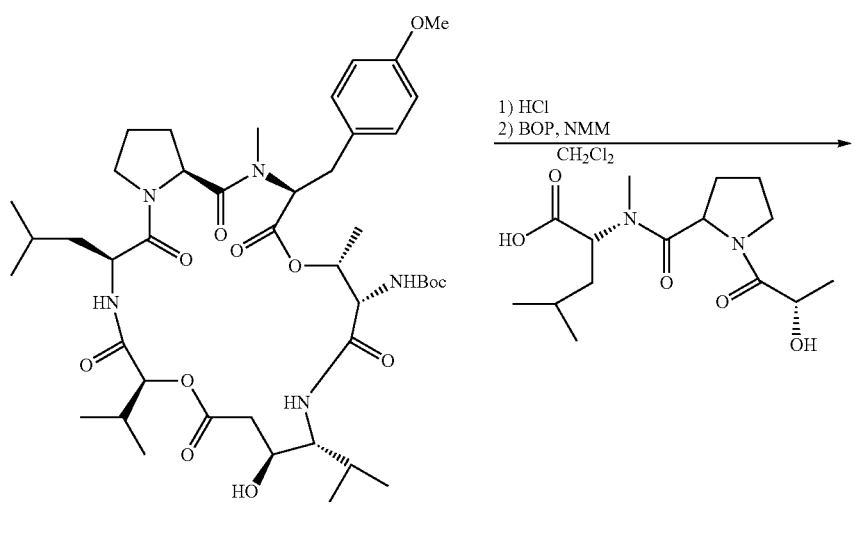
Scheme 9

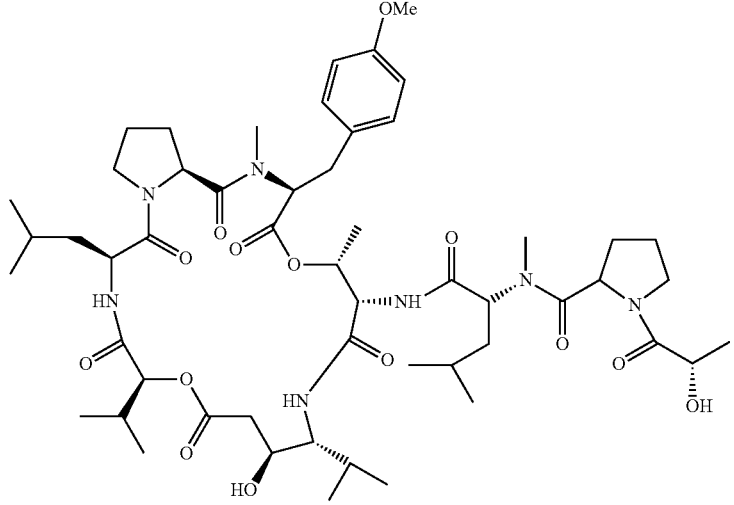

D-N-Cbz-Valine pentafluorophenyl (PFP) Ester (10): D-N-Cbz-Valine (9.8 g, 39.0 mmol) was dissolved in CH$_2$Cl$_2$ (100 mL) and cooled to 0° C., followed by the addition of pyridine (3.4 mL, 42.9 mmol,) and PFP-trifluoroacetate (4.08 mL, 46.8 mmol). The solution was stirred 1 h at room temperature and quenched with NH$_4$Cl (50 mL, sat). The organic layer was washed with 5% HCl (100 mL), NaHCO$_3$ (100 mL, sat), dried (Na$_2$SO$_4$), filtered and the solvent evaporated. The resulting PFP ester 10 was obtained as a colorless oil (15.8 g, 92%) and used directly in the next step. This compound showed identical $^1$H-NMR as that reported in ref 23. $^1$H-NMR (500 MHz, CDCl$_3$): 1.01 (d, J=6.9 Hz, 3H), 1.08 (d, J=6.9 Hz, 3H) 2.33-2.41 (m, 1H), 4.63-4.70 (m, 1H), 5.15 (s, 2H), 5.22 (d, J=7.8 Hz, 1H), 7.30-7.41 (m, 51-1).

(4R)-4-Benzyloxycarbonylamino-5-methyl-3-oxo-hexanoic Acid Methyl Ester (11): To a solution of PFP ester 10 (6 g, 14.4 mmol) in anhydrous THF (30 mL), cooled to −78° C., a solution of lithium enolate of methyl acetate was added. The enolate was prepared by addition of methyl acetate (4.12 mL, 50.3 mmol) to a solution of LDA (51.8 mmol in 50 mL of anhydrous TIE') at −78° C. and the resulting solution was stirred for 1 h. The reaction mixture was stirred for 45 min more at the same temperature, and quenched with NH$_4$Cl (50 mL) at −78° C. After warming to room temperature, the solution was diluted with EtOAc (mL). The organic layer was separated and washed with 10% HCl (100 mL), 5% NaHCO$_3$ (100 mL) and NaCl (100 mL, sat), dried (Na$_2$SO$_4$), filtered and concentrated. The crude oil was purified by column chromatography (silica gel, EtOAc/Hexanes 1/9) to yield the methyl ester 11 (2.8 g, 64%) as colorless oil. $^1$H-NMR (500 MHz, CDCl$_3$): 0.80 (d, J=6.8 Hz, 3H), 1.01 (d, J=6.8 Hz, 3H), 2.20-2.29 (m, 1H), 3.51 (d, J=11.8 Hz), 3.55 (d, J=17.7 Hz), 3.70 (s, 3H), 4.41 (q, J=4.4 Hz, 1H), 5.09 (s, 2H), 5.32 (d, J=12.0 Hz, 1H), 7.29-7.39 (m, 5H).

(3S,4R)-4-Benzyloxycarbonylamino-3-hydroxy-5-methylhexanoic Acid Methyl Ester (12): To a solution of methyl ester 11 (2.8 g, 9.15 mmol) in HPLC MeOH (30 mL), cooled to −78° C., potassium borohydride (1.72 g, 32 mmol) was added in portions. The reaction mixture was stirred at −78° C. for 10 min, warmed to −20° C. for 30 min and then to 0° C. for 10 min. The reaction was quenched with acetic acid to pH 7 and extracted with CH$_2$Cl$_2$ (3×50 mL). The organic layer was washed with NaHCO$_3$ (50 mL, sat), NaCl (50 mL, sat), dried (Na$_2$SO$_4$), filtered and evaporated. The alcohol 12 was obtained as a colorless oil (2.7 g, 98%) and used directly in the next step. $^1$H-NMR (500 MHz, CDCl$_3$): 0.87 (d, J=6.7 Hz, 3H), 0.94 (d, J=6.7 Hz, 3H), 2.10-2.19 (m, 1H), 2.47 (dd, J=16.7 and 9.1 Hz), 2.58 (dd, J=16.7 and 2.9 Hz, 1H), 3.11-3.20 (m, 1H), 3.56-3.63 (m, 1H), 3.68 (s, 3H), 3.90-3.98 (m, 1H), 4.64 (d, J=7.9 Hz, 1H), 5.09 (s, 2H), 7.30-7.39 (m, 5H).

(3S,4R)-4-Benzyloxycarbonylamino-5-methyl-3-(triisopropyl-silanyloxy)hexanoic Acid Methyl Ester (13): To a solution of the crude alcohol 12 (2.7 g, 9.1 mmol) in CH$_2$Cl$_2$ (10 mL) under argon, cooled to 0° C., 2,6-lutidine (2.6 mL, 22.7 mmol) and triisopropylsilyl triflate (3.6 mL, 13.6 mmol) were added. The reaction mixture was stirred at 0° C. for 30 min and then at room temperature for 2 h and diluted with CH$_2$Cl$_2$ (25 mL). The organic layer was separated and washed with 10% HCl (50 mL), NaHCO$_3$ (50 mL, sat) and NaCl (50 mL, sat), dried (Na$_2$SO$_4$), filtered and concentrated. The crude oil was purified by column chromatography (silica gel, diethyl ether/hexanes 2:98 to 15:85) to yield 13 (2.9 g, 70%) as colorless oil. $^1$H-NMR (500 MHz, CDCl$_3$): 0.88 (d, J=6.8 Hz, 3H), 0.92 (d, J=6.7 Hz, 3H), 1.01-1.07 (m, 2H), 1.97-2.04 (m, 1H), 2.53 (dd, J=15.3 and 4.7 Hz, 1H), 2.60 (dd, J=15.2 and 7.5 Hz, 1H), 3.57 (s, 3H), 3.59-3.65 (m, 1H), 4.34-4.40 (m, 1H), 4.78 (d, J=10.3 Hz, 1H), 5.06-5.09 (m, 2H), 7.27-7.35 (m, 5H).

(3S,4R)-4-Benzyloxycarbonylamino-5-methyl-3-(triisopropyl-silanyloxy)hexanoic Acid (14): To a solution of 13 (2.2 g, 4.7 mmol) in 50 mL of THF/MeOH (1:1), cooled to 0° C., 1N NaOH solution (55 mL, 32 mmol) was added. The reaction was stirred at 0° C. for 2 h and then overnight at rt. The reaction mixture was concentrated and diluted with H$_2$O (20 mL), cooled to 0° C., acidified to pH 2 with 1N KHSO$_4$ solution and extracted with EtOAc (3×20 mL). The combined organic layers were washed with NaCl (50 mL, sat), dried (Na$_2$SO$_4$), filtered and evaporated. The resulting acid 14 was obtained as a colorless oil (1.76 g, 86%) and used directly in the next step. $^1$H-NMR (500 MHz, CDCl$_3$): 0.86 (m, 3H), 0.95 (d, J=6.7 Hz, 3H), 1.04-1.14 (m, 21H), 1.90-2.00 (m, 1H), 2.52-2.72 (m, 2H), 3.60-3.62 (m, 1H), 4.28-4.36 (m, 1H), 5.02 (d, J=10.4 Hz, 1H), 5.07-5.13 (m, 3H), 7.25-7.35 (m, 5H).

(2S)-{1-(2S,3R)-[3-Benzyloxycarbonylamino-2-(triisopropyl-silaniloxy)hexyl]vinyloxy}-3-methylbutyric acid Allyl Ester (16): To a solution of acid 14 (1.76 g, 3.89 mmol) in $CH_2Cl_2$ (20 mL), cooled to 0° C., α-hydroxyisovaleric acid allyl ester 15 (615 mg, 3.89 mmol), EDAC HCl (820 mg, 4.20 mmol) and DMAP (94 mg, 0.77 mmol) were added sequentially. The reaction mixture was stirred at 0° C. for 1 h and then overnight at room temperature. The reaction was diluted with $CH_2Cl_2$ and the organic layer was washed with 10% HCl (50 mL), $NaHCO_3$ (50 mL, sat) and NaCl (50 mL, sat), dried ($Na_2SO_4$), filtered and concentrated. The crude oil was purified by column chromatography (silica gel, EtOAc/hexanes 9:1) to yield the allyl ester 16 (1.2 g, 52%) as colorless oil. $^1$H-NMR (500 MHz, $CDCl_3$): 0.88-0.99 (m, 12H), 1.00-1.10 (m, 21H), 1.96-2.05 (m, 1H), 2.17-2.25 (m, 1H), 2.65 (dd, J=15.8 and 5.3 Hz, 1H), 2.71 (dd, J=15.8 and 7.3 Hz, 1H), 3.62-3.72 (m, 1H), 4.40-4.45 (m, 1H), 4.57-4.63 (m, 2H), 4.79 (d, J=4.8 Hz, 1H), 4.88 (d, J=10.6 Hz, 1H), 5.07 (s, 2H), 5.20-5.23 (m, 1H), 5.28-5.32 (m, 1H), 5.83-5.91 (m, 1H), 7.26-7.38 (m, 5H).

(2S)-{1-(2S,3R)-[3-Benzyloxycarbonylamino-2-(triisopropyl-silaniloxy)hexyl]vinyloxy}-3-methylbutyric Acid Pentafluorophenyl Ester (18): To a solution of allyl ester 16 (1.2 g, 2.02 mmol) in dry THF (15 mL) $Pd(Ph_3)_4$ (231 mg, 0.20 mmol) and morpholine (1.7 mL, 20 mmol) were added, at room temperature. The mixture was stirred overnight and the reaction mixture was concentrated, diluted with $CH_2Cl_2$ (20 mL) and washed with 1N HCl (20 mL) and $H_2O$ (20 mL). The organic layer was dried ($Na_2SO_4$) filtered and concentrated to afford acid 17. The residue was dissolved in $CH_2Cl_2$ (5 mL), cooled to 0° C., followed by the sequential addition of PFPOH (384 mg, 2.09 mmol), EDAC.HCl (45 mg, 72.38 mmol) and DMAP (49 mg, 0.39 mmol). The reaction mixture was stirred at 0° C. for ½ h and then 4 h at room temperature. The reaction was diluted with $CH_2Cl_2$ and the organic layer was washed with 10% HCl (50 mL), 5% $NaHCO_3$ (50 mL) and NaCl (50 mL, sat), dried ($Na_2SO_4$), filtered and concentrated. The crude oil was purified by column chromatography (silica gel, EtOAc/hexanes 9/1) to yield pentafluorophenyl ester 18 (0.71 g, 50% two steps overall) as a colorless oil. $^1$H-NMR (500 MHz, $CDCl_3$): 0.89 (d, J=7.0 Hz, 3H), 0.92 (d, J=7.0 Hz, 3H), 1.02-1.06 (m, 21H), 1.06-1.11 (m, 6H), 2.00-2.08 (m, 1H), 2.31-2.40 (m, 1H), 2.60-268 (dd, J=15.8 and 4.8 Hz, 1H), 2.77 (dd, J=15.8 and 7.9 Hz, 1H), 3.63-3.70 (m, 1H), 4.40-4.45 (m, 1H), 4.79 9d, J=10.3 Hz, 1H), 4.98-5.03 (m, 2H), 5.04-5.08 9m, 1H), 7.26-7.34 (m, 5H).

L-Cbz-N-Leucyl-L-proline Methyl Ester (19): To a solution of L-Cbz-leucine (902 mg, 3.40 mmol) and L-proline methyl ester hydrochloride (563 mg, 3.40 mmol) in dry $CH_2Cl_2$ (10 mL), cooled to 0° C., dicyclohexyl carbodiimide (DCC) (912 mg, 4.42 mmol), 1-hydroxybenzotriazole (HOBt) (551 mg, 4.08 mmol) and N-methylmorpholine (NMM) (2.6 mL, 13.6 mmol) were added. After 1 h the reaction was warmed to room temperature and stirred overnight. The mixture was diluted with ether (10 mL) and filtered. The filtrate was diluted with EtOAc (25 mL) and washed with 10% HCl (100 mL), $NaHCO_3$ (100 mL, sat) and NaCl (100 mL, sat) solutions. The organic layer was dried ($Na_2SO_4$) and the solvent evaporated. The crude oil was purified by column chromatography (silica gel, EtOAc/Hexanes 2/8) to yield L-Cbz-N-leucyl-L-proline methyl ester (1.24 g, 98%) as white foam. $^1$H-NMR (500 MHz, $CDCl_3$): 0.94 (d, J=6.6 Hz, 3H), 0.99 (d, J=6.5 Hz, 3H), 1.50-1.65 (d, J=6.5 Hz, 2H), 1.73-1.79 (m, 1H), 1.94-2.22 (m, 4H), 3.57-3.78 (m, 2H), 3.70 (s, 3H), 4.50-4.55 (m, 2H), 5.03-5.09 (m, 2H), 5.33 (d, J=8.8 Hz, 2H), 7.28-7.34 (m, 15H).

L-Cbz-N-Leucyl-L-proline (20): To a solution of dipeptide ester 19 (887 mg, 2.36 mmol) in THF (20 mL), cooled to 0° C., a solution of LiOH (198 mg, 4.72 mmol) in water (20 mL) was added dropwise. The reaction was warmed to room temperature and stirred overnight. The resulting solution was concentrated under reduced pressure and extracted with ether. The aqueous layer was acidified to pH 2 with 50% HCl and extracted with EtOAc (3×20 mL). The organic layer was dried ($Na_2SO_4$) and the solvent evaporated to yield L-Cbz-N-Leucyl-L-proline 20 (774 mg, 90%) as a white foam. This compound showed identical $^1$H-NMR as that reported in ref 24. $^1$H-NMR (500 MHz, $CDCl_3$): 0.92 (d, J=6.5 Hz, 3H), 0.96 (d, J=6.5 Hz, 3H), 1.43-1.58 (m, 2H), 1.71-1.76 (m, 1H), 1.99-2.23 (m, 4H), 3.55-3.58 (m, 1H), 3.75-3.78 (m, 1H), 4.51-4.58 (m, 2H), 5.03-5.09 (m, 2H), 7.28-7.34 (m, 15H).

L-Cbz-N—O-Dimethyltyrosine (21): To a stirred solution of L-Cbz-Tyr (5.0 g, 15.8 mmol) in THF (84 mL), at 0° C., finely powered KOH (8.86 g, 158 mol) was added in portions, followed by the addition of tetrabutylammonium hydrogen sulfate (0.5 g, 10% by weight). Then, dimethyl sulfate (9.74 mL, 103 mmol) was added dropwise over 15 min. The reaction was stirred for an additional 30 min and $H_2O$ (50 mL) was added. After stirring 5 h at room temperature, 20% aqueous ammonium hydroxide solution was added (20 mL). The reaction was diluted with ether (100 mL), the aqueous layer was separated and the organic layer was extracted with saturated aq $NaHCO_3$ (2×40 mL). The combined aqueous layers were acidified to pH 1 with 1M $KHSO_4$ and extracted with EtOAc (2×200 mL). The organic layers were combined, dried ($Na_2SO_4$), filtered and concentrated. The resulting acid 21 (4.3 g, 85%) was obtained as a yellow oil and used in the next step without purification. $^1$H-NMR (500 MHz, $CDCl_3$): 2.78 and 2.84 (s, 3H), 2.92-3.06 (m, 1H), 3.21-3.30 (m, 1H), 3.76 (s, 3H), 4.80-4.90 (m, 1H), 5.00-5.10 (m, 2H), 6.65-6.79 (m, 2H), 7.00-7.09 (m, 2H), 7.24-7.33 (m, 5H).

L-Cbz-N,O-Dimethyltyrosine-O-L-N-Boc-threonine-SEM ester: To a solution of L-Cbz-N—O-dimethyltyrosine (21) (188 mg, 0.54 mmol) in $CH_2Cl_2$ (2 mL), cooled to 0° C., Boc-Thr-O-SEM (100 mg, 0.45 mmol) was added. To the resulting solution $Et_3N$ (165 μL, 1.18 mmol), DMAP (14 mg, 0.11 mmol) and isopropenyl chloroformate (60 μL, 0.54 mmol) were added. The reaction was stirred at 0° C. for 1 h, diluted with $Et_2O$ (10 mL) and washed with 10% HCl (10 mL), 5% $NaHCO_3$ (10 mL) and saturated NaCl (10 mL) solutions. The organic layer was dried ($Na_2SO_4$) and the solvent evaporated. The crude oil was purified by column chromatography (silica gel, EtOAc/Hexanes 10:1) to yield the dipeptide 22 (131 mg, 43%). $^1$H-NMR (200 MHz, $CDCl_3$): 0.01 (m, 9H), 0.92-0.96 (m, 2H), 1.23-1.29 (m, 3H), 1.44 and 1.43 (s, 9H), 2.72 and 2.79 (s, 3H), 2.81-2.98 and 3.17-3.21 (m, 2H), 3.67-3.72 (m, 2H), 3.76 (s, 3H), 4.20-4.50 (m, 2H), 4.60-4.78 (m, 1H), 5.03-5.11 (m, 2H), 5.25-5.43 (m, 2H), 6.74-6.78 (m, 2H), 6.97-7.06 (m, 2H), 7.22-7.33 (m, 5H).

L-N,O-Dimethyltyrosine-O-L-Boc-threonine-OSEM (22): To a solution of L-Cbz-N-methylphenylalanine-O-Boc-threonine-OSEM (231 mg. 0.34 mmol) in MeOH under argon, $Pd(OH)_2$ (23 mg) was added. The reaction was purged with $H_2$ and stirred overnight under a hydrogen atmosphere (1 atm). The mixture was filtered through Celite®. The filtrate was concentrated to yield compound 22 (174 mg, 94%) as a yellow oil. $^1$H-NMR (500 MHz, $CDCl_3$): 0.0 (s, 9H), 0.91 (t, J=8.2, 2H), 1.23 and 1.25 (d, J=5.6 Hz, 3H), 1.41 (s, 9H), 2.31 (s, 3H), 2.79 (s, 3H), 2.82 and 2.83 (dd, J=14.3 and 6.4 Hz), 3.45 (t, J=6.1 Hz, 1H), 3.64-3.67 (m, 2H), 4.48 and 5.23 (d, J=9.7 Hz), 5.02 (d, J=5.2 Hz, 2H), 6.75-6.78 (m, 2H), 6.92-7.05 (m, 2H).

L-Cbz-Leucyl-L-prolyl-L-N, O-Dimethyltyrosine-O-L-Boc-threonine-O-SEM (23): To a solution of L-Cbz-Leu-L-Pro-OH (98.4 mg, 0.27 mmol) in $CH_2Cl_2$ (2 mL), cooled to −15° C., BOP-Cl (69 mg, 0.27 mmol) was added, followed by the dropwise addition of NMM (30 μL, 0.27 mmol). A separate solution of L-N,O-dimethyltyrosine-O-L-Boc-threonine-O-SEM (147 mg, 0.27 mmol) in CH$_2$Cl$_2$ (2 mL) was cooled to −15° C. and added to the reaction followed by the addition of N-methylmorpholine (NMM) (30 μL, 0.54 mmol). The mixture was stirred 15 min at −15° C., 1 h at 0° C. and overnight at room temperature. The reaction mixture was diluted with EtOAc (15 mL) and washed with 10% HCl (10 mL), NaHCO$_3$ (10 mL, sat) and NaCl (10 mL, sat). The organic layer was dried (Na$_2$SO$_4$) and the solvent evaporated. The crude oil was purified by column chromatography (silica gel, EtOAc/Hexanes 3/7) to yield the tetrapeptide 23 (130 g, 55%) as pale yellow oil. $^1$H-NMR (500 MHz, CDCl$_3$): 0.00 (s, 9H), 0.67-0.87 (m, 2H), 0.89-1.00 (m, 6H), 1.19-1.21 (d, J=6.8 Hz), 1.36 (d, J=6.8 Hz, 3H), 1.46 (s, 9H), 1.54-1.99 (m, 7H), 2.72 (s), 2.73 (s, 3H), 2.91-3.00 (m, 1H), 3.05-3.15 (m), 3.50-3.55 (m, 1H), 3.66-3.89 (m, 4H), 3.75 (s, 3H), 4.25-4.33 (m, 1H), 4.41-4.61 (m, 2H), 4.67-4.68 (m, 1H), 4.62-4.75 (m, 1H), 4.95-5.01 (dd, J=8.5 and 3.2 Hz), 5.01-5.17 (m, 2H), 5.27-5.62 (m, 3H), 7.16-7.42 (m, 10H), 7.81 (m, 1H), 8.00 (m).

L-Leucyl-L-prolyl-L-N,O-Dimethyltyrosine-L-N-Boc-threonine-O-SEM (24): To a solution of L-Cbz-leucyl-L-prolyl-L-N-methylphenylalanine-O-L-Boc-threonine-OSEM (665 mg, 0.74 mmol) in MeOH (10 mL) under argon, Pd(OH)$_2$ (119 mg) was added. The reaction was purged with H$_2$ and stirred overnight under H$_2$ atmosphere (1 atm). The mixture was filtered through Celite. The filtrate was concentrated to yield the free amino tetrapeptide 24 (547 mg, 94%) as a colorless oil which was used in the next step without further purification. $^1$H-NMR (500 MHz, CDCl$_3$): 0.001 (s, 9H), 0.64-0.86 (m, 2H), 0.88-0.96 (m, 6H), 1.19-1.21 (d, J=6.3 Hz), 1.33-1.34 (d, J=6.3 Hz, 3H), 1.44 (s, 9H), 1.63-1.92 (m, 3H), 1.92-2.01 and 2.08-2.24 (m, 4H), 2.73 (s), 2.86-2.96 and 3.10-3.19 (m, 2H), 3.45-3.72 (m, 4H), 4.34-4.69 (m, 3H), 4.78-4.81 (dd, J=8.0 and 3.3 Hz, 1H), 5.01-5.10 (m, 1H), 5.17-5.52 (m) and 5.58-7.60 (m, 3H) 6.77-6.83 (m, 2H), 7.00-7.10 (m, 2H)

Tamandarin B Protected Linear Precursor (25): To a solution of the PFP ester 18 (285 mg, 0.39 mmol) in CH$_2$Cl$_2$ (1.5 mL), cooled to 0° C., was added DIEA (170 μL, 0.98 mmol) and the solution was stirred for 20 min, followed by the addition of amine 24 (292 mg, 0.39 mmol) in CH$_2$Cl$_2$ (1.5 mL) and DMAP (9.5 mg, 0.078 mmol). The reaction mixture was stirred at 0° C. for 1 h and then at it for an additional 1 h. The reaction was quenched with NH$_4$Cl (3 mL) and diluted with CH$_2$Cl$_2$ (10 mL). The organic layer was washed with 10% HCl (10 mL), 5% NaHCO$_3$ (10 mL) and NaCl (10 mL, sat), dried (Na$_2$SO$_4$), filtered and concentrated. The crude oil was purified by column chromatography (silica gel, EtOAc/Hexanes 9:1) to yield 25 (285 mg, 57%) as a colorless oil. $^1$H-NMR (500 MHz, CDCl$_3$): 0.008 (s, 9H), 0.73-0.83 (m, 2H), 0.85-0.92 (m, 9H), 0.92-1.08 (m, 21H), 1.45 (s, 4H), 1.13-2.19 (m, 11H), 2.43-2.46 (m, 1H) and 2.54-2.58 (m. 1H), 2.64 (s, 3H), 2.88 (s, 3H), 3.09-3.17 (m, 2H), 3.44-3.73 (m, 4H), 3.75 (s, 3H), 3.79-3.89 (m, 1H), 4.38-4.55 (m, 4H), 4.69-4.81 (m, 1H), 4.96-5.05 (m, 3H), 5.18-5.43 (m, 3H), 5.46-5.48 (d, J=6.0 Hz, 1H), 6.83 (m, 2H), 6.95-7.11 (m, 2H), 7.25-7.38 (m, 5H), 7.55-7.77 (m) and 8.85-8.87 (m, 2H).

Tamandarin B Protected Macrocycle (26): To a solution of the fully protected linear precursor 25 (350 mg, 0.27 mmol) dissolved in CH$_2$Cl$_2$ (5 mL), at 0° C., MgBr$_2$.Et$_2$O (210 mg, 0.81 mmol) was added. The reaction was stirred at 0° C. for 2 h and overnight at rt. The reaction was diluted with CH$_2$Cl$_2$ and the organic layer was washed with 10% HCl (10 mL) and NaCl (10 mL, sat), dried (Na$_2$SO$_4$), filtered and concentrated. The resulting acid (319 mg) was obtained as a white foam and used directly in the next step. To a solution of crude acid (319 mg) in MeOH (5 mL) under argon, Pd(OH)$_2$ (28 mg) was added. The reaction was purged with H$_2$ and stirred overnight under H$_2$ atmosphere (1 atm). The mixture was filtered through Celite. The filtrate was concentrated to yield the linear precursor (296 mg) as a white foam which was used directly in the next step. The crude amino acid linear precursor was dissolved in DMF (27 mL) and cooled to 0° C. HATU (123 mg, 0.32 mmol) was added followed by the dropwise addition of DIEA (141 μL, 0.81 mmol). The reaction mixture was stirred at 0° C. for 1 h and then overnight. The reaction mixture was concentrated in vacuo, diluted with EtOAc (10 mL) and washed 10% HCl (10 mL), 5% NaHCO$_3$ (10 mL) and NaCl (10 mL, sat), dried (Na$_2$SO$_4$), filtered and concentrated. The crude oil was purified by column chromatography (silica gel, EtOAc/Hexanes 5/1) to yield protected macrocycle 26 (50 mg, 19% three steps overall) as white foam. This compound showed identical $^1$H-NMR as that reported in ref 23. $^1$H-NMR (500 MHz, CDCl$_3$): 0.78-1.07 (m, 39H), 1.21-1.48 (m, 17H), 1.56-1.92 (m, 4H), 1.73-1.81 (m, 1H), 1.95-2.12 (m, 2H), 2.43-2.44 (m, 1H) and 3.11-3.17 (m, 1H), 2.52 (s, 3H), 2.89-3.00 (m, 1H), 3.30-3.32 (m, 1H), 3.49-3.52 (m, 1H), 3.60-3.62 (m, 1H), 3.66-3.70 (m, 1H), 3.77 (s, 3H), 4.14-4.19 (m, 1H), 4.37-4.43 (m, 1H), 4.46-4.48 (d, J=7.6 Hz, 1H), 4.55-4.86 (m, 1H), 4.88-4.92 (m, 1H), 6.82-6.83 (d, J=8.5 Hz, 2H), 7.06-7.07 (d, J=8.5 Hz, 2H), 7.41-7.48 (m, 2H).

Tamandarin B (2): To a solution of Boc protected macrocycle 26 (10 mg, 0.01 mmol) in HPLC EtOAc was added a solution of HCl in EtOAc. The resulting solution was stirred at room temperature for 2 h. The solution was concentrated and the residue diluted with CH$_2$Cl$_2$ and concentrated again to yield the hydrochloride salt (quantitative yield) as a white solid, which was used directly in the next step. To a mixture of the macrocycle amine salt (9 mg, 0.01 mmol) and side chain (6.1 mg, 0.015 mmol) in CH$_2$Cl$_2$ (0.50 mL) at 0° C. was added BOP (8.4 mg, 0.015 mmol) and NMM (6 μL, 0.05 mmol). After 30 min at 0° C., the reaction was stirred at rt overnight The reaction was treated with NaCl solution (2 mL, sat) and extracted with EtOAc (2×10 mL) The organic layers were washed with 10% HCl (5 mL), 5% NaHCO$_3$ (5 mL) and NaCl (5 mL, sat), dried (Na$_2$SO$_4$), filtered and concentrated. The crude oil (8 mg, 61%) was purified by HPLC.

Example 2

Synthesis of Phe$^5$ Tamandarin B

A phenylalanine analog of tamandarin B (Phe$^5$ Tamandarin B) was synthesized according to the method shown in Schemes 9 and 10.

Scheme 10

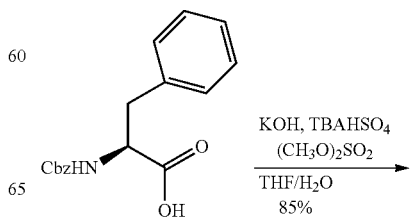

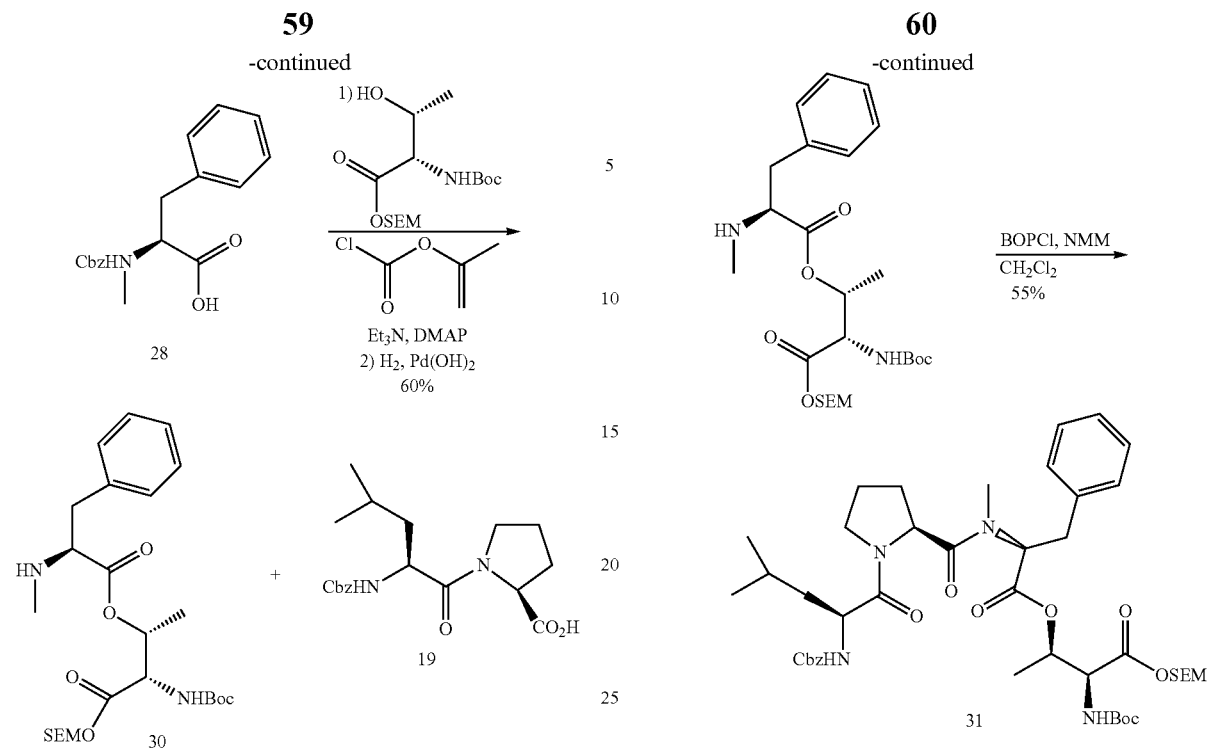
Scheme 11
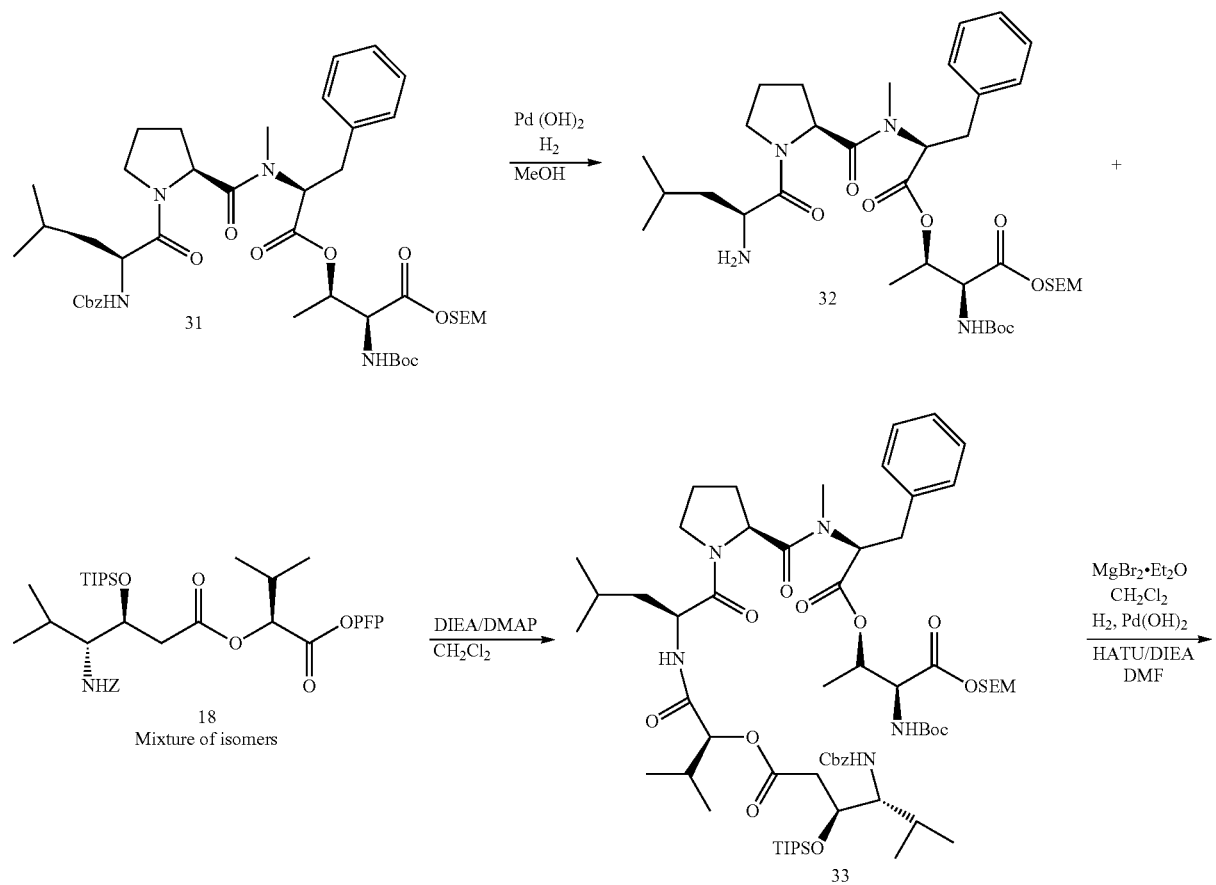

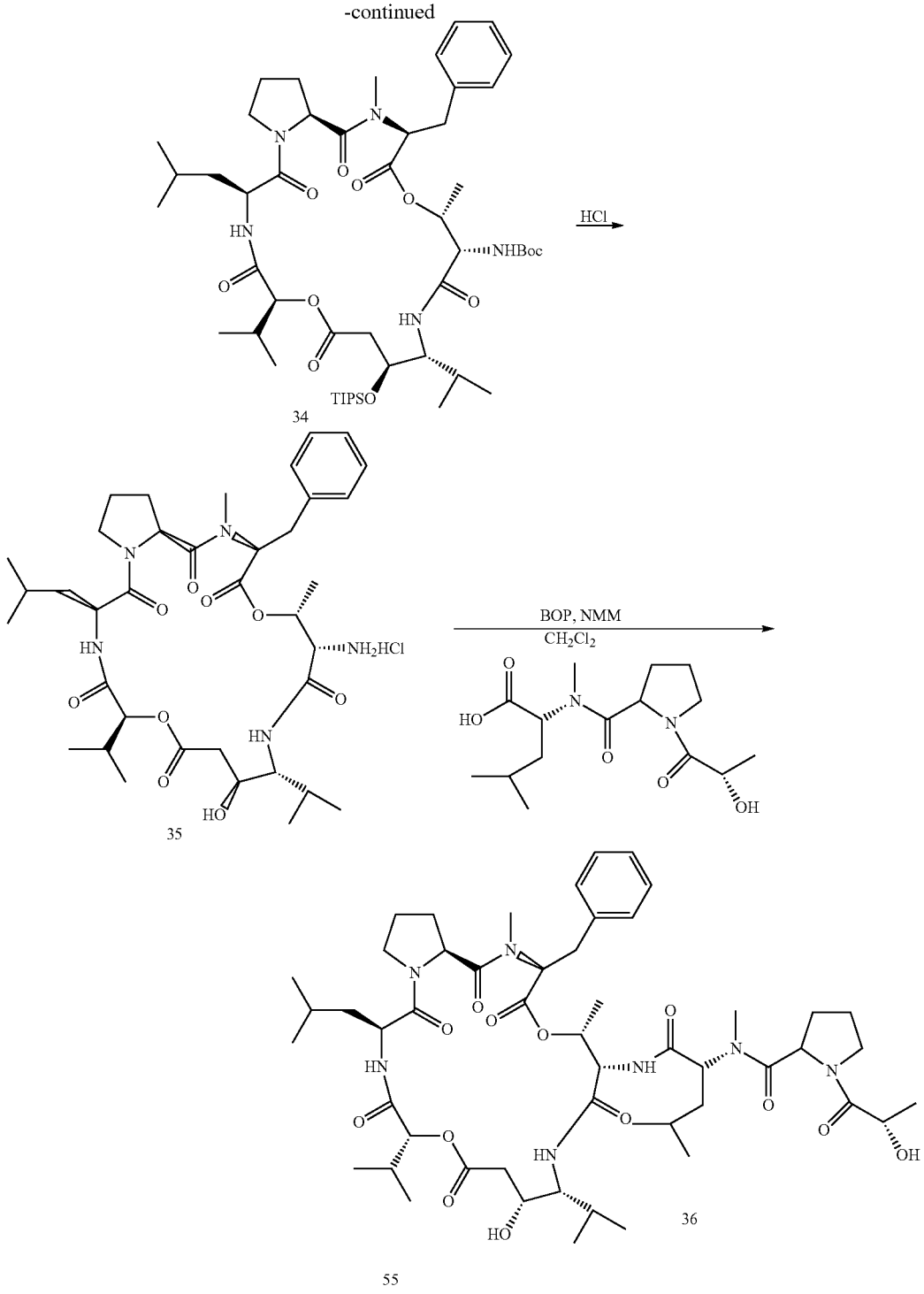

L-Cbz-N-Methylphenylalanine (28): To a solution stirred solution of L-Cbz-Phe (5.1 g, 17.8 mmol) in THF (90 mL), at 0° C., finely powered KOH (6.7 g, 0.12 mol) was added in portions, followed by the addition of tetrabutylammonium hydrogen sulfate (0.51 g, 10% by weight). Then, dimethyl sulfate (6.4 mL, 71.2 mmol) was added dropwise over 15 min. The reaction was stirred for an additional 30 min and $H_2O$ (50 mL) was added. After stirring 5 h at room temperature, 20% aqueous ammonium hydroxide solution was added (20 mL). The reaction was diluted with ether (100 mL), the aqueous layer was separated and the organic layer was extracted with saturated aq $NaHCO_3$ (2×40 mL). The combined aqueous layers were acidified to pH 1 with 1M $KHSO_4$ and extracted with EtOAc (2×200 mL). The organic layers were combined, dried ($Na_2SO_4$), filtered and concentrated. The resulting acid 28 (4.5 g, 85%) was obtained as a yellow oil and used in the next step without purification. $^1$H-NMR (500 MHz, $CDCl_3$): 2.71 and 2.78 (s, 3H), 2.94-3.06 (m, 1H), 3.17-3.32 (m, 1H), 4.79-4.89 (m, 2H), 4.95 and 5.03 (s, 2H), 7.04-7.28 (m, 10H).

L-Cbz-N-Methylphenylalanine-O-L-Boc-threonine-OSEM (29): To a solution of Cbz-N-methylphenylalanine (2 g, 6.56 mmol) in $CH_2Cl_2$ (40 mL), cooled to 0° C., Boc-Thr- OSEM (2.08 g, 5.96 mmol) was added. To the resulting solution Et$_3$N (1.9 mL, 13 mmol), DMAP (146 mg, 1.19 mmol) and isopropenyl chloroformate (0.71 mL, 6.56 mmol) were added. The reaction was stirred at 0° C. for 1 h, diluted with Et$_2$O (150 mL) and washed with 10% HCl (50 mL), 5% NaHCO$_3$ (50 mL) and saturated NaCl (50 mL) solutions. The organic layer was dried (Na$_2$SO$_4$) and the solvent evaporated. The crude oil was purified by column chromatography (silica gel, EtOAc/Hexanes 10:1) to yield the dipeptide 29 (1.79 g, 60%). $^1$H-NMR (200 MHz, CDCl$_3$): 0.0 (s, 9H), 0.96 (m, 2H), 1.25 and 1.30 (d, J=1.6 Hz, 3H), 1.46 (s, 9H), 2.75 and 2.83 (s, 3H), 2.92-3.06 (m, 1H), 3.20-3.40 (m, 1H), 3.75-3.85 (m, 2H), 4.44 (m, 2H), 4.83-4.90 (m, 1H), 5.01-5.15 (m, 3H), 5.25-5.40 (m, 2H), 5.46 (m, 1H), 7.09-7.35 (m, 10H).

L-N-Methylphenylalanine-O-L-Boc-threonine-OSEM (30): To a solution of L-Cbz-N-methylphenylalanine-O-Boc-threonine-OSEM (1.7 g. 2.6 mmol) in MeOH under argon, Pd(OH)$_2$ (170 mg) was added. The reaction was purged with H$_2$ and stirred overnight under a hydrogen atmosphere (1 atm). The mixture was filtered through Celite. The filtrate was concentrated to yield the compound 30 (1.32 g, 98%) as yellow oil. $^1$H-NMR (500 MHz, CDCl$_3$): 0.0 (s, 9H), 0.93 (t, J=8.2, 2H), 1.04 and 1.28 (d, J=5.6 Hz, 3H), 1.44 (s, 9H), 2.29 (s, 3H), 2.83 and 2.93 (dd, J=14.3 and 6.4 Hz), 3.40 (t, J=6.1 Hz, 1H), 3.66-3.68 (m, 2H), 4.48 and 5.23 (d, J=9.7 Hz), 5.02 (d, J=5.2 Hz, 2H), 7.08-7.28 (m, 5H).

L-Cbz-Leucyl-L-prolyl-L-N-methylphenylalanine-O-L-Boc-threonine-O-SEM (31): To a solution of L-Cbz-Leu-L-Pro-OH (1.0 g, 2.84 mmol) in CH$_2$Cl$_2$ (25 mL), cooled to −15° C., BOP-Cl (0.72 g, 2.84 mmol) was added, followed by the dropwise addition of NMM (318 µL, 2.84 mmol). A separate solution of 30 (1.32 g, 2.58 mmol) in CH$_2$Cl$_2$ (25 mL) was cooled to −15° C. and added to the reaction followed by the addition of N-methylmorpholine (NMM) (0.58 mL, 5.16 mmol). The mixture was stirred 15 min at −15° C., 1 h at 0° C. and overnight at room temperature. The reaction mixture was diluted with EtOAc and washed with 10% HCl (100 mL), NaHCO$_3$ (100 mL, sat) and NaCl (100 mL, sat). The organic layer was dried (Na$_2$SO$_4$) and the solvent evaporated. The crude oil was purified by column chromatography (silica gel, EtOAc/Hexanes 3/7) to yield the tetrapeptide 31 (1.02 g, 55%) as pale yellow oil. R$_f$ 0.19 (AcOEt/Hexanes 3:7). [α]$_D^{20}$=−38.5 (c=1, CH$_2$Cl$_2$). $^1$H-NMR (500 MHz, CDCl$_3$): 0.0 (s, 9H), 0.73-0.77 (m, 2H), 0.92-1.00 (m, 6H), 1.21 (d, J=6.7 Hz), 1.36 (d, J=6.7 Hz, 3H), 1.46 (s, 9H), 1.54-1.99 (m, 7H), 2.72 (s), 2.78 (s, 3H), 2.93-3.01 (m, 1H), 3.05-3.15 (m), 3.50-3.55 (m, 1H), 3.66-3.89 (m, 4H), 4.29-4.35 (m, 1H), 4.41-4.61 (m, 2H), 4.63-4.65 (m, 1H), 4.72-4.74 (dd, J=8.1 and 3.1 Hz, 1H), 4.95-5.01 (dd, J=8.1 and 3.1 Hz), 5.05-5.17 (m, 2H), 5.27-5.62 (m, 3H), 7.16-7.42 (m, 10H), 7.71 (d, J=10 Hz, 1H), 8.01 (d, J=9.2 Hz). $^{13}$C-NMR (125 MHz, CDCl$_3$): −1.46, 16.2, 16.6, 16.9, 17.9, 21.4, 23.4, 24.5, 24.7, 25.1, 28.2, 29.2, 34.5, 39.5, 40.7, 46.8, 51.1, 53.3, 55.1, 57.6, 58.8, 62.1, 65.8, 62.7, 67.9, 68.2, 71.2, 72.5, 80.1, 89.8, 90.2, 126.6, 127.3, 127.9, 128.4, 128.8, 129.4, 156.0, 169.1, 172.7, 173.8. IR (neat) 3278, 2954, 1703, 1640, 1521, 1435, 1365. HRMS m/z cald for C$_{44}$H$_{66}$N$_4$O$_{11}$SiNa (M+Na): 877.4395 found 877.4404.

L-Leucyl-L-prolyl-L-N-methylphenylalanine-O-L-Boc-threonine-OSEM (32): To a solution of 31 (223 mg, 0.26 mmol) in MeOH under argon, Pd(OH)$_2$ (50 mg) was added. The reaction was purged with H$_2$ and stirred overnight under H$_2$ atmosphere (1 atm). The mixture was filtered through Celite. The filtrate was concentrated to yield the free amino tetrapeptide 32 (192 mg, 97%) as yellow oil, which was used in the next step without purification. $^1$H-NMR (500 MHz, CDCl$_3$): 0.0 (s, 9H), 0.72-0.76 (m, 2H), 0.90-0.99 (m, 6H), 1.22 (d, J=6.7 Hz), 1.35 (d, J=6.7. Hz, 3H), 1.45 (s, 9H), 1.47-1.53 9m, 2H), 1.81-2.01 (m, 5H), 2.71 (s), 2.79 (s, 3H), 2.92-3.00 (m, 1H), 3.05-3.15 (m), 3.51-3.56 (m, 1H), 3.67-3.90 (m, 4H), 4.29-4.35 (m, 1H), 4.42-4.63 (m, 2H), 4.63-4.65 (m, 1H), 4.72-4.74 (dd, J=8.0 and 3.2 Hz, 1H), 5.01 (d, J=6.0 Hz, 1H), 5.21-5.59 (m, 3H), 7.05-7.29 (m, 5H), 7.53 (d, J=10 Hz), 7.68 (d, J=9.1 Hz).

[N-MePhe$^5$]-Tamandarin B Protected Linear Precursor (33): To a solution of the PPP ester 18 (191 mg, 0.26 mmol) in CH$_2$Cl$_2$ (5 mL), cooled to 0° C. was added DIEA (116 µL, 0.65 mmol) and the solution was stirred for 20 min, followed by the addition of amine 32 (192 mg, 0.27 mmol) in CH$_2$Cl$_2$ (5 mL) and DMAP (0.6 mg, 0.006 mmol). The reaction mixture was stirred at 0° C. for 1 h and then at it for an additional 1 h. The reaction was quenched with NH$_4$Cl and diluted with CH$_2$Cl$_2$. The organic layer was washed with 10% HCl (100 mL), 5% NaHCO$_3$ (100 mL) and NaCl (100 mL, sat), dried (Na$_2$SO$_4$), filtered and concentrated. The crude oil was purified by column chromatography (silica gel, EtOAc/Hexanes 9:1) to yield 33 (153 g, 44%) as colorless oil. R$_f$ 0.20 (AcOEt/Hexanes 3/1). [α]$_D^{20}$=−44.0 (c=1, CHCl$_3$). $^1$H-NMR (500 MHz, CDCl$_3$): 0.0 (s, 9H), 0.87-0.89 (m, 2H), 0.90-0.98 (m, 18H), 1.02-1.10 (m, 21H), 1.43 (s, 4H), 1.11-2.10 (m, 9H), 2.49-2.51 (m, 3H), 2.68 (s, 3H), 2.89 (s, 3H), 3.09-3.17 (m, 2H), 3.65-3.67 (m, 1H), 3.68-3.72 (m, 5H), 4.31-4.45 (m, 1H), 4.20-4.33 (m, 3H), 4.69-4.79 (m, 2H), 4.96-5.05 (m, 3H), 5.18-5.43 (m, 3H), 5.47 (d, J=6.0 Hz, 1H), 6.83 (d, J=7.9 Hz, 1H), 7.11-7.41 (m, 11H), 7.82 (d, J=6.5 Hz, 1H), 8.88 (d, J=8.5 Hz, 1H). $^{13}$C-NMR (125 MHz, CDCl$_3$): 13.1, 17.3, 18.1, 18.5, 19.3, 20.9, 21.6, 23.9, 25.4, 28.6, 29.6, 30.5, 34.8, 35.0, 39.9, 47.3, 49.4, 55.3, 57.3, 59.3, 60.7, 62.6, 66.7, 68.6, 79.1, 80.6, 90.6, 127.1, 128.2, 129.3, 137.4, 156.8, 157.1, 169.5, 170.4, 171.0, 172.1, 174.2. IR (neat) 3446, 2956, 2868, 1738, 1703, 1636 1455. HRMS m/z cald for C$_{65}$H$_{107}$N$_5$O$_{15}$Si$_2$Na (M+Na): 1276.7199 found 1276.7273.

[N-MePhe$^5$]-Tamandarin B Protected Macrocycle (34): To a solution of the fully protected linear precursor 33 (140 mg, 0.11 mmol) dissolved in CH$_2$Cl$_2$ (5 mL), at 0° C., MgBr$_2$.Et$_2$O (85 mg, 0.33 mmol) was added. The reaction was stirred at 0° C. for 2 h and overnight at rt. The reaction was diluted with CH$_2$Cl$_2$ and the organic layer was washed with 10% HCl (100 mL) and NaCl (100 mL, sat), dried (Na$_2$SO$_4$), filtered and concentrated. The resulting acid (130 mg) was obtained as a white foam and use directly in the next step. To a solution of crude acid (130 mg, 0.30 mmol) in MeOH (5 mL) under argon, Pd(OH)$_2$ (28 mg) was added. The reaction was purged with H$_2$ and stirred overnight under H$_2$ atmosphere (1 atm). The mixture was filtered through Celite. The filtrate was concentrated to yield the linear precursor (87 mg, 78%) as a white foam which was used directly in the next step. The crude amino acid linear precursor (87 mg, 0.08 mmol) was dissolved in DMF (9 mL) and cooled to 0° C. HATU (40 mg, 0.10 mmol) was added followed by the dropwise addition of DIEA (46 µL, 0.26 mmol). The reaction mixture was stirred at 0° C. for 1 h and then overnight. The reaction mixture was concentrated in vacuo, diluted with EtOAc (10 mL) and washed with 10% HCl (10 mL), 5% NaHCO$_3$ (10 mL) and NaCl (10 mL, sat), dried (Na$_2$SO$_4$), filtered and concentrated. The crude oil was purified by column chromatography (silica gel, EtOAc/Hexanes 5/1) to yield protected macrocycle 34 (10 mg, 15% three steps overall) as white foam. R$_f$ 0.40 (AcOEt/Hexanes 3/7). [α]$_D^{20}$=−36.1 (c=1, CHCl$_3$). $^1$H-NMR (500 MHz, CDCl$_3$): 0.79-1.09 (m, 18H), 1.09-1.10 (s, 21H), 1.27 (d, J=6.4 Hz, 3H), 1.44 (s, 9H), 1.56-1.70 (m, 3H), 1.73-1.81 (m, 1H), 1.99-2.23 (m, 4H), 2.27 (dd, J=17.0 and 2.9 Hz, 1H), 2.42 (dd, J=17.0 and 3.0 Hz, 1H), 2.50 (s, 3H), 2.61 (dd, J=17.1 and 6.5 Hz, 1H), 2.98-3.00 (m, 1H), 3.19-3.23 (m, 1H), 3.30-3.32 (m, 1H), 3.42 (dd, J=9.8 and 4.9 Hz, 1H), 3.57 (dd, J=10 and 4.4 Hz, 1H), 3.60-3.62 (m, 1H), 3.63-3.64 (m, 1H), 4.03-4.21 (m, 1H), 4.32-4.36 (m, 1H), 4.37-4.45 (m, 1H), 4.57-4.60 (m, 1H), 4.60-4.69 (m, 1H), 4.88-4.92 (m, 1H), 4.94 (d, J=6.0 Hz, 1H), 5.80 (m, 1H), 7.12-7.17 (m, 2H), 7.28-7.31 (m, 3H), 7.48-7.51 (m, 2H). $^{13}$C-NMR (125 MHz, CDCl$_3$): 12.2, 12.6, 15.1, 16.5, 17.5, 18.0, 18.2, 18.8, 19.6, 20.7, 21.0, 23.5, 24.9, 27.9, 28.1, 30.1, 31.0, 35.1, 38.5, 39.7, 40.9, 47.7, 48.1, 55.5, 56.9, 59.3, 65.9, 68.8, 69.9, 71.8, 80.1, 81.2, 126.9, 128.7, 129.5, 138.1, 155.9, 168.7, 170.9, 171.0, 172.2. IR (neat) 3331, 2926, 1743, 1636, 1513, 1456.

[N-MePhe$^5$]-Tamandarin B (36): To a solution of Boc protected macrocycle 34 (10 mg, 0.01 mmol) in HPLC EtOAc was added a solution of HCl in EtOAc. The resulting solution was stirred at room temperature for 2 h. The solution was concentrated, and the residue diluted with CH$_2$Cl$_2$ and concentrated again to yield the hydrochloride salt 35 (9 mg, quantitative yield) as a white solid, which was used directly in the next step. To a mixture of the macrocycle amine salt (9 mg, 0.01 mmol) and side chain (6.1 mg, 0.015 mmol) in CH$_2$Cl$_2$ (0.50 mL) at 0° C. was added BOP (8.4 mg, 0.015 mmol) and NMM (6 µL, 0.05 mmol). After 30 min at 0° C., the reaction was stirred at rt overnight The reaction was treated with NaCl solution (2 mL, sat) and extracted with EtOAc (2×10 mL) The organic layers were washed with 10% HCl (5 mL), 5% NaHCO$_3$ (5 mL) and NaCl (5 mL, sat), dried (Na$_2$SO$_4$), filtered and concentrated. The crude oil (8 mg, 61%) was purified by HPLC.

Example 3

Attempted Synthesis of Leu$^5$ Tamandarin B

The attempted synthesis of a leucine analog of tamandarin B (Leu$^5$ Tamandarin B) is shown in schemes shown below.

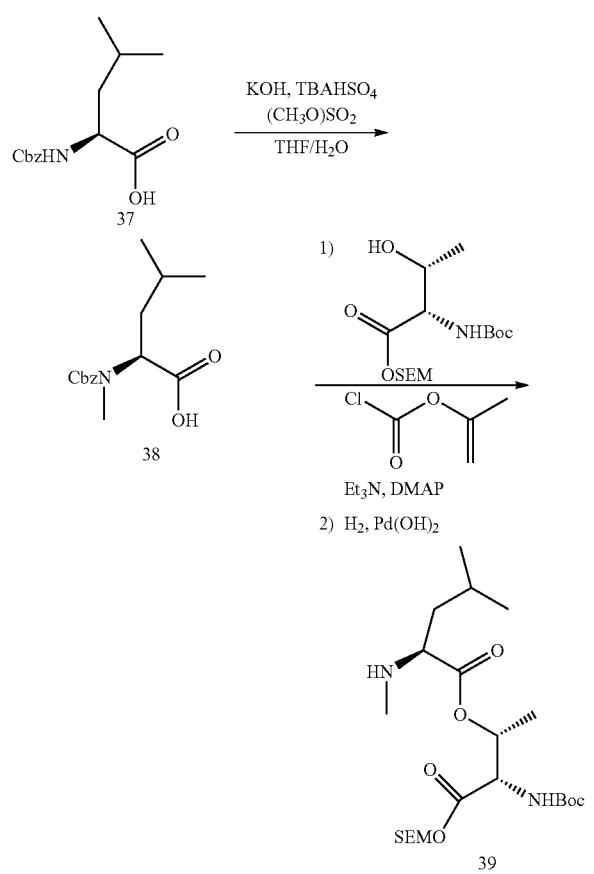

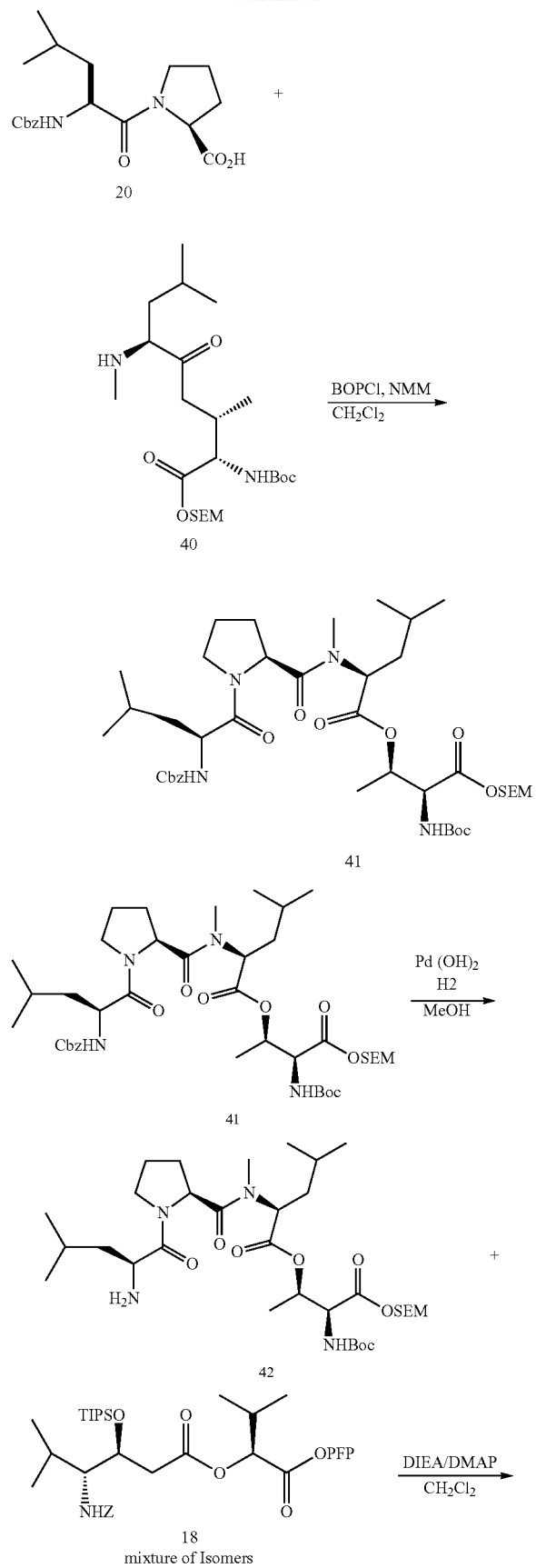

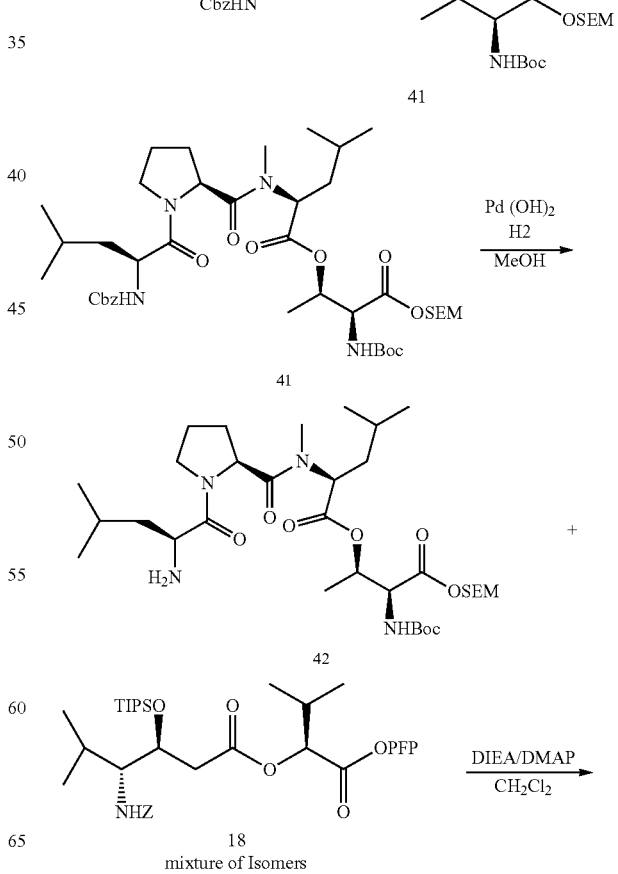

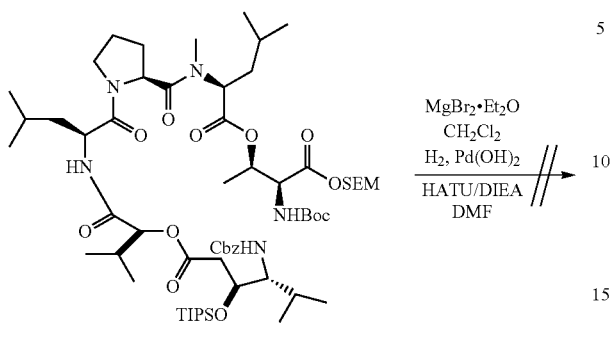

The tetrapeptide unit consisting of Leu$^3$, Pro$^4$, Leu$^5$, and Thr$^6$ (compound 41) was prepared from L-leucine using the same known synthetic sequence starting from Cbz-L-Leu (37) instead of Cbz-L-Phe or Cbz-L-Tyr (Scheme 9).

Compound 41 was deprotected using hydrogen and palladium hydroxide to yield amine 42. Compound 42 was reacted with compound 18 (used as a mixture of isomers) under conditions similar to those used above, e.g., for preparing compound 33. This reaction produced compound 43. Cyclization of compound 43 was attempted under conditions shown above, e.g., for preparing compound 34. However, the cyclization reaction under these conditions was not successful.

Example 4

Synthesis of Ser$^6$ Tamandarin B

A serine analog of tamandarin B (Ser$^6$ Tamandarin B) was synthesized as shown in Schemes 12-16.

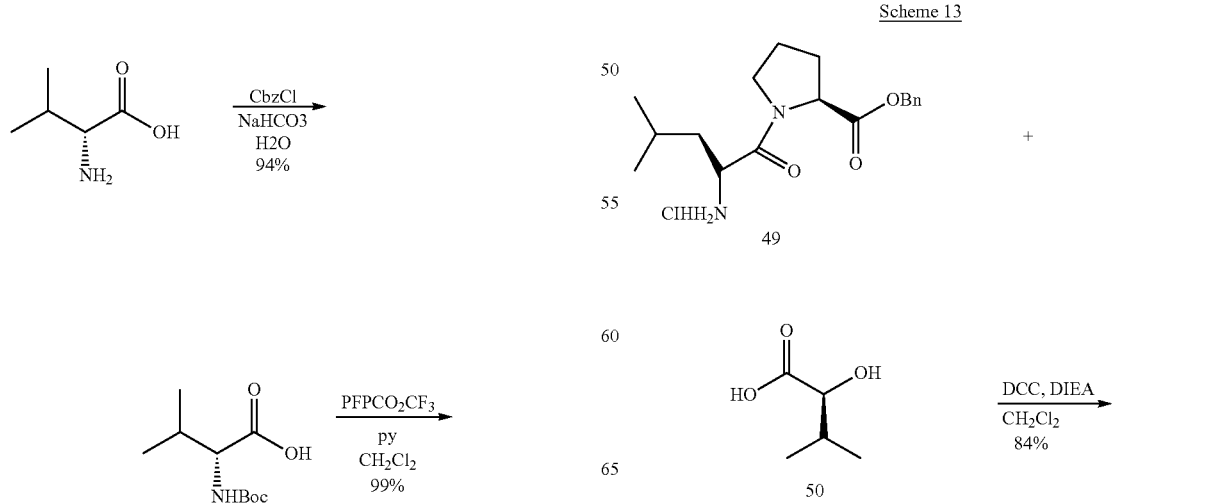

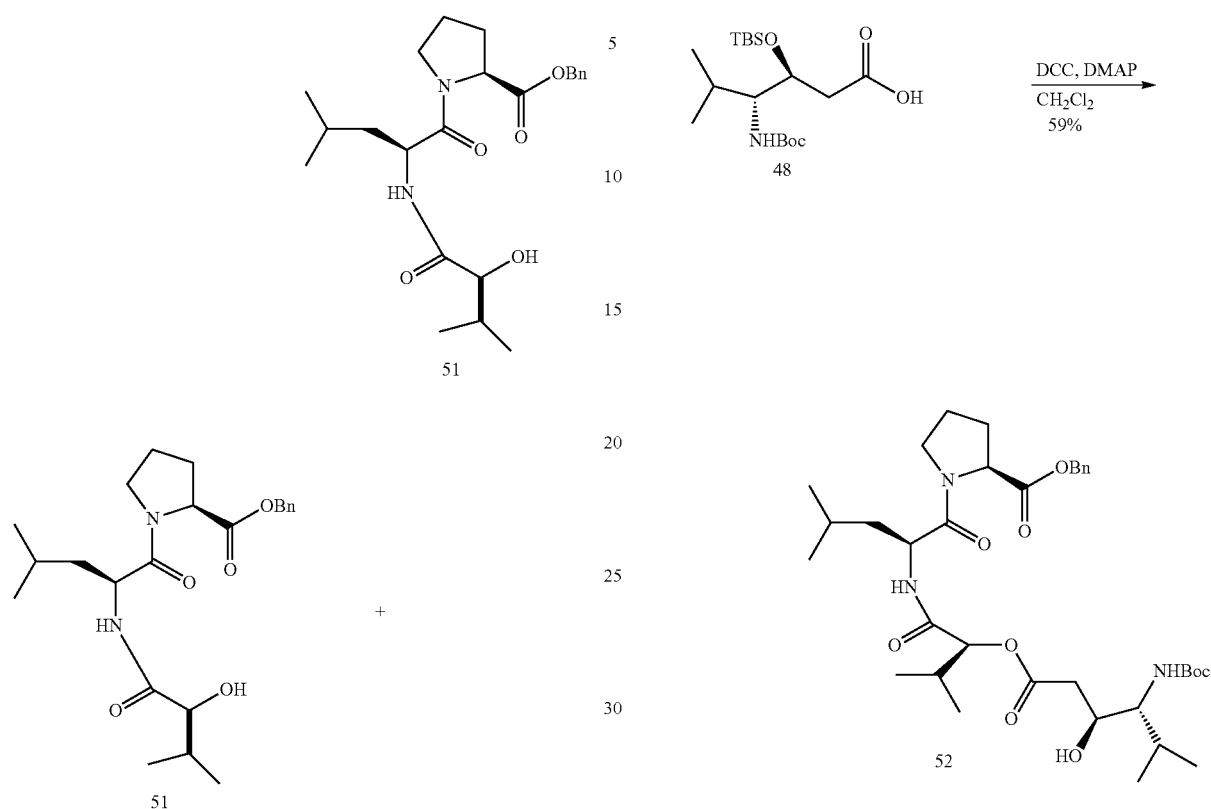
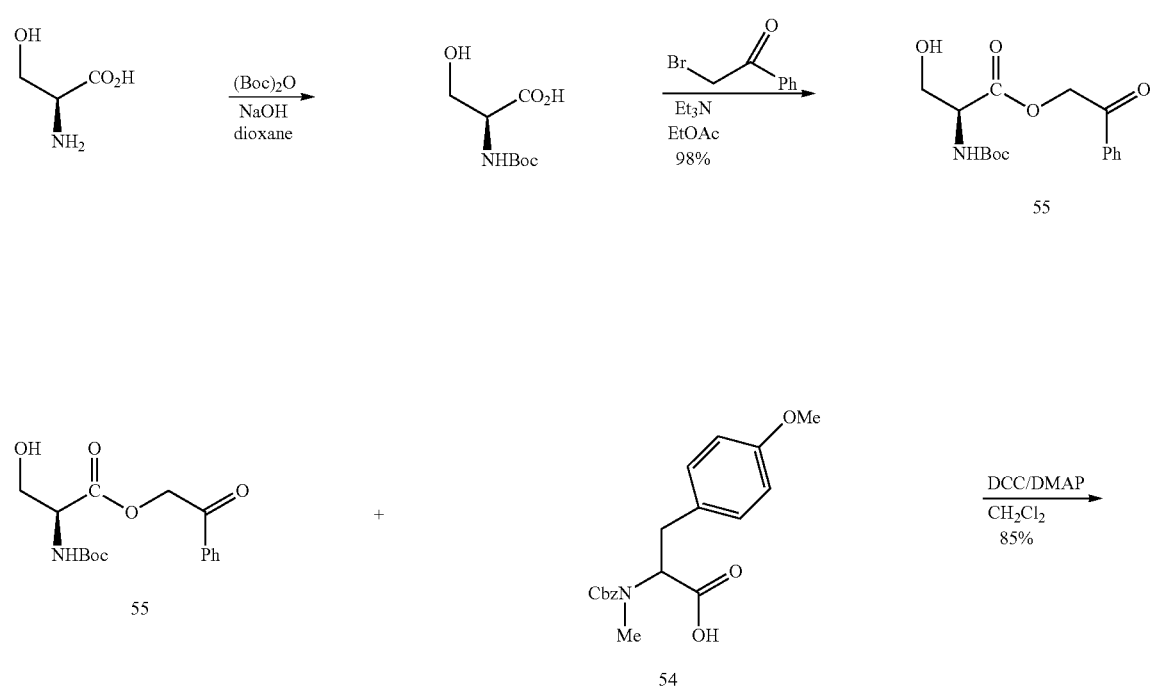
Scheme 14

-continued
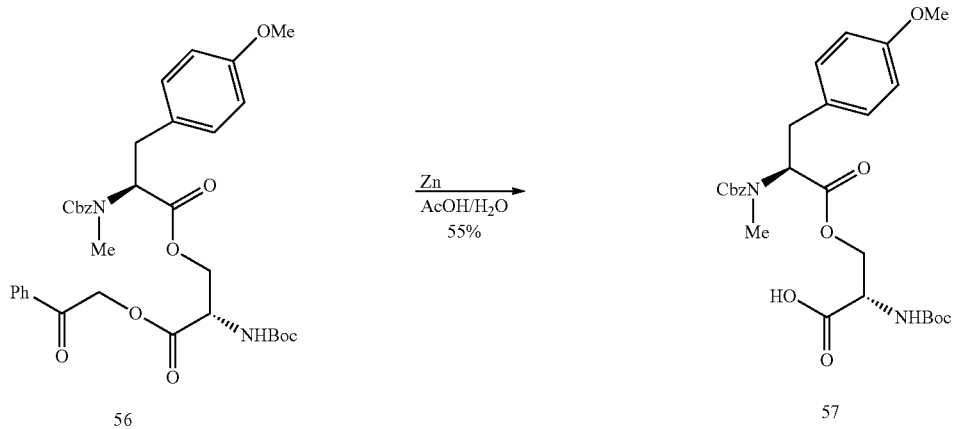
-continued
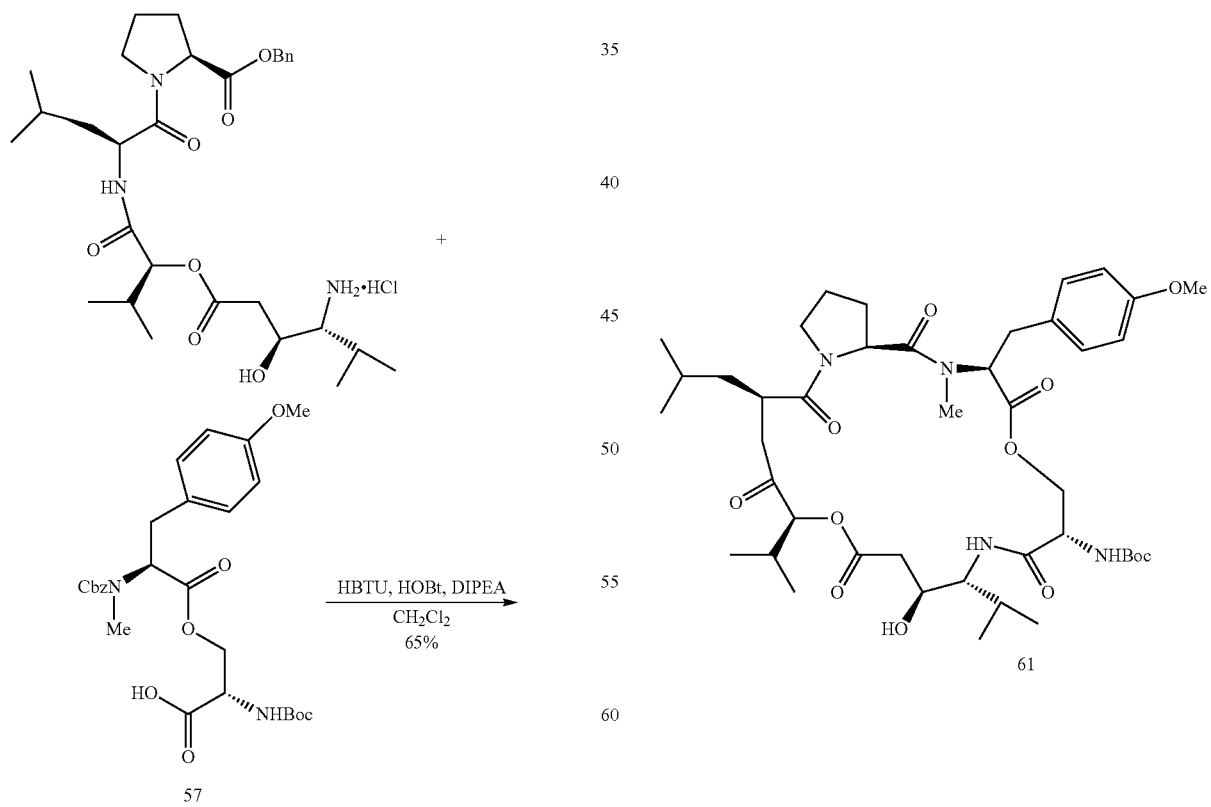

Scheme 16

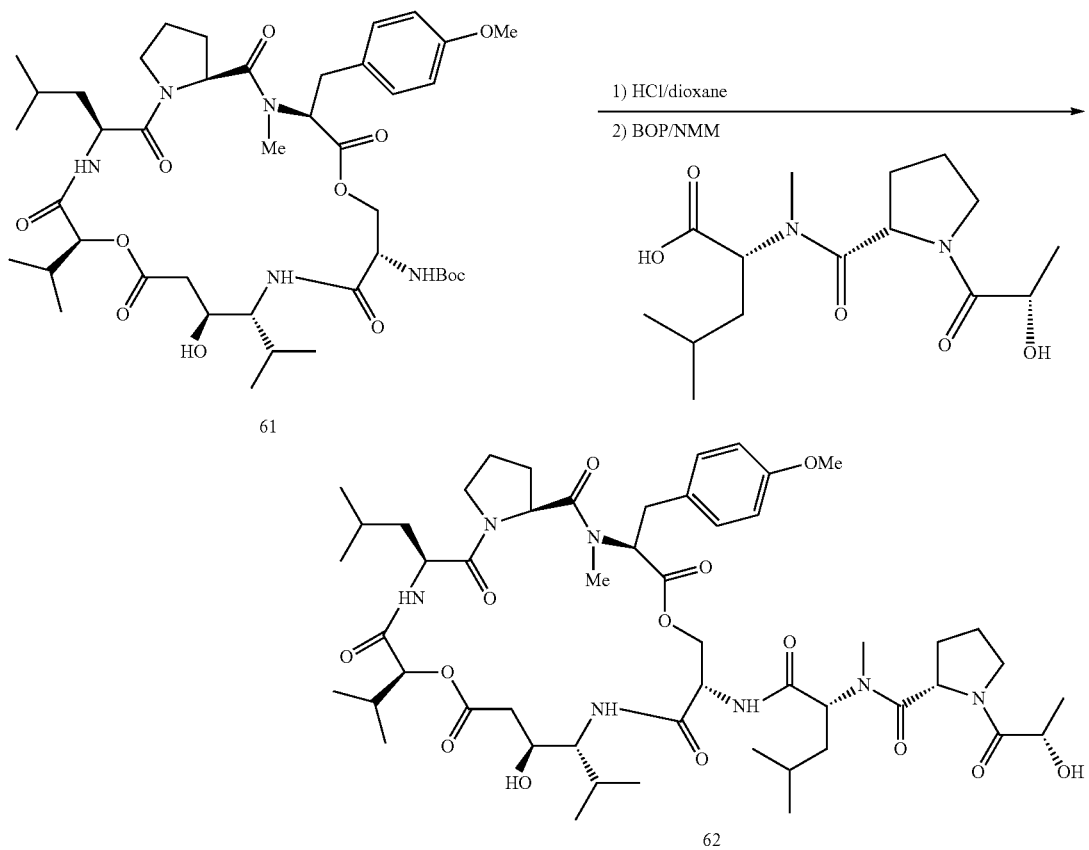

D-N-Boc-Valine pentafluophenyl (PFP) Ester (44): D-N-Boc-Valine (5 g, 23 mmol) was dissolved in CH$_2$Cl$_2$ (60 mL) and cooled to 0° C., followed by the addition of pyridine (1.7 mL, 25.3 mmol,) and PFP-trifluoroacetate (4.08 mL, 27.6 mmol). The solution was stirred 1 h at room temperature and quenched with NH$_4$Cl (50 mL, sat). The organic layer was washed with 5% HCl (100 mL), NaHCO$_3$ (100 mL, sat), dried (Na$_2$SO$_4$), filtered and the solvent evaporated. The resulting PFP ester 44 was obtained as a colorless oil (8.6 g, 98%) and used directly in the next step. $^1$H-NMR (500 MHz, CDCl$_3$): 1.03 (d, J=6.7 Hz, 3H), 1.09 (d, J=6.7 Hz, 3H), 1.47 (s, 9H), 2.30-2.38 (m, 1H), 4.57-4.58 (m, 1H), 5.01-5.02 (m, 1H).

(4R)-4-tert-Butoxycarbonylamino-5-methyl-3-oxohexanoic Acid Methyl Ester (45): To a solution of PFP ester 44 (7 g, 18.3 mmol) in anhydrous THF (30 mL), cooled to –78° C., a solution of lithium enolate of methyl acetate was added. The enolate was prepared by addition of methyl acetate (5.4 mL, 65.0 mmol) to a solution of LDA (65.0 mmol in 50 mL of anhydrous THF) at –78° C. and the resulting solution was stirred for 1 h. The reaction mixture was stirred for 45 min more at the same temperature, and quenched with NH$_4$Cl (50 mL) at –78° C. After warming to room temperature, the solution was diluted with EtOAc (150 mL). The organic layer was separated and washed with 10% HCl (100 mL), 5% NaHCO$_3$ (100 mL) and NaCl (100 mL, sat), dried (Na$_2$SO$_4$), filtered and concentrated. The crude oil was purified by column chromatography (silica gel, EtOAc/Hexanes 1/9) to yield the methyl ester 45 (3.0 g, 61%) as colorless oil. R$_f$ 0.14 (EtOAc/Hexanes 1/9). [α]$_D^{20}$=–13.2 (c=0.5, CHCl$_3$). $^1$H-NMR (500 MHz, CDCl$_3$): 0.81 (d, J=6.8 Hz) and 0.83-0.92 (m, 2H), 0.99 (d, J=6.8 Hz, 2H), 1.44 (s, 9H), 2.20-2.25 (m, 1H), 3.53 (m, 2H), 3.71 (s, 3H). 4.29 (m, 1H), 5.09 (m, 1H). $^{13}$C-NMR (125 MHz, CDCl$_3$): 16.6, 19.7, 28.2, 29.5, 46.8, 52.3, 64.3, 80.08, 155.9, 167.1, 202.0. IR (neat) 3442.3, 2966.2, 1750.0, 1715.9, 1515.0, 1508.3, 1366.9, 1165.6, 1014.0. HRMS m/z cald for C$_{13}$H$_{24}$NO$_5$ (MPH): 274.1654 found 274.1654.

(3S,4R)-4-tert-Butoxycarbonylamino-3-hydroxy-5-methylhexanoic Acid Methyl Ester (46): To a solution of methyl ester 45 (2.4 g, 8.70 mmol) in HPLC MeOH (100 mL), cooled to –78° C., potassium borohydride (1.4 g, 26.1 mmol) was added in portions. The reaction mixture was stirred at –78° C. for 10 min, warmed to –20° C. for 30 min and then to 0° C. for 10 min. The reaction was quenched with acetic acid to pH=7 and extracted with CH$_2$Cl$_2$ (3×50 mL). The organic layer was washed with NaHCO$_3$ (50 mL, sat), NaCl (50 mL, sat), dried (Na$_2$SO$_4$), filtered, and evaporated. The alcohol 46 was obtained as a colorless oil (2.2 g, 92%) and used directly in the next step. $^1$H-NMR (500 MHz, CDCl$_3$): 0.88 (d, J=6.8 Hz, 3H), 0.93 (d, J=6.8 Hz, 3H), 1.44 (s, 9H), 2.03-2.17 (m, 1H), 2.41-2.52 (m, 1H), 2.58-2.63 (m, 1H), 3.50-3.55 (m, 1H), 3.71 (s, 3H), 3.89-3.93 (m, 1H), 3.38-3.41 (m, 1H).

(3S,4R)-4-tert-Butoxycarbonylamino-5-methyl-3-(tert-butyldimethyl-silanyloxy)hexanoic Acid Methyl Ester (47): To a solution of the crude alcohol 46 (2.2 g, 7.9 mmol) in DMF (12 mL), under argon, cooled to 0° C., imidazole (1.61 g, 23.7 mmol) and tert-butyldimethylsilyl chloride (3.57 mL, 23.7 mmol) were added. The reaction mixture was stirred at 0° C. for 30 min and then at room temperature for 18 h and diluted with Et$_2$O (50 mL). The organic layer was separated and washed with 10% HCl (50 mL), NaHCO$_3$ (50 mL, sat) and NaCl (50 mL, sat), dried (Na$_2$SO$_4$), filtered, and concentrated. The crude oil was purified by column chromatography (silica gel, EtOAc/Hexanes 1/9) to yield 47 (2.59 g, 98%) as colorless oil. R_f 0.31 (EtOAc/Hexanes 1/9). [α]_D^20=+5.30 (c=1, CH_2Cl_2). $^1$H-NMR (500 MHz, CDCl_3): 0.07 (s, 6H), 0.84-0.91 (m, 15H), 1.42 (s, 9H), 1.98-2.01 (m, 1H), 2.43 (dd, J=6.0 and 19 Hz, 1H), 2.52 (dd, J=5.9 and 18.5 Hz, 1H), 3.47-3.48 (m, 1H), 3.65 (s, 3H), 4.17-4.19 (m, 1H), 4.41-4.44 (m, 1H). $^{13}$C-NMR (125 MHz, CDCl_3): −3.6, 16.6, 17.60, 18.9, 25.7, 27.8, 28.2, 39.9, 51.5, 51.9, 59.5, 70.19, 155.9, 172.2. IR (neat) 3373.1, 2960.7, 1717.0, 1504.6, 1366.1, 1173.0, 837.0. HRMS m/z cald for C_19H_39NO_5Si (M+Na): 390.2675 found 390.2676.

(3S,4R)-4-tert-Butoxycarbonylamino-5-methyl-3-(tert-butyldimethyl-silanyloxy)hexanoic Acid (48): To a solution of 47 (500 mg, 1.28 mmol) in 25 mL of THF/MeOH (1:1), cooled to 0° C., 1N NaOH solution (25 mL) was added. The reaction was stirred at 0° C. for 2 h and then overnight at rt. The reaction mixture was concentrated and diluted with H_2O (20 mL), acidified to pH 2 with 1N KHSO_4 solution, and extracted with EtOAc (3×20 mL). The combined organic layers were washed with NaCl (50 mL, sat), dried (Na_2SO_4), filtered and evaporated. The resulting acid 48 was obtained as a colorless oil (1.76 g, 86%) and used directly in the next step. $^1$H-NMR (500 MHz, CDCl_3): 0.06 (s, 6H), 0.84-0.95 (m, 15H), 1.43 (s, 9H), 2.01-2.11 (m, 1H), 2.53 (m, 1H), 2.64 (m, 1H), 3.53-3.58 (m, 1H), 4.10-4.14 (m, 1H), 3.65 (s, 3H), 4.17-4.19 (m, 1H), 4.51-4.54 and 6.29-6.31 (m, 1H).

N-α-Hydroxyvaleryl-N-Leucyl-Proline Acid Benzyl Ester (51): To a solution of hydrochloride salt 49 (1.56 mg, 4.23 mmol) in CH_2Cl_2 (2 mL), cooled to 0° C., NMM (522 μL, 4.65 mmol) was added. After 15 min α-hydroxyvaleric acid (50) (500 mg, 4.23 mmol) and DCC (959 mg, 4.65 mmol) were added in portions. The reaction mixture was stirred 14 h at room temperature diluted with CH_2Cl_2 (25 mL) and washed with HCl 1N (20 mL), NaHCO_3 (20 mL, sat) and brine (20 mL), dried (Na_2SO_4), filtered and concentrated. The crude oil was purified by column chromatography (silica gel, grad EtOAc/Hexanes 1/1 to 3/1) to yield 51 (1.47 g, 84%) as a white solid. R_f 0.46 (EtOAc/Hexanes 1/2). $^1$H-NMR (500 MHz, CDCl_3): 0.81 (d, J=7.0 Hz, 3H), 0.92 (m, 6H), 0.97 (d, J=7.0 Hz, 3H), 1.42 (m, 1H), 1.63 (m, 2H), 2.00 (m, 3H), 2.19 (m, 2H), 3.60 (m, 1H), 3.85 (m, 1H), 3.88 (d, J=4.8 Hz, 1H), 4.66 (m, 1H), 4.80 (m, 1H), 5.06 (d, J=12.3 Hz, 1H), 5.14 (d, J=12.3 Hz, 3H), 7.32 (m, 5H), 7.41 (d, 8.4, 1H). $^{13}$C-NMR (125 MHz, CDCl_3): 15.3, 19.1, 21.3, 23.1, 24.4, 24.7, 28.8, 31.3, 40.5, 46.8, 48.2, 58.2, 66.7, 75.8, 127.9, 128.1, 128.3, 135.3, 117.4, 117.9, 173.9.

(3S,4R)-4-tert-Butoxycarbonylamino-5-methyl-3-(tert-butyldimethyl-silanyloxy)hexanoic Acid N-α-Hydroxy-valeryl-N-Leucyl-O-Benzyl-Prolyl Ester (52): To a solution of alcohol 51 (400 mg, 0.96 mmol) in CH_2Cl_2 (8 mL), cooled to −5° C., DMAP (35 mg, 0.28 mmol) acid 48 (425 mg, 1.15 mmol) and DCC (247 mg, 1.15 mmol) were added in portions. The reaction mixture was stirred 7 h at −5° C., filtered, and evaporated. The residue was dissolved in CH_3CN (10 mL), filtered again, and evaporated. The crude oil was dissolved in EtOAc (20 mL) and washed with 10% KHSO_4 (15 mL), NaHCO_3 (15 mL, sat) and NaCl (15 mL, sat). The organic layer was dried (Na_2SO_4) and the solvent evaporated. The crude oil was purified by column chromatography (silica gel, grad EtOAc/Hexanes 1/4) to yield 52 (110 mg, 60%). R_f 0.47 (AcOEt/Hexanes 1:1). [α]_D^20=−69.0 (c=1, CH_2Cl_2). $^1$H-NMR (500 MHz, CDCl_3): rotamers 0.07 (s, 6H), 0.75-1.10 (m, 27H), 1.49 (s, 9H), 1.50-1.71 (m, 2H), 1.75-2.20 (m, 3H), 2.12-2.21 (m, 2H), 2.41-2.63 (m, 2H), 3.12-3.15 (m, 1H), 3.41-3.49 (m, 2H), 3.53-3.62 (m, 2H), 3.68-3.72 (m, 1H), 3.81-3.88 (m, 1H), 4.05-4.10 (m, 1H), 4.21 (d, J=8.0 Hz, 1H), 4.49-4.51 (m, 1H), 4.60-4.69 (m, 2H), 4.77 (d, J=10.0 Hz, 1H), 4.90-5.01 (m, 2H), 5.11-5.22 (m, 2H), 6.88 (d, J=9.0 Hz, 1H), 7.22-7.33 (m, 5H), 8.33 (d, J=6.3 Hz, 1H). $^{13}$C-NMR (125 MHz, CDCl_3): −5.1, −4.8, 14.7, 17.8, 18.0, 18.9, 20.4, 21.2, 23.2, 24.6, 24.7, 24.9, 25.4, 25.7, 28.4, 28.8, 30.2, 33.9, 38.9, 43.0, 48.4, 58.8, 63.2, 66.8, 71.5, 79.3, 82.6, 128.1, 128.3, 128.5, 135.5, 157.4, 170.0, 170.9, 171.2, 171.8, 172.1. IR (neat) 3265.8, 2937.7, 2903.6, 2362.0, 1740.4, 1692.3, 1643.4, 1451.6, 1386.8, 1365.4, 1167.2, 1091.1, 837.3. HRMS m/z cald for C_41H_69N_3O_9SiNa (M+Na): 796.4700 found 798.4735.

L-N-Boc-Serine phenacyl ester (55): To a stirred suspension of L-N-Boc-serine (2 g, 9.7 mmol) in EtOAc (20 mL), cooled to 0° C., Et_3N (1.39 mL, 9.7 mmol) and bromoacetophenone (1.9 g, 9.7 mmol) were added. The resulting mixture was stirred at room temperature for 2 days, diluted with EtOAc (50 mL) and washed with 10% HCl (20 mL), 5% NaHCO_3 (20 mL) and saturated NaCl (20 mL) solutions. The organic layer was dried (Na_2SO_4) and the solvent evaporated. The residue was triturated with ether and filtered to afford 55 (3.4 g, 98%) as a yellow foam. R_f 0.50 (AcOEt/Hexanes 1/1). [α]_D^20=−19.1 (c=1, CHCl_3). $^1$H-NMR (500 MHz, CDCl_3): 1.43 and 1.46 (s, 3H), 3.70-3.73 (m, 1H), 3.84-3.88 (m, 1H), 4.22-4.24 (m, 1H), 4.51-4.52 (m, 1H), 5.28-5.36 (m, 1H), 5.61-5.66 (m, 2H), 7.49 (t, J=6.5 Hz, 2H), 7.57 (t, J=6.3 Hz, 1H), 7.87 (dd, J=1.9 and 6.3 Hz, 2H). $^{13}$C-NMR (125 MHz, CDCl_3): 27.2, 28.1, 56.0, 63.7, 66.3, 79.8, 85.0, 127.6, 128.8, 133.3, 134.3, 146.6, 155.5, 170.1, 192.8. IR (neat) 3439.8, 2978.7, 2935.6, 1807.8, 1756.6, 1704.8, 1506.6, 1369.7, 1162.9.

O-(L-N-Cbz-N,O-Dimethyltyrosyl)-L-N-Boc-serine Phenacyl Ester (56): To a solution of L-N-Boc-serine phenacyl ester 55 (1.42 g, 3.96 mmol) in CH_2Cl_2 (20 mL), cooled to 0° C., DMAP (145 mg, 1.18 mmol) and L-N-Cbz-N,O-dimethyltyrosine (21) (1.36 g, 3.96 mmol) were added. After stirring 10 min at 0° C., DCC (897 mg, 4.35 mmol) was added. The reaction mixture was stirred overnight at room temperature. The mixture was filtered and the filtrate concentrated to dryness. The residue was dissolved in CH_3CN (25 mL), filtered again and evaporated. The crude oil was dissolved in EtOAc (50 mL) and washed with 10% KHSO_4 (30 mL), NaHCO_3 (50 mL, sat) and NaCl (50 mL, sat). The organic layer was dried (Na_2SO_4) and the solvent evaporated. The crude oil was purified by column chromatography (silica gel, grad EtOAc/Hexanes 1/4 to 1/2) to yield the dipeptide 56 (1.69 g, 63%) as a pale white solid. R_f 0.12 (AcOEt/Hexanes 1:4). mp=64-65° C. [α]_D^20=−12.0 (c=1, CH_2Cl_2). $^1$H-NMR (500 MHz, CDCl_3): 1.49 (s, 3H), 2.85 and 3.01 (s, 3H), 3.04-3.11 (m, 1H), 3.27-3.37 (m, 1H), 3.80 (s, 3H), 4.53-4.67 (m, 1H), 4.70 (dd, J=3.9 and 11.7 Hz, 1H), 4.81-4.82 (m, 1H), 4.94-5.01 (m, 1H), 5.08-5.14 (m, 2H), 5.30-5.35 (m, 1H), 5.48-5.52 (m, 1H), 6.76-6.83 (m, 2H), 7.05-7.24 (m, 2H), 7.27-7.34 (m, 5H), 7.51 (t, J=7.3 Hz, 2H), 7.64 (t, J=7.2 Hz, 1H), 7.89 (d, J=7.5 Hz, 2H). $^{13}$C-NMR (125 MHz, CDCl_3): 28.3, 32.2, 33.8, 34.2, 52.9, 55.1, 60.9, 64.9, 67.2, 67.3, 113.9, 127.4, 127.7, 127.8, 127,9, 128.3, 128.9, 129.1, 129.8, 133.9, 136.6, 158.3, 170.4, 170.6, 190.8. IR (neat) 3404.1, 2932.5, 1703.2, 1513.7, 1453.1, 1402.5, 1248.0, 1162.6, 1033.0, 754.8.

O-(L-N-Cbz-N,O-Dimethyltyrosyl)-L-N-Boc-serine (57): To a solution of serine phenacyl ester 56 (500 mg, 0.73 mmol) in aq. AcOH (6 mL, 90%), cooled to 0° C., powered Zn (381 mg, 5.48 mmol) was added. The resulting mixture was stirred 3 h at 0° C., filtered over Celite® and the Celite® washed with EtOAc (25 mL). The filtrate was washed with 10% KHSO_4 (20 mL), NaHCO_3 (20 mL, sat), and NaCl (20 mL, sat). The organic layer was dried (Na_2SO_4), and the solvent evaporated. The crude oil was purified by column chromatography (silica gel, MeOH/CH_2Cl_2 1/9) to yield the acid 57 (290 mg, 75%) as a white solid. R_f 0.35 (MeOH/CH_2Cl_2 1/9). mp=71-72° C. [α]_D^20=−2.5 (c=1, CH_2Cl_2). $^1$H-NMR (500 MHz, CDCl_3): 1.43 (m, 9H), 2.78 (s, 3H), 2.81-3.01 (m, 1H), 3.15-3.26 (m, 1H), 3.79 (s, 3H), 4.31-4.45 (m, 2H), 3.65-3.70 (m, 1H), 4.89-5.05 (m, 2H), 5.55-5.67 (m, 1H), 6.71-6.80 and 6.93-7.05 (m, 2H), 7.26-7.33 (m, 5H). $^{13}$C-NMR (125 MHz, CDCl$_3$): 28.3, 33.4, 33.7, 53.1, 55.1, 60.8, 67.5, 68.0, 80.0, 113.9, 127.4, 127.8, 128.3, 128.8, 129.6, 129.7, 136.5, 137.0, 158.3, 170.1, 174.3. IR (neat) 3354.1, 2933.3, 1706.0, 1513.7, 1247.5, 1163.3, 1032. HRMS m/z cald for C$_{27}$H$_{34}$N$_2$O$_9$Na 553.2162 (M+Na). found 553.2176.

[Ser$^b$]-Tamandarin B Protected Linear Precursor (59): To a solution of 52 (117 mg, 0.18 mmol) in dioxane (5 mL), cooled to 0° C., was added a solution of HCl in dioxane (5 mL). The resulting solution was stirred at room temperature for 2 h. The solution was concentrated, and the residue diluted with CH$_2$Cl$_2$ and concentrated again to yield the hydrochloride salt 58 (90 mg, quantitative yield) as a white solid, which was used directly in the next step. To a mixture of hydrochloride salt 58 (90 mg, 0.15 mmol) HBTU (61 mg, 0.16 mmol), HOBt (20 mg, 0.15 mmol) and Tyr-ser acid 57 (80 mg, 0.15 mmol), cooled to −5° C. a solution of CH$_2$Cl$_2$/DMF 2/1 (3 mL) was added, the reaction was stirred 5 min and DIPEA (106 μL, 0.60 mmol) was added. The resulting solution was stirred at −5° C. overnight, diluted with $^t$BuOMe (10 mL), washed with 10% KHSO$_4$ (10 mL), NaHCO$_3$ (10 mL, sat), and NaCl (10 mL, sat), dried (Na$_2$SO$_4$), filtered, and concentrated. The crude oil was purified by column chromatography (silica gel, grad EtOAc/Hexanes 1/1) to CH$_2$Cl$_2$). $^1$H-NMR (500 MHz, CDCl$_3$): 0.88-1.00 (m, 18H), 1.47 (s, 9H), 1.49-1.52 (m, 4H), 2.03-2.06 (m, 5H), 2.22-2.25 (m, 3H), 2.55-2.60 (m, 1H), 2.70-2.84 (m, 3H), 2.98-3.03 (m, 1H), 3.27 (dt, J=5.8 and 20.0 Hz, 1H), 3.80 (s, 3H), 4.12-4.15 (m, 1H), 4.50-4.53 (m, 3H), 4.53-4.59 (m, 2H), 5.00-5.23 (m, 6H), 5.80-5.83 (m, 1H), 6.78-6.80 (m, 3H), 7.06-7.08 (m, 3H), 7.29-7.38 (m, 11H). $^{13}$C-NMR (125 MHz, CDCl$_3$): 14.5, 17.3, 18.6, 20.2, 21.0, 23.3, 24.6, 24.8, 27.8, 28.2, 28.8, 30.3, 32.5, 33.8, 38.8, 46.8, 48.4, 55.1, 58.9, 60.3, 60.5, 61.0, 64.3. 66.9, 67.2, 68.5, 78.1, 78.5, 79.3, 113.8, 127.5, 127.9, 128.1, 128.3, 128.5, 128.8, 129.7, 135.3, 136.5, 156.7, 157.5, 158.2, 167.3, 168.0, 169.6, 170.7, 171.3. IR (neat) 3315.5, 2968.3, 1744.0, 1670.0, 1637.7, 1513.9, 1447.3, 1170.6. HRMS m/z cald for C$_{57}$H$_{79}$N$_5$O$_{15}$Na 1096.5470 (M+Na): found 1096.5498.

[Ser$^b$]-Tamandarin B macrocycle (61): To a solution of protected linear precursor 59 (206 mg, 0.19 mmol) in MeOH (15 mL) under argon, Pd(OH)$_2$ (81 mg) was added. The reaction was purged with H$_2$ and stirred overnight under H$_2$ atmosphere (1 atm). The mixture was filtered through Celite®. The filtrate was concentrated to yield the free linear precursor 60 (150 mg, 91%) as a yellow oil, which was used in the next step without purification. The crude amino acid linear precursor 60 (150 mg, 0.17 mmol) was dissolved in CH$_3$CN (30 mL) and cooled to 0° C. HATU (160 mg, 0.42 mmol) was added followed by the dropwise addition of NNM (38 μL, 0.34 mmol). The reaction mixture was stirred at 0° C. for 1 h and then overnight. The reaction mixture was concentrated in vacuo, diluted with EtOAc (15 mL), washed with 10% KHSO$_4$ (10 mL), 5% NaHCO$_3$ (10 mL) and NaCl (10 mL, sat), dried (Na$_2$SO$_4$), filtered, and concentrated. The crude oil was purified by column chromatography (silica gel, EtOAc/Hexanes 2/1) to yield protected macrocycle 61 (130 mg, 89%) as a white foam. R$_f$ 0.23 (AcOEt/Hexanes 1/2). [α]$_D^{20}$=−56.1 (c=1, CHCl$_3$). $^1$H-NMR (500 MHz, CDCl$_3$): 0.89-1.05 (m, 18H), 1.45 (m, 9H), 1.62-1.74 (m, 1H), 2.00-2.20 (m, 4H), 2.55 (m, 3H), 2.81 (dd, 1H), 2.99 (dd, 1H), 3.15 (dd, 1H), 3.36 (dd, 1H), 3.53 (m, 1H), 3.67 (m, 1H), 3.73 (m, 1H), 3.80 (s, 3H), 3.91 (m, 1H), 4.10 (m, 1H), 4.19 (m, 1H), 4.42 (td, J=and, 1H), 4.48 (m, 1H), 4.51 (dd, J=and, 1H), 4.59 (m, 1H), 4.91 (m, 1H), 5.06 (m, 2H), 6.84 (d, 2H), 7.01 (d, 2H), 7.77 (d, 2H), 8.55 (d, 2H). $^{13}$C-NMR (125 MHz, CDCl$_3$): 17.4, 17.8, 18.7, 20.2, 20.6, 21.4, 23.5, 24.9, 25.1, 26.0, 28.0, 28.1, 28.3, 28.6, 28.8, 30.2, 30.7, 34.1, 38.6, 46.1, 47.0, 48.7, 48.9, 52.4, 55.3, 57.2, 62.9, 63.7, 65.6, 68.7, 69.3, 78.7, 80.5, 114.1, 129.8, 130.3, 155.6, 158.6, 169.1, 170.8, 171.1, 171.2. IR (neat) 3314.2, 2924.3, 2359.9, 1742.6, 1630.7. HRMS m/z cald for C$_{57}$H$_{79}$N$_5$O$_{15}$Na 1096.5470 (M+Na). found 1096.5498.

[N-Ser$^6$]-Tamandarin B (62): To a solution of Boc protected macrocycle 61 (20 mg, 0.024 mmol) in HPLC dioxane (10 mL) was added a solution of HCl in dioxane (10 mL). The resulting solution was stirred at room temperature for 2 h. The solution was concentrated and the residue diluted with CH$_2$Cl$_2$ and concentrated again to yield the hydrochloride salt (18 mg, quantitative yield) as a white solid, which was used directly in the next step. To a mixture of the macrocycle amine salt (18 mg, 0.023 mmol) and side chain (11 mg, 0.035 mmol) in CH$_2$Cl$_2$ (3 mL) at 0° C. was added BOP (15 mg, 0.035 mmol) and NMM (10 μL, 0.092 mmol). After 30 min at 0° C., the mixture was stirred at rt overnight The reaction was treated with sat NaCl solution (2 mL) and extracted with EtOAc (2×10 mL) The organic layers were washed with 10% HCl (5 mL), 5% NaHCO$_3$ (5 mL) and NaCl (5 mL, sat), dried (Na$_2$SO$_4$), filtered and concentrated. The crude oil (24 mg) was purified by HPLC. $^1$H-NMR (300 MHz, CDCl$_3$): δ 0.82-0.96 (m, 24H), 1.09-1.28 (m, 14H), 1.39-1.43 (m, 3H), 1.64 (m, 2H), 1.88-1.98 (m, 2H), 2.10-2.15 (m, 2H), 2.58 (s, 3H), 2.90-2.95 (m, 1H), 3.05 (s, 3H), 3.09-3.12 (m, 1H), 3.35-3.43 (m, 1H), 3.43-3.82 (m, 5H), 3.79 (s, 3H), 3.98-4.05 (m, 1H), 4.12-4.17 (m, 1H), 4.45-4.50 (m, 1H), 4.62-4.66 (m, 1H), 4.67-4.70 (m, 2H), 5.05 (d, J=5.3, 1H), 5.29-5.32 (m, 2H), 6.80 (d, J=8.7 Hz, 2H), 7.02 (d, J=8.6 Hz, 2H), 7.65 (d, J=6.7 Hz, 1H), 8.09 (d, J=9.5 Hz, 1H), 8.45 (d, J=8.9 Hz, 1H). HRMS m/z cald for C$_{52}$H$_{81}$N$_7$O$_{14}$Na (M+Na): 1050.5739 found 1050.5731.

Example 5
Synthesis of Ser$^6$ Pyr Tamandarin B

A serine-pyruvate analog of tamandarin (Ser$^6$ Pyr Tamandarin B) was prepared as shown in Scheme 17.

Scheme 17

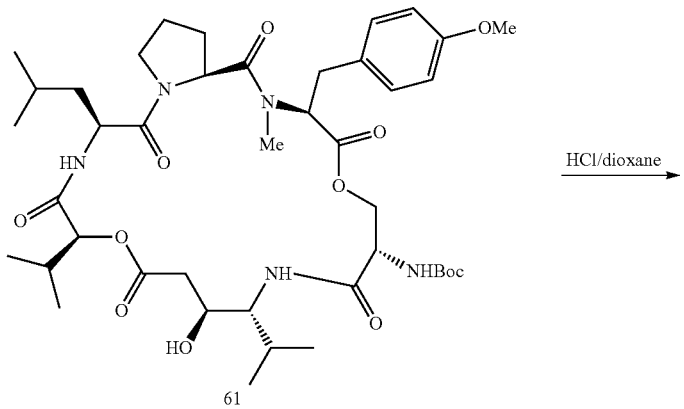

61

HCl/dioxane →

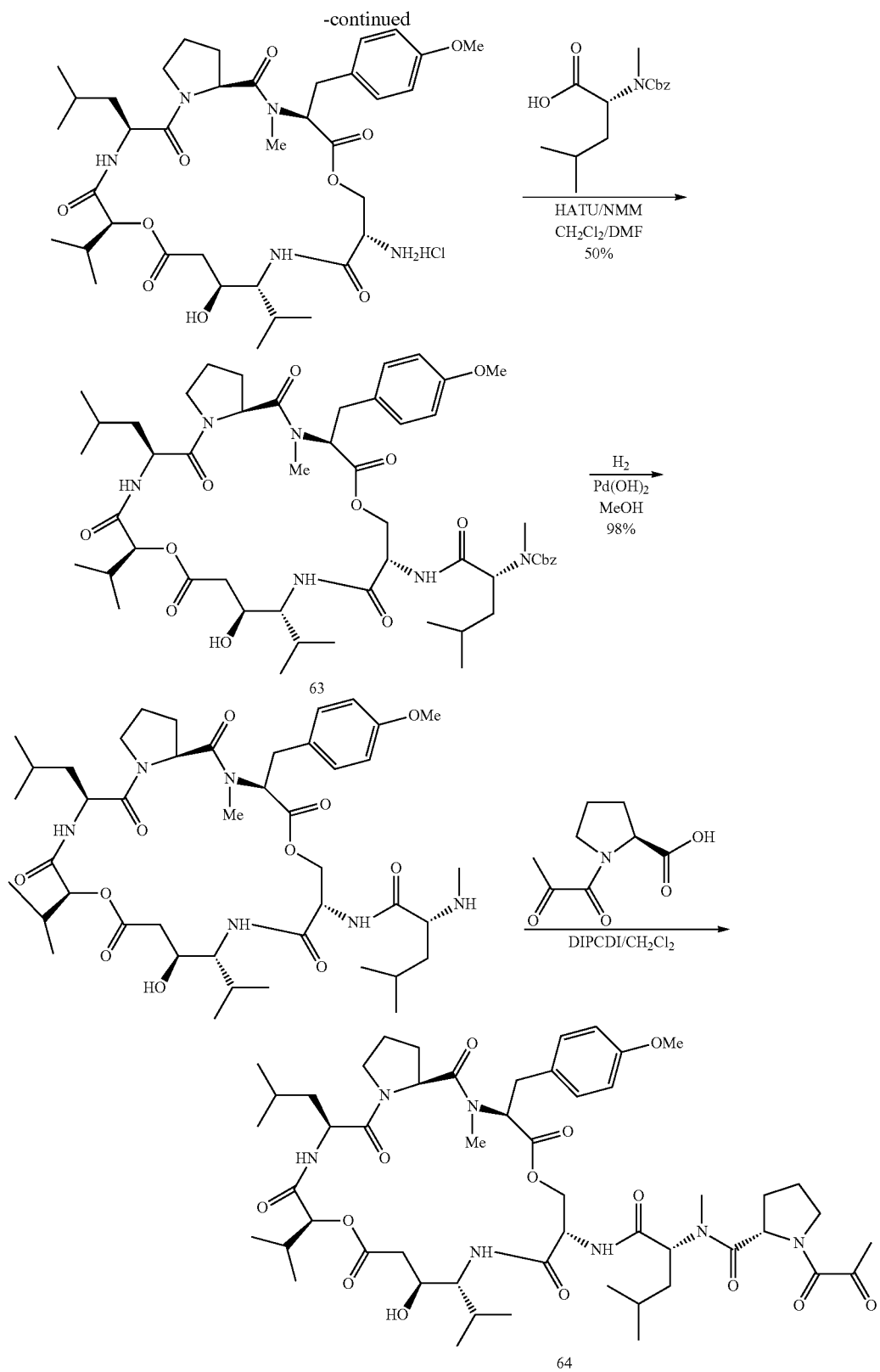
The N-Boc group of the Ser[6] tamandarin B macrocycle was removed using HCl (gaseous) in dioxane. Subsequent coupling with D-Cbz-N-Me-Leu using HATU and NMM in DMF/DCM afforded the depsipeptide 63 in 50% yield. Hydrogenolysis of the CBz group and coupling with the prolyl-pyruvyl fragment, using conditions as described herein, afforded the desired analog 64.

Example 6
Synthesis of Ala[4] Tamandarin B
An alanine analog of tamandarin B (Ala[4] Tamandarin B) was synthesized as shown in Schemes 18-20.
Scheme 18
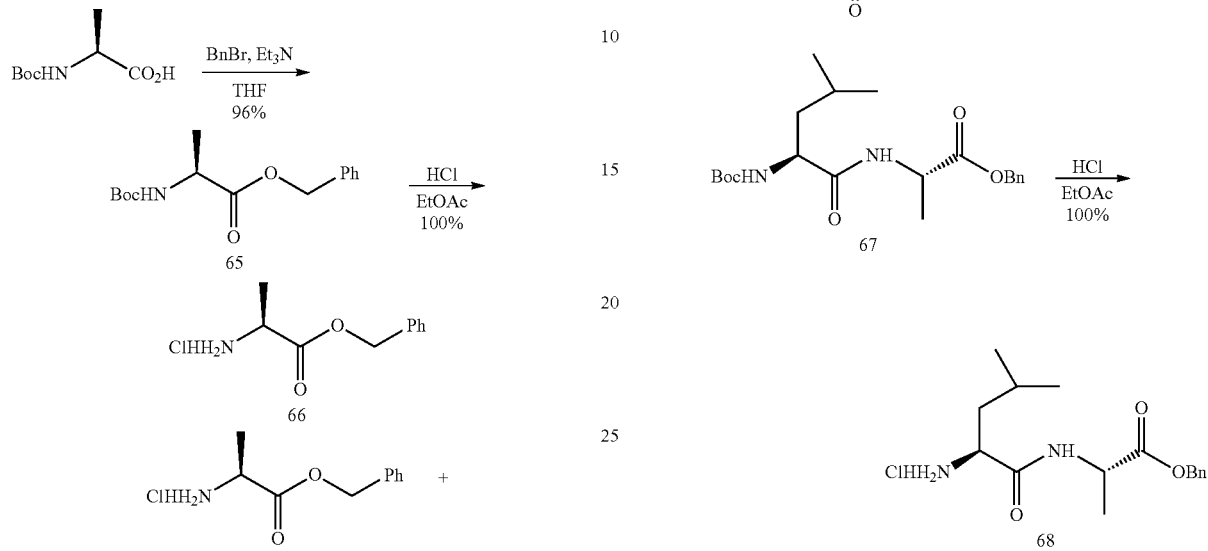
Scheme 19
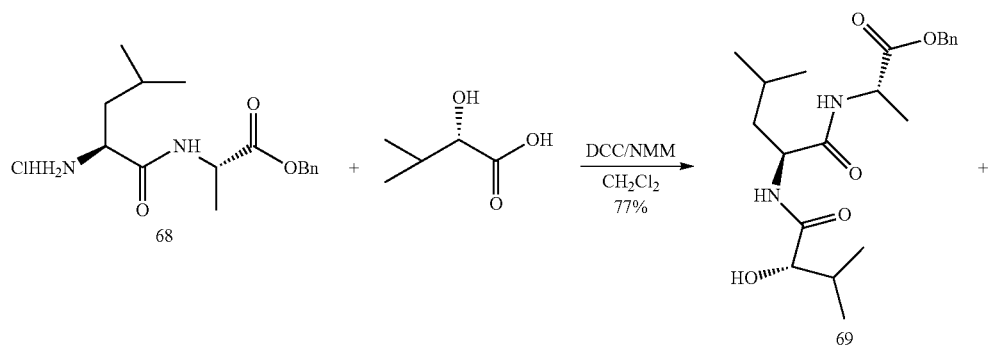
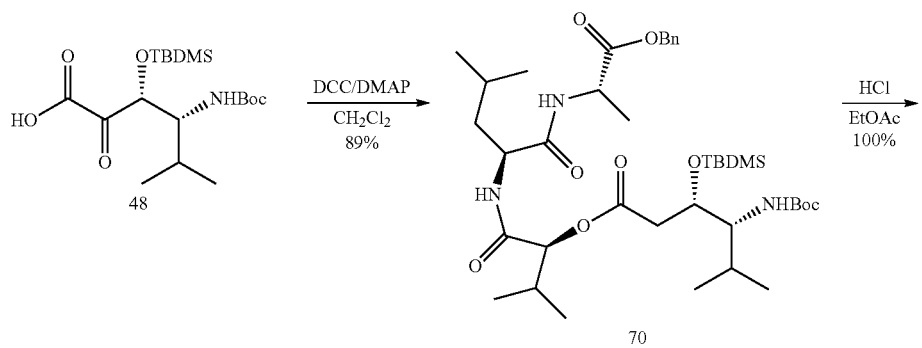

-continued
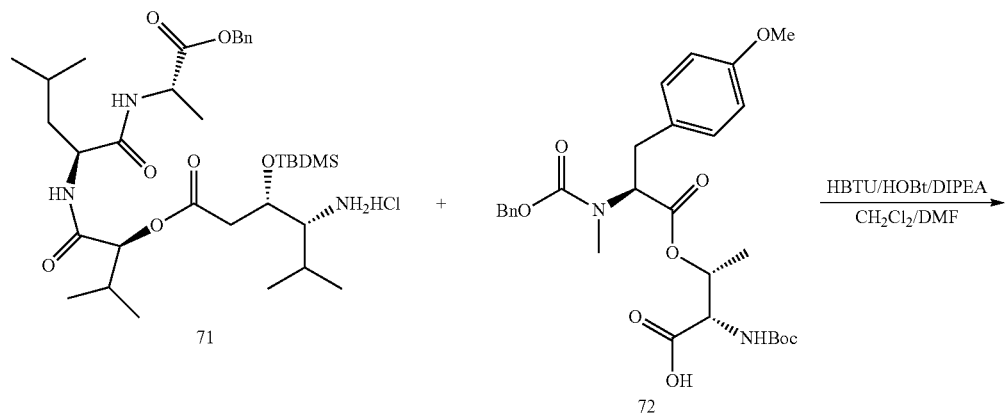
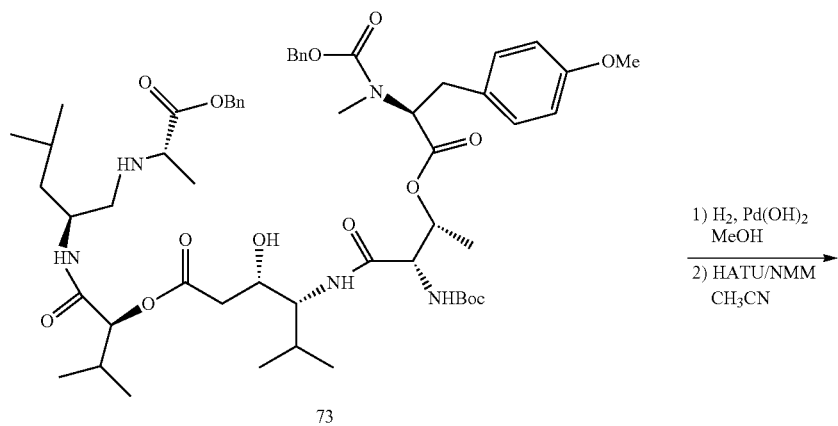
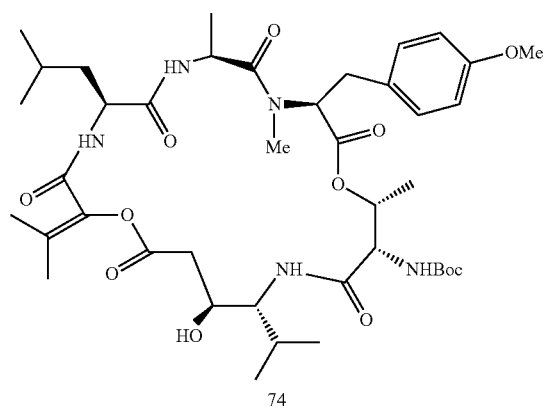

Scheme 20

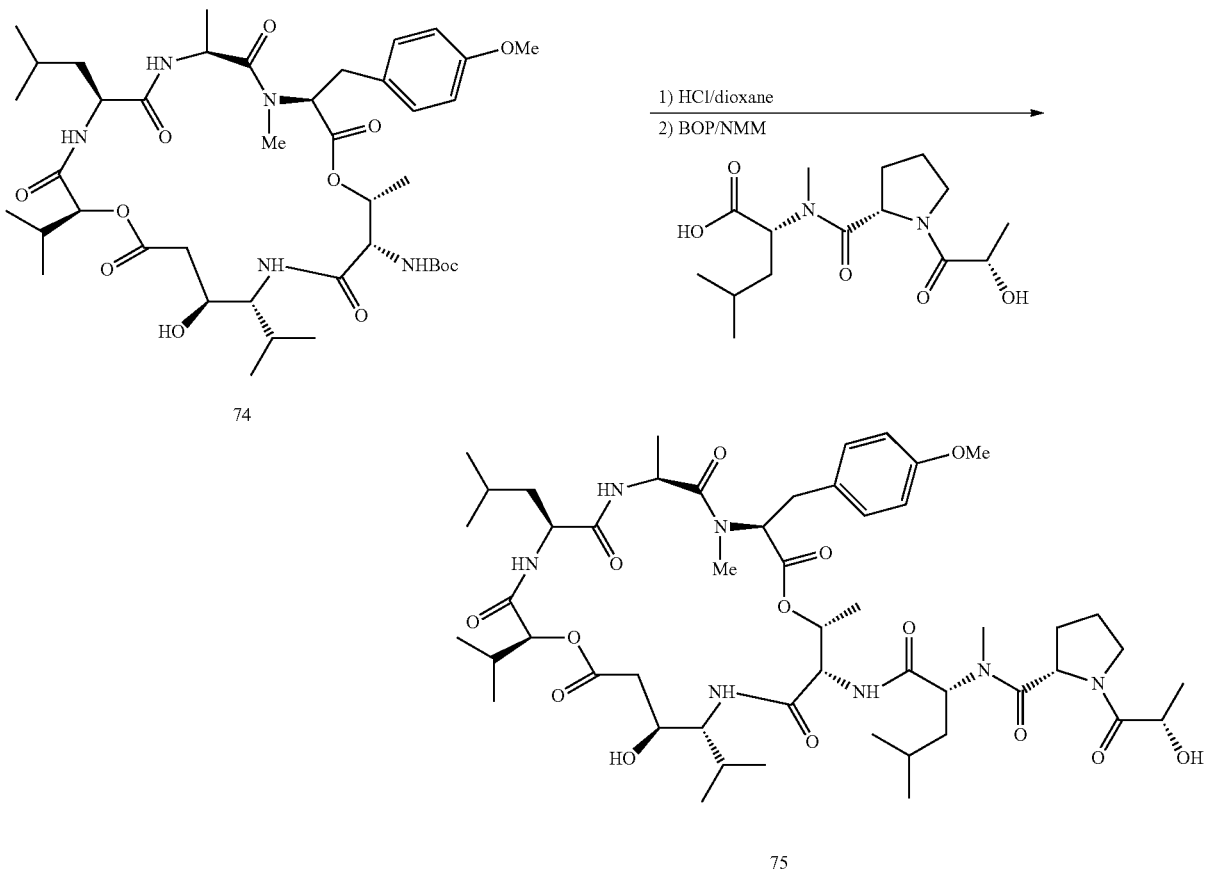

N-Boc-L-Leucyl-N-L-Alanine Acid Benzyl Ester (67): To a solution of N-Boc-L-alanine acid benzyl ester (66) (660 mg, 2.36 mmol) in HPLC EtOAc (10 mL) a saturated solution of HCl in EtOAc (5 mL) was added. The resulting solution was stirred at room temperature for 2 h. The solution was concentrated and the residue diluted with $CH_2Cl_2$ and concentrated again to yield the hydrochloride salt (quantitative yield) as a white solid, which was used directly in the next step. To a solution of hydrochloride salt (500 mg, 2.78 mmol) in $CH_2Cl_2$ (6 mL), cooled to 0° C., NMM (423 µL, 4.17 mmol) was added. After 15 min, N-Boc-L-leucine monohydrate (693 mg, 2.78 mmol), HOBt (425 mg, 2.78 mmol) and DCC (630 mg, 3.05 mmol) were added. The reaction mixture was stirred 14 h at room temperature diluted with $CH_2Cl_2$ (25 mL) and filtered. The resulting solution was washed with HCl 1N (20 mL), $NaHCO_3$ (20 mL, sat) and brine (20 mL), dried ($Na_2SO_4$), filtered and concentrated. The crude oil was purified by column chromatography (silica gel, grad EtOAc/Hexanes 1/6) to yield 67 (650 mg, 78%). $^1$H-NMR (500 MHz, $CDCl_3$): 0.99-1.01 (m, 6H), 1.43 (d, J=6.8 Hz, 3H), 1.44 (s, 9H), 1.45-1.75 (m, 3H), 4.15-4.25 (m, 1H), 4.55-4.66 (m, 1H), 5.00-5.25 (m, 2H), 5.45-5.53 (m, 1H), 7.29-1.34 (m, 5H). $^{13}$C-NMR (125 MHz, $CDCl_3$): 21.5, 24.1, 28.05, 41.2, 47.7, 52.5, 66.6, 79.3, 82.2, 127.8, 128.1, 128.5, 135.2, 155.6, 172.2, 172.6.

N-Hydroxyvaleryl-N-Leucyl-Alanine Acid Benzyl Ester (69): To a solution of 67 (625 mg) in HPLC AcOEt (10 mL) a saturated solution of HCl in AcOEt (5 mL) was added. The resulting solution was stirred at room temperature for 2 h. The solution was concentrated and the residue diluted with $CH_2Cl_2$ and concentrated again to afford the hydrochloride salt 68 (quantitative yield) as a white solid, which was used directly in the next step. To a solution of the hydrochloride salt 68 (522 mg, 1.59 mmol) in $CH_2Cl_2$ (6 mL), cooled to 0° C., NMM (197 µL, 1.75 mmol) was added. After 15 min α-hydroxyvaleric acid (187 mg, 1.59 mmol) and DCC (360 mg, 1.75 mmol) were added in portions. The reaction mixture was stirred 14 h at room temperature diluted with $CH_2Cl_2$ (25 mL) and washed with HCl 1N (20 mL), $NaHCO_3$ (20 mL, sat) and brine (20 mL), dried ($Na_2SO_4$), filtered and concentrated. The crude oil was purified by column chromatography (silica gel, EtOAc/Hexanes 1/1) to yield 69 (480 mg, 77%) as a white solid. $R_f$=0.31 (EtOAc/Hexanes 1/1). $[α]_D^{20}$=−45.3 (c=1, $CH_2Cl_2$). $^1$H-NMR (500 MHz, $CDCl_3$): 0.82 (d, J=6.8 Hz, 3H), 0.86 (d, J=6.1 Hz, 3H), 0.90 (d, J=6.1 Hz, 3H), 0.99 (d, J=6.8 Hz, 3H), 1.36 (d, J=7.1 Hz, 3H), 1.57-1.63 (m, 3H), 1.89-1.93 (m, 1H), 2.02-2.16 (m, 1H), 3.95-3.97 (m, 1H), 4.49-4.96 (m, 2H), 5.13 (c, J=12.3, 2H), 7.03 (d, J=7.0 Hz, 1H), 7.18 (d, J=8.5 Hz, 1H), 7.30-7.35 (m, 5H). $^{13}$C-NMR (125 MHz, $CDCl_3$): 15.5, 17.8, 19.1, 21.7, 22.8, 24.6, 31.6, 33.8, 40.9, 51.1, 67.1, 76.2, 128.1, 128.3, 168.6, 135.3, 172.1, 172.8, 173.8.

(3S,4R)-4-tert-Butoxycarbonylamino-5-methyl-3-(tert-butyl-dimethylsilanyloxy)-hexanoic Acid N-Hydroxyvaleryl-N-Leucyl-O-Benzylalanine Ester (70): To a solution of peptide 69 (200 mg, 0.51 mmol) in $CH_2Cl_2$ (4 mL), cooled to −5° C., DMAP (18.4 mg, 0.15 mmol) acid 48 (229 mg, 0.61 mmol) and DCC (157 mg, 0.76 mmol) were added in portions. The reaction mixture was stirred 7 h at −5° C., filtered and evaporated. The residue was dissolved in $CH_3CN$ (7 mL), filtered again, and evaporated. The crude oil was dissolved in EtOAc (10 mL) and washed with 10% $KHSO_4$ (10 mL), $NaHCO_3$ (10 mL, sat) and NaCl (10 mL, sat). The organic layer was dried ($Na_2SO_4$), and the solvent evaporated. The crude oil was purified by column chromatography (silica gel, grad EtOAc/Hexanes 1/4) to yield 70 (340 mg, 89%) as white foam. $R_f$ 0.72 (AcOEt/Hexanes 1:1). $[\alpha]_D^{20}$=−50.4 (c=1, $CH_2Cl_2$). $^1$H-NMR (500 MHz, $CDCl_3$): mixture of rotamers 0.05 (s, 6H), 0.77-1.04 (m, 27H), 1.30 and 1.39 (d, J=6.7 Hz, 3H), 1.42 and 1.52 (s, 9H), 1.30-1.70 (m, 5H), 2.56-2.70 (m, 2H), 3.19-3.22 (m, 1H), 3.41-3.47 (m, 1H), 3.83-3.85 (m, 1H), 3.99-4.03 (m, 1H), 4.30-4.32 (m, 2H), 4.35-4.38 (m, 1H), 4.48-4.53 (m, 1H), 4.67-4.70 (m, 1H), 4.73-4.75 (m, 1H), 4.82-4.85 (m, 1H), 4.99-5.13 (m, 2H), 5.15-5.21 (m, 2H), 6.33 (d, J=7.2 Hz, 1H), 7.18-7.30 (m, 5H), 8.39 (d, J=8.0 Hz, 1H). $^{13}$C-NMR (125 MHz, $CDCl_3$): −5.1, −4.8, 14.6, 17.2, 17.6, 17.9, 18.6, 20.3, 21.2, 22.8, 22.9, 24.5, 24.6, 24.8, 25.3, 25.6, 28.1, 28.2, 34.8, 39.6, 48.0, 48.3, 50.8, 50.9, 55.5, 63.1, 66.6, 70.1, 71.3, 78.9, 79.5, 82.1, 127.9, 128.0, 128.3, 135.4, 156.1, 157.3, 169.6, 170.0, 170.5, 170.9, 171.5, 172.2, 172.6, 172.9. HRMS m/z cald for $C_{39}H_{67}N_3O_9SiNa$ (M+Na): 772.4544 found 772.4551.

[Ala$^4$]-Tamandarin B Protected Linear Precursor (73): To a solution of 70 (80 mg, 0.10 mmol) in dioxane (2 mL), cooled to 0° C., was added a solution of HCl in dioxane (2 mL). The resulting solution was stirred at room temperature for 2 h. The solution was concentrated and the residue diluted with $CH_2Cl_2$ and concentrated again to yield the hydrochloride salt 71 (61 mg, quantitative yield) as a white solid, which was used directly in the next step. To a mixture of hydrochloride salt (61 mg, 0.10 mmol) HBTU (41.7 mg, 0.11 mmol), HOBt (13.5 mg, 0.10 mmol) and Tyr-Thr acid 72 (54 mg, 0.10 mmol), cooled to −5° C., a solution of $CH_2Cl_2$/DMF 2/1 (3 mL) was added, the reaction was stirred 5 min and DIPEA (71 μL, 0.40 mmol) was added. The resulting solution was stirred at −5° C. overnight, diluted with $^t$BuOMe (10 mL) and washed with 10% $KHSO_4$ (10 mL), $NaHCO_3$ (10 mL, sat) and NaCl (10 mL, sat), dried ($Na_2SO_4$), filtered and concentrated. The crude oil was purified by column chromatography (silica gel, grad EtOAc/Hexanes 1/1) to yield 73 (98 mg, 86%). $R_f$ 0.38 (AcOEt/Hexanes 1:1). $[\alpha]_D^{20}$=−34.4 (c=1, $CH_2Cl_2$). $^1$H-NMR (500 MHz, $CDCl_3$): 0.88-1.02 (m, 18H), 1.19 (d, J=6.9 Hz, 3H), 1.26 (d, J=6.9 Hz, 3H), 1.48 (s, 9H), 1.55-1.62 (m, 4H), 1.87-1.95 (m, 2H), 2.22-2.45 (m, 2H), 2.55-2.70 (m, 3H), 2.84 (s, 3H), 2.97-3.05 (m, 1H), 3.11-3.19 (m, 1H), 3.81 (s, 3H), 4.12-4.35 (m, 2H), 4.41-4.48 (m, 1H), 4.55-4.58 (m, 1H), 4.63-4.66 (m, 1H), 5.00-5.20 (m, 6H), 5.30-5.33 (m, 1H), 5.62 (d, J=7.3 Hz, 1H), 6.77 (d, J=8.3 Hz, 2H), 6.98 (m, 1H), 7.06 (d, J=7.3 Hz, 1H), 7.19 (m, 1H), 7.29-7.42 (m, 10H), 7.60-7.66 (m, 1H). $^{13}$C-NMR (125 MHz, $CDCl_3$): 16.2, 16.9, 17.6, 18.7, 20.1, 23.1, 24.5, 24.8, 25.5, 26.9, 28.1, 28.2, 30.2, 32.3, 33.8, 34.0, 37.9, 39.8, 48.2, 51.1, 55.2, 57.5, 60.6, 61.1, 66.9, 67.5, 69.1, 70.0, 78.1, 80.3, 113.9, 127.5, 128.0, 128.3, 128.4, 128.5, 129.8, 131.5, 136.2, 156.9, 158.4, 170.1, 170.9, 171.2, 171.9, 172.4. IR (neat) 3297.6, 2962.0, 1744.0, 1658.8, 1514.2, 1166.6. HRMS m/z cald for $C_{57}H_{79}N_5O_{15}Na$ 1096.5470 (M+Na). found 1096.5498.

[Ala$^4$]-Tamandarin B macrocycle (74): To a solution of protected linear precursor 73 (102 mg, 0.09 mmol) in MeOH (88 mL), under argon, Pd(OH)$_2$ (44 mg) was added. The reaction was purged with H$_2$ and stirred overnight under H$_2$ atmosphere (1 atm). The mixture was filtered through Celite and the filtrate was concentrated to yield the free liner precursor 14 (77 mg, 96%) as a yellow oil. The crude amino acid linear precursor (77 mg, 0.91 mmol) was dissolved in $CH_3CN$ (20 mL) and cooled to 0° C. HATU (815 mg, 0.22 mmol) was added followed by the dropwise addition of NNM (20 μL, 1.82 mmol). The reaction was stirred at 0° C. for 1 h and then overnight. The reaction mixture was concentrated in vacuo, diluted with EtOAc (15 mL), and washed 10% $KHSO_4$. (15 mL), 5% $NaHCO_3$ (15 mL) and NaCl (15 mL, sat), dried ($Na_2SO_4$), filtered, and concentrated. The crude oil was purified by column chromatography (silica gel, EtOAc/Hexanes 2/1) to yield protected macrocycle 74 (45 mg, 60%) as white foam. $R_f$ 0.24 (AcOEt/Hexanes 1/2). $[\alpha]_D^{20}$=−33.09 (c=1, $CHCl_3$). $^1$H-NMR (500 MHz, $CDCl_3$): 0.92-1.04 (m, 18H), 1.16 (d, J=6.8 Hz, 3H), 1.17-1.30 (m, 3H), 1.49 (s, 9H), 1.51-1.61 (m, 1H), 1.73-1.75 (m, 1H), 1.83-1.86 (m, 1H), 1.93-1.97 (m, 1H), 2.30-2.40 (m, 1H), 2.57-2.39 (m, 1H), 3.00-3.05 (m, 1H), 3.08 (s, 3H); 3.19-3.21 (m, 1H), 3.49-3.51 (m, 1H), 3.82 (s, 3H), 3.98-4.00 (m, 1H), 5.01-5.06 (m, 2H), 5.27-5.30 (m, 1H), 5.56-5.66 (m, 1H), 6.67-6.69 (m, 1H), 6.88 (d, J=7.9 Hz, 2H), 7.00-7.09 (m, 1H), 7.12 (d, 2H). $^{13}$C-NMR (125 MHz, $CDCl_3$): 15.1, 18.4, 18.9, 20.9, 21.1, 23.2, 24.0, 24.8, 24.9, 25.5, 28.0, 28.1, 30.1, 33.7, 34.4, 39.01, 39.3, 45.4, 47.1, 51.2, 55.3, 69.3, 71.9, 79.5, 80.6, 114.1, 114.2, 129.9, 132.3, 156.1, 169.01, 170.9, 171.5, 172.3, 173.2. HRMS m/z cald for $C_{41}H_{65}N_5O_{12}Na$ 842.4527 (M+Na). found 842.4545.

[N-Ala$^4$]-Tamandarin B (75): To a solution of Boc protected macrocycle 74 (11 mg, 0.013 mmol) in HPLC dioxane (5 mL) was added a solution of HCl in dioxane (5 mL). The resulting solution was stirred at room temperature for 4 h. The solution was concentrated, and the residue diluted with $CH_2Cl_2$ and concentrated again to yield the hydrochloride salt (quantitative yield) as a white solid, which was used directly in the next step. To a mixture of the macrocycle amine salt (10 mg, 0.013 mmol) and side chain (6.2 mg, 0.019 mmol) in $CH_2Cl_2$ (2 mL) at 0° C. was added BOP (8.4 mg, 0.019 mmol) and NMM (6 μL, 0.052 mmol). After 30 min at 0° C., the reaction was stirred at rt overnight. The reaction was treated with NaCl solution (5 mL, sat) and extracted with EtOAc (2×10 mL). The organic layers were washed with 10% HCl (5 mL), 5% $NaHCO_3$ (5 mL) and NaCl (5 mL, sat), dried ($Na_2SO_4$), filtered and concentrated. The crude oil (10 mg, 77%) was purified by HPLC. $^1$H-NMR (300 MHz, $CDCl_3$): δ 0.82-1.46 (m, 32H), 1.46-2.10 (m, 12H), 2.16 (m, 4H), 2.65 (m, 1H), 2.82-3.01 (m, 1H), 3.05 (s, 3H), 3.20 (s, 3H), 3.49-3.55 (m, 2H), 3.63-3.92 (m, 5H), 3.85 (s, 3H), 4.09 (m, 1H), 4.32-4.43 (m, 2H), 4.60-4.65 (m, 1H), 4.75 (t, J=6.7, 1H), 4.88 (t, J=8.0, 1H), 5.01 (d, J=5.3, 1H), 5.24 (s, 2H), 6.64-6.66 (m, 1H), 6.85 (d, J=8.7 Hz, 2H), 7.14 (d, J=8.8 Hz, 2H), 7.22-7.23 (m, 1H). MS Calcd for $C_{51}H_{81}N_7O_{14}$: 1016.2. Found: 1016.4 (M+H)$^+$.

Example 7

Synthesis of L-Me-Ala$^4$ Tamandarin B

A L-methylalanine analog of tamandarin B (L-Me-Ala$^4$ Tamandarin B) was synthesized as shown in Schemes 21 and 22. Compound 85 was then reacted to form the L-methylalaninine analog as described below.

Scheme 21
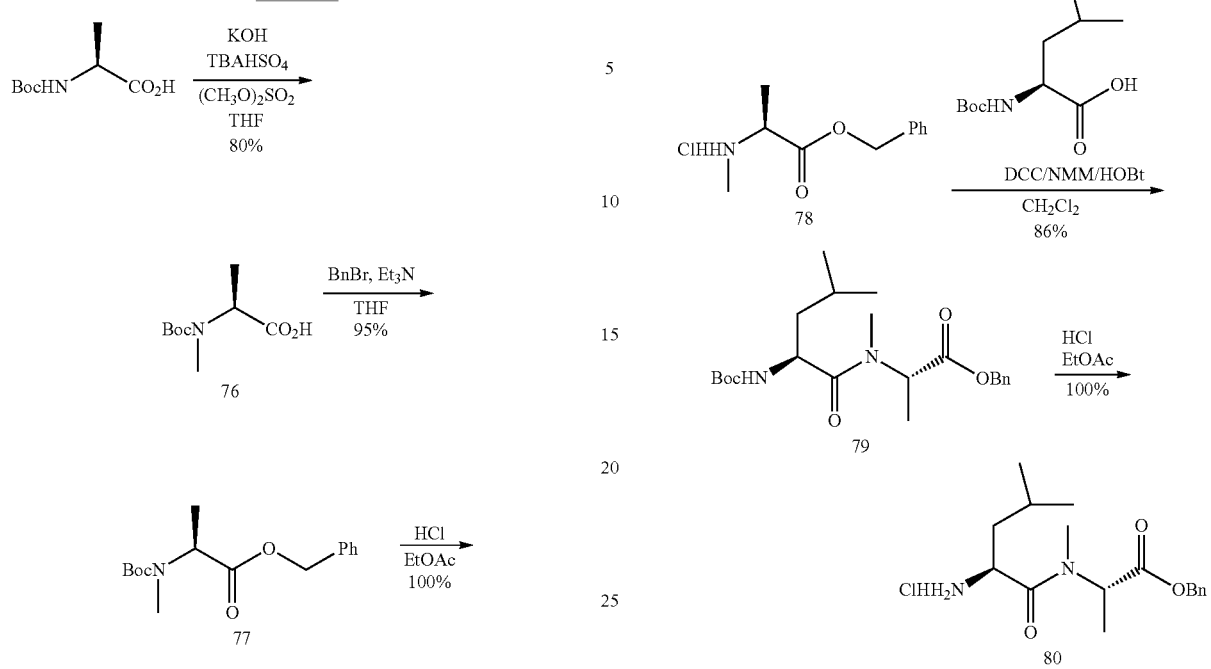
Scheme 22
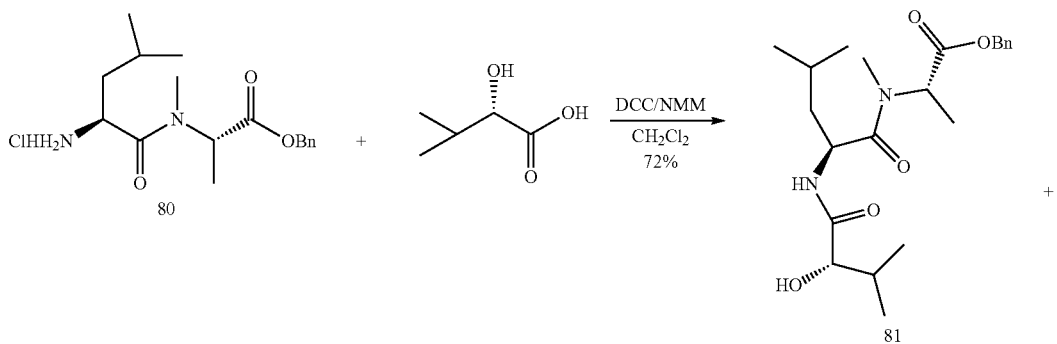
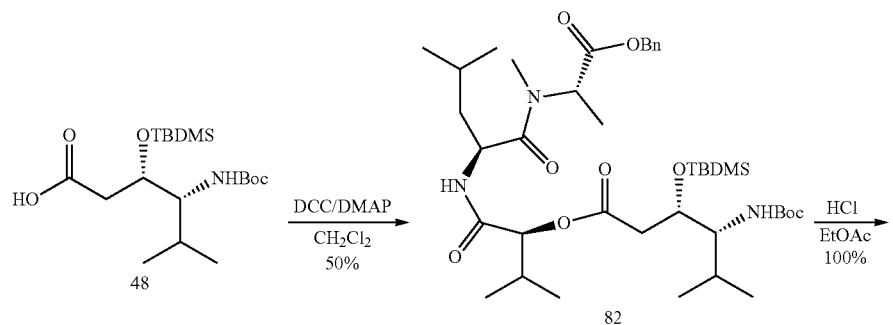

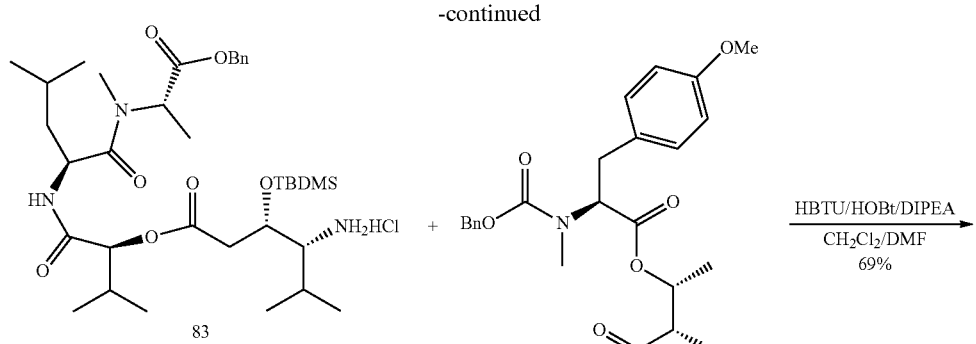

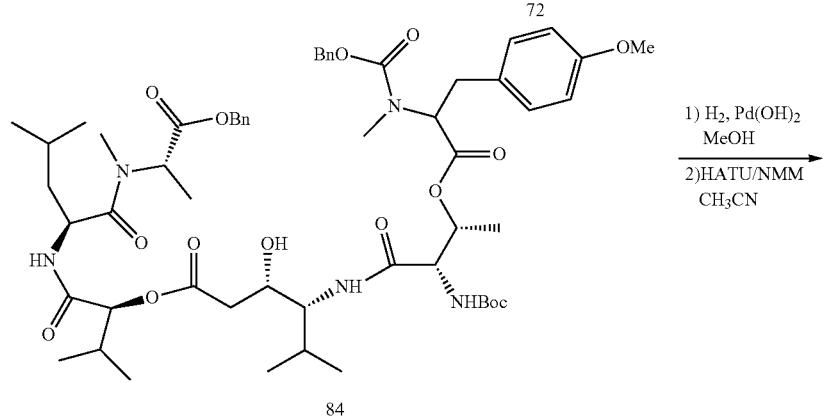

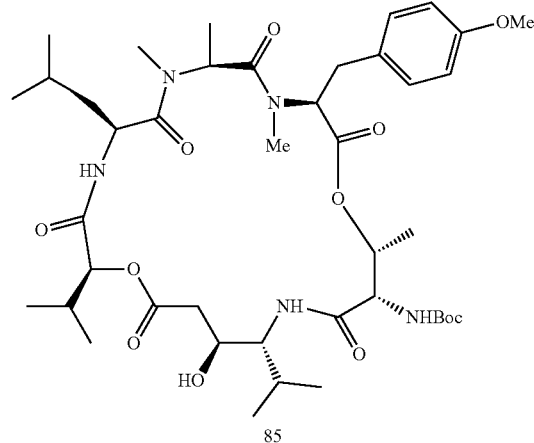

Boc-L-N-Methylalanine (76): To a solution stirred solution of L-Boc-alanine (5 g, 26.4 mmol) in THF (80 mL), at 0° C., finely powered KOH (10.4 g, 187 mmol) was added in portions, followed by the addition of tetrabutylammonium hydrogen sulfate (0.5 g, 10% by weight). Then, dimethyl sulfate (10 mL, 105 mmol) was added dropwise over 15 min. The reaction was stirred for an additional 30 min, and $H_2O$ (50 mL) was added. After stirring 5 h at room temperature, 20% aqueous ammonium hydroxide solution was added (20 mL). The reaction was diluted with ether (100 mL), the aqueous layer was separated, and the organic layer was extracted with saturated aqueous $NaHCO_3$ (2×40 mL). The combined aqueous layers were acidified to a pH of 1 with 1M $KHSO_4$ and extracted with EtOAc (2×200 mL). The organic layers were combined, dried ($Na_2SO_4$), filtered, and concentrated. The resulting acid 76 (4.3 g, 80%) was obtained as a yellow oil and used in the next step without purification. $^1$H-NMR (500 MHz, $CDCl_3$): 1.43-1.55 (m, 12H), 2.91 (br s, 3H), 4.54-4.58 (m, 1H), 4.89-4.93 (m, 1H).

N-Boc-L-N-Methylalanine Benzyl Ester (77): To a solution of L-Boc-N-methylalanine 76 (2.1 g, 10.3 mmol) in THF (10 mL), cooled to 0° C., $Et_3N$ (1.6 mL, 11.3 mmol) and benzyl bromide (1.3 mL, 11.3 mmol) were added. The mixture was stirred 18 h at room temperature, and the solvent was evaporated at reduced pressure. The residue was evaporated, diluted with $CH_2Cl_2$ (20 mL) and washed with HCl 1N (15 mL), $NaHCO_3$ sat (15 mL), and $H_2O$ (15 mL). The organic layers were combined, dried ($Na_2SO_4$), filtered and concentrated. The resulting ester 77 (2.25 g, 95%) was obtained as a yellow oil and used in the next step without purification. $^1$H-NMR (500 MHz, $CDCl_3$): 1.44-1.54 (m, 12H), 2.81 and 2.90 (br s, 3H), 4.49-4.53 (m, 1H), 4.83-4.89 (m, 1H), 5.18 (s, 2H), 7.27-7.43 (m, 5H).

N-Boc-L-Leucyl-L-N-Methylalanine Acid Benzyl Ester (79): To a solution of L-N-Boc-N-methylalanine benzyl ester (77) (320 mg, 1.09 mmol) in HPLC dioxane (8 mL) a saturated solution of HCl in dioxane (5 mL) was added. The resulting solution was stirred at room temperature for 2 h. The solution was concentrated and the residue diluted with $CH_2Cl_2$ and concentrated again to afford the hydrochloride salt (quantitative yield) as a white solid, which was used directly in the next step. To a solution of hydrochloride salt (250 mg, 1.09 mmol) in $CH_2Cl_2$ (10 mL) and DMF (5 mL), cooled to 0° C., NMM (221 µL, 2.08 mmol) was added. After 15 min, N-Boc-L-leucine monohydrate (246 mg, 0.99 mmol) and HATU (779 mg, 2.08 mmol) were added. The reaction mixture was stirred 14 h at room temperature and $CH_2Cl_2$ was evaporated. The resulting residue was diluted with ethyl ether (25 mL) and washed with HCl 1N (20 mL), $NaHCO_3$ sat (20 mL,) and brine (20 mL), dried ($Na_2SO_4$), filtered and concentrated. The crude oil was used without purification in the next step. $^1$H-NMR (500 MHz, $CDCl_3$): 0.91 (d, J=6.7 Hz, 3H), 0.99 (d, J=6.7 Hz, 3H), 1.48 (m, 13H), 1.69-1.78 (m, 2H), 3.01 (s, 3H), 4.60-4.71 (m, 1H), 5.10-5.29 (m, 3H), 5.35-5.48 (m, 1H), 7.31-7.42 (m, 5H). HRMS m/z cald for $C_{22}H_{34}N_2O_5Na$ (M+Na): 429.2365 found 429.2385.

N-Hydroxyvaleryl-N-L-Leucyl-N-L-Methylalanine Acid Benzyl Ester (81): To a solution of dipeptide 79 (360 mg) in HPLC dioxane (10 mL) a saturated solution of HCl in dioxane (6 mL) was added. The resulting solution was stirred at room temperature for 2 h. The solution was concentrated and the residue diluted with $CH_2Cl_2$ and concentrated again to afford the hydrochloride salt 80 (330 mg, quantitative yield) as a white solid, which was used directly in the next step. To a solution of the hydrochloride salt 80 (303 mg, 0.88 mmol) in $CH_2Cl_2$ (2 mL), cooled to 0° C., NMM (108 µL, 0.96 mmol) was added. After 15 min hydroxyvaleric acid (104 mg, 0.88 mmol) and DCC (200 mg, 0.96 mmol) were added in portions. The reaction mixture was stirred 14 h at room temperature, diluted with $CH_2Cl_2$ (20 mL), washed with HCl 1N (20 mL), $NaHCO_3$ (20 mL, sat), and brine (20 mL), dried ($Na_2SO_4$), filtered, and concentrated. The crude oil was purified by column chromatography (silica gel, EtOAc/Hexanes 2/1) to yield 81 (258 mg, 72%) as colorless oil. $R_f$ 0.30 (EtOAc/Hexanes 2/1). $[\alpha]_D^{20}$=−37.2 (c=1, $CH_2Cl_2$). $^1$H-NMR (500 MHz, $CDCl_3$): 0.87 (d, J=6.8 Hz, 3H), 0.89 (d, J=6.1 Hz, 3H), 0.90 (d, J=6.1 Hz, 3H), 1.03 (d, J=6.8 Hz, 3H), 1.42 (d, J=7.3 Hz, 3H), 1.55-1.66 (m, 1H), 1.66-1.76 (m, 1H), 2.14-2.20 (m, 1H), 3.02 (s, 3H), 3.98 (d, J=1 Hz, 1H), 4.98-5.02 (m, 1H), 5.17 (m, 2H), 5.37 (c, J=6.9 Hz, 2H), 7.29-7.40 (m, 5H). $^{13}$C-NMR (125 MHz, $CDCl_3$): 14.07, 15.5, 19.12, 21.5, 21.6, 23.1, 23.3, 24.6, 24.7, 25.4, 31.0, 31.7, 33.4, 41.3, 47.2. 52.3. 67.0. 76.1. 128.2. 128.4. 128.6, 135.3. 171.3. 173.3. 173.5. IR (neat) 3378.8, 2958.9, 1740.3, 1652.0, 1635.5, 1558.0, 1506.2, 1456.2, 1196.1, 1086.6. HRMS m/z cald for $C_{22}H_{34}N_2O_5Na$ (M+Na): 429.2365 found 429.2370.

(3S,4R)-4-tert-Butoxycarbonylamino-5-methyl-3-(tert-butyldimethyl-silanyloxy)hexanoic Acid N-Hydroxyvaleryl-N-L-leucyl-N-L-methylalanine Benzyl Ester (82): To a solution of peptide 81 (245 mg, 0.61 mmol) in $CH_2Cl_2$ (4 mL), cooled to −5° C., DMAP (22.4 mg, 0.15 mmol) acid 48 (271 mg, 0.72 mmol) and DCC (157 mg, 0.18 mmol) were added in portions. The reaction mixture was stirred 7 h at −5° C., filtered, and evaporated. The residue was dissolved in $CH_3CN$ (8 mL), filtered again, and evaporated. The crude oil was dissolved in EtOAc (15 mL) and washed with 10% $KHSO_4$ (15 mL), $NaHCO_3$ (15 mL, sat) and NaCl (15 mL, sat). The organic layer was dried ($Na_2SO_4$), and the solvent was evaporated. The crude oil was purified by column chromatography (silica gel, EtOAc/Hexanes 1/4) to yield 70 (325 mg, 70%) as white foam. $R_f$ 0.22 (AcOEt/Hexanes 4:1). $[\alpha]_D^{20}$=−33.6 (c=1, $CH_2Cl_2$). $^1$H-NMR (500 MHz, $CDCl_3$): mixture of rotamers 0.01 (s, 6H), 0.85-1.00 (m, 27H), 1.39 (d, J=6.7 Hz, 3H), 1.44 and 1.51 (s, 9H), 1.29-1.40 (m, 1H), 1.56-1.70 (m, 2H), 1.89-1.92 (m, 1H), 2.00-2.09 (m, 2H), 2.43-2.46 (m, 1H), 2.66-2.70 (m, 1H), 2.69-2.70 (m, 1H), 2.94 and 3.01 (s, 3H), 3.43-3.46 (m, 1H), 3.60-3.65 (m, 1H), 3.98-4.02 (m, 4H), 4.09-4.14 (m, 2H), 4.31 (d, J=7.8 Hz, 1H), 4.81-4.82 (m, 1H), 4.99-5.13 (m, 2H), 5.15-5.21 (m, 1H), 6.63 (d, J=7.2 Hz, 1H), 6.74 (d, J=5.2 Hz, 1H), 7.18-7.30 (m, 5H), 8.39 (d, J=6.5 Hz, 1H). $^{13}$C-NMR (125 MHz, $CDCl_3$): −5.0, −4.5, 13.9, 14.1, 14.7, 16.5, 17.6, 18.1, 18.5, 18.8, 20.4, 21.3, 21.5, 23.2, 24.6, 24.7, 25.7, 26.9, 27.7, 28.4, 30.1, 30.4, 30.7, 30.9, 39.3, 39.9, 41.8, 42.8, 47.0, 51.9, 52.3, 59.4, 60.2, 63.0, 66.7, 66.9, 70.1, 71.4, 78.9, 79.2, 79.4, 82.4, 128.08, 128.2, 128.3, 128.5, 135.4, 135.5, 156.2, 157.3, 169.1, 169.7, 170.8, 171.0, 171.2, 171.6, 172.5, 173.6. IR (neat) 2959.1, 1740.5, 1694.0, 1644.4, 1521.2, 1471.5, 1387.0, 1252.7 1166.6, 1086.1. HRMS m/z cald for $C_{40}H_{69}N_3O_9SiNa$ (M+Na): 786.4700 found 786.4707.

[N-Me-Ala$^4$]-Tamandarin B Protected Linear Precursor (84): To a solution of 82 (285 mg, 0.37 mmol) in dioxane (5 mL), cooled to 0° C., was added a solution of HCl in dioxane (5 mL). The resulting solution was stirred at room temperature for 2 h. The solution was concentrated, and the residue was diluted with $CH_2Cl_2$ and concentrated again to yield the hydrochloride salt 83 (218 mg, quantitative yield) as a white solid, which was used directly in the next step. To a mixture of hydrochloride salt 83 (218 mg, 0.37 mmol) HBTU (147.3 mg, 0.38 mmol), HOBt (50 mg, 0.37 mmol) and Tyr-Thr acid 72 (201 mg, 0.37 mmol), cooled to −5° C., a solution of $CH_2Cl_2$/DMF 2/1 (10 mL) was added, the reaction was stirred 5 min, and DIPEA (264 µL, 1.48 mmol) was added. The resulting solution was stirred at −5° C. overnight, diluted with t-BuOMe (25 mL), washed with 10% $KHSO_4$ (20 mL), $NaHCO_3$ (20 mL, sat) and NaCl (20 mL, sat), dried ($Na_2SO_4$), filtered and concentrated. The crude oil was purified by column chromatography (silica gel, grad EtOAc/Hexanes 1/1) to yield 84 (280 mg, 69%). $R_f$ 0.22 (AcOEt/Hexanes 1:1). $[\alpha]_D^{20}$=−45.8 (c=1, $CH_2Cl_2$). $^1$H-NMR (500 MHz, $CDCl_3$): 0.87-1.01 (m, 18H), 1.00-1.16 (m, 4H), 1.28 (d, J=6.9 Hz, 3H), 1.47 (s, 9H), 1.68-1.69 (m, 2H), 1.70-1.77 (m, 1H), 2.07-2.09 (m, 1H), 2.22-2.25 (m, 1H), 2.75-2.77 (m, 1H), 2.85, 2.87 (m, 1H), 2.88 (s, 3H), 2.98 (s, 3H), 3.23 (dd, J=7.3 and 14.3 Hz, 1H), 3.77 (s, 3H), 4.10-4.15 (m, 1H), 4.21-4.28 (m, 2H), 4.35-4.38 (m, 1H), 4.60-4.66 (m, 1H), 5.00-5.12 (m, 2H), 5.20-5.33 (m, 4H), 5.25-5.30 (m, 1H), 5.58 (d, J=7.3 Hz, 1H), 6.79 (d, J=8.3 Hz, 2H), 7.02 (m, 1H), 7.09 (d, J=7.3 Hz, 1H), 7.20 (m, 1H), 7.29-7.37 (m, 10H). $^{13}$C-NMR (125 MHz, $CDCl_3$): 14.4, 16.8, 17.8, 18.6, 19.0, 20.7, 21.7, 23.7, 25.1, 28.5, 28.6, 30.9, 31.3, 32.3, 34.5, 39.0, 41.1, 41.2, 47.6, 52.7, 55.6, 58.1, 61.2, 67.9, 69.2, 70.5, 71.0, 78.6, 81.1, 114.3, 128.05, 128.4, 128.6, 128.8, 129.0, 130.3, 135.7, 136.8, 156.1, 157.3, 158.8, 169.9, 170.4, 171.4, 171.6, 173.7. IR (neat) 3318.3, 2961.1, 2993.3, 1741.8, 1683.1, 1636.1, 1514.0, 1455.7, 1306.1, 1247.8, 1175.8. HRMS m/z cald for $C_{57}H_{81}N_5O_{15}Na$ 1098.2756 (M+Na). found 1098.5657.

[N-Me-Ala$^4$]-Tamandarin B macrocycle (85): To a solution of protected linear precursor 84 (280 mg, 0.33 mmol) in MeOH (20 mL), under argon, Pd(OH)$_2$ (100 mg) was added. The reaction was purged with $H_2$ and stirred overnight under $H_2$ atmosphere (1 atm). The mixture was filtered through Celite®, and the filtrate was concentrated to yield the free liner precursor (208 mg, 94%) as a yellow oil. The crude amino acid linear precursor (208 mg, 0.24 mmol) was dissolved in $CH_3CN$ (50 mL) and cooled to 0° C. HATU (219 mg, 0.57 mmol) was added followed by the dropwise addition of NNM (51 μL, 0.48 mmol). The reaction mixture was stirred at 0° C. for 1 h and then overnight. The reaction mixture was concentrated in vacuo, diluted with EtOAc (30 mL), washed 10% KHSO$_4$ (25 mL), 5% NaHCO$_3$ (25 mL) and NaCl (25 mL, sat), dried (Na$_2$SO$_4$), filtered, and concentrated. The crude oil was purified by column chromatography (silica gel, EtOAc/Hexanes 2/1) to yield protected macrocycle 85 (94 mg, 48%) as a white foam. R$_f$ 0.30 (AcOEt/Hexanes 1/2). [α]$_D^{20}$=−28.77 (c=1, CHCl$_3$). $^1$H-NMR (500 MHz, CDCl$_3$): 0.88-1.00 (m, 17H), 1.22-1.33 (m, 3H), 1.17-1.30 (m, 4H), 1.49 (s, 9H), 1.48-1.52 (m, 1H), 1.97-2.05 (m, 2H), 2.09-2.14 (m, 1H), 2.30-2.40 (m, 1H), 2.51 (dd, J=7.0 and 13.2 Hz, 1H), 2.59-2.61 (m, 2H), 2.80 and 2.91 (s, 3H), 2.88-2.91 (m, 1H), 3.09 and 3.15 (s, 3H), 3.10-3.15 (m, 1H), 3.28-3.33 (m, 1H), 3.49-3.51 (m, 1H), 3.75 and 3.78 (s, 3H), 4.12-4.13 (m, 1H), 4.22-4.23 (m, 1H), 4.51-4.52 (m, 1H), 4.92-4.93 (m, 1H), 4.94 (d, J=5.8 Hz, 1H), 4.98-5.05 (m, 2H), 5.19-5.21 (m, 1H), 5.25-5.27 (m, 1H), 6.80 (t, J=6.5 Hz, 2H), 7.03 (dd, J=8.5 and 11.7 Hz, 2H), 7.40 (d, J=8.6 Hz, 1H), 7.71 (d, J=9.2 Hz, 1H), 7.89 (d, J=8.1 Hz, 1H). $^{13}$C-NMR (125 MHz, CDCl$_3$): 14.1, 14.8, 15.5, 18.3, 18.8, 19.0, 19.4, 20.6, 23.8, 23.9, 25.0, 25.3, 28.4, 30.1, 30.2, 30.8, 30.9, 33.9, 34.8, 38.9, 39.3, 47.7, 48.2, 51.3, 55.6, 56.5, 62.0 66.6, 69.3, 69.5, 70.3, 71.5, 79.3, 80.9, 81.0, 114.4, 114.7, 128.4, 129.7, 130.2, 130.4, 130.8, 156.2, 156.4, 159.0, 159.2, 169.1, 170.0, 170.2, 171.4, 171.8, 172.0, 172.9, 174.1, 174.3. IR (neat) 3334.2, 2960.5, 1745.1, 1658.6, 1961.2, 1514.1, 1248.5, 1164.1, 1082.6. HRMS m/z cald for C$_{42}$H$_{67}$N$_5$O$_{12}$Na 856.4683 (M+Na). found 856.4617.

[N-Me-Ala$^4$]-Tamandarin B (120): To a solution of Boc protected macrocycle 85 (15 mg, 0.018 mmol) in HPLC dioxane (5 mL) was added a solution of HCl in dioxane (5 mL). The resulting solution was stirred at room temperature for 4 h. The solution was concentrated, and the residue was diluted with CH$_2$Cl$_2$ and concentrated again to yield the hydrochloride salt (14 mg, quantitative yield) as a white solid, which was used directly in the next step. To a mixture of the macrocycle amine salt (14 mg, 0.018 mmol) and side chain (10 mg, 0.031 mmol) in CH$_2$Cl$_2$ (3 mL) at 0° C. was added BOP (14 mg, 0.031 mmol) and NMM (9 μL, 0.72 mmol). After 30 min at 0° C., the reaction was stirred at it overnight The reaction was treated with NaCl solution (10 mL, sat) and extracted with EtOAc (3×10 mL) The organic layers were washed with 10% HCl (10 mL), 5% NaHCO$_3$ (10 mL) and NaCl (10 mL, sat), dried (Na$_2$SO$_4$), filtered and concentrated. The crude oil (13 mg) was purified by HPLC.

Example 8

Synthesis of L-3-(2-naphthyl)alanine$^5$ Tamandarin B

A naphthylalanine analog of tamandarin (L-3-(2-naphthyl)alanine$^5$ Tamandarin B) was prepared as shown in Schemes 23-26 and described below.

Scheme 23

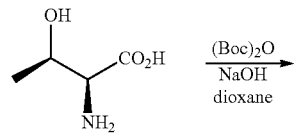

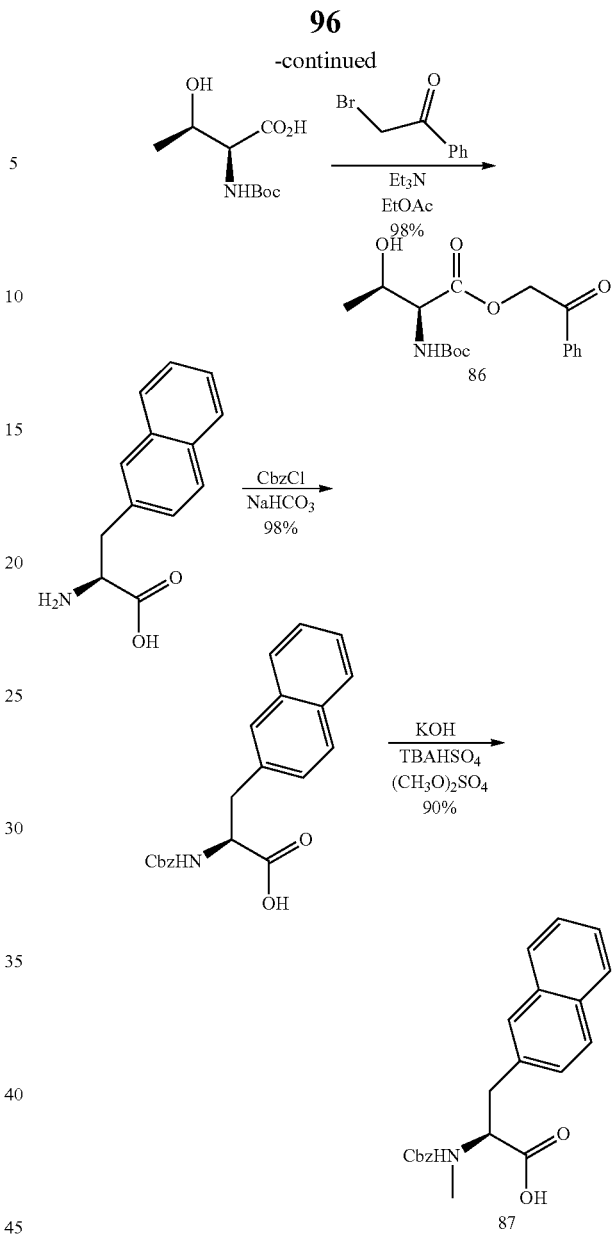

Scheme 24

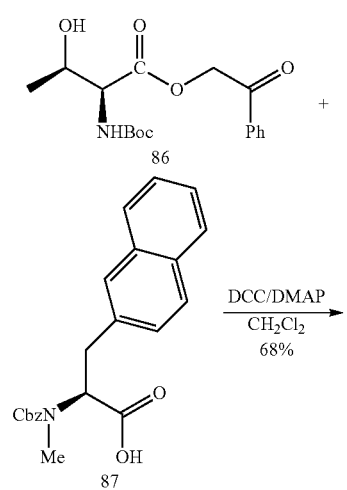

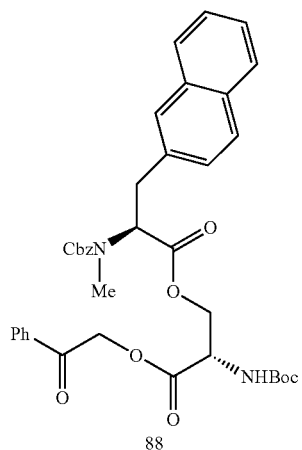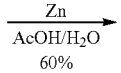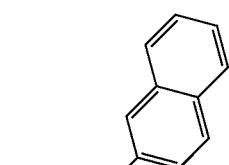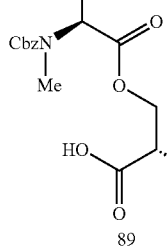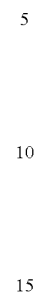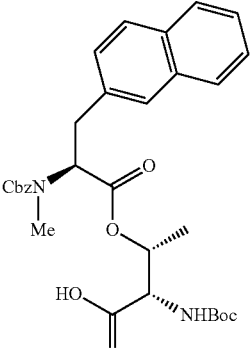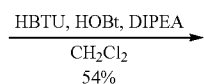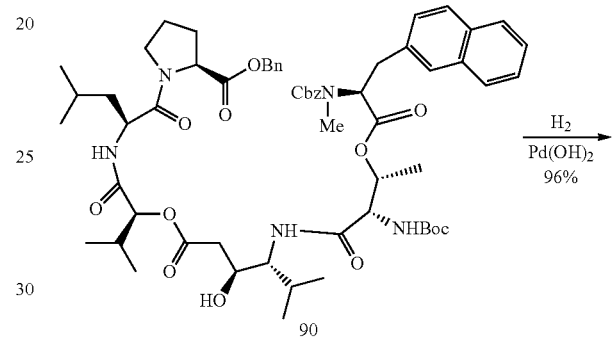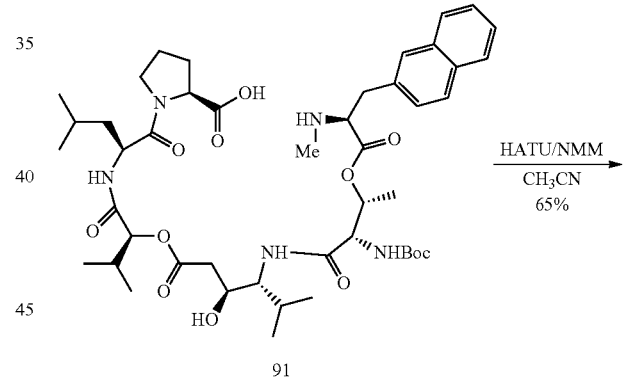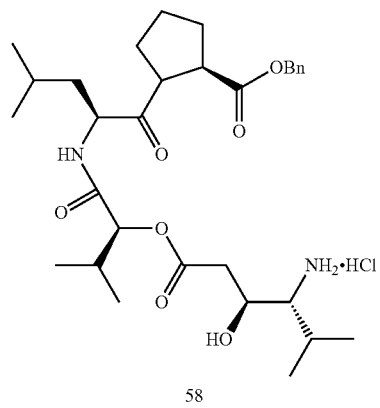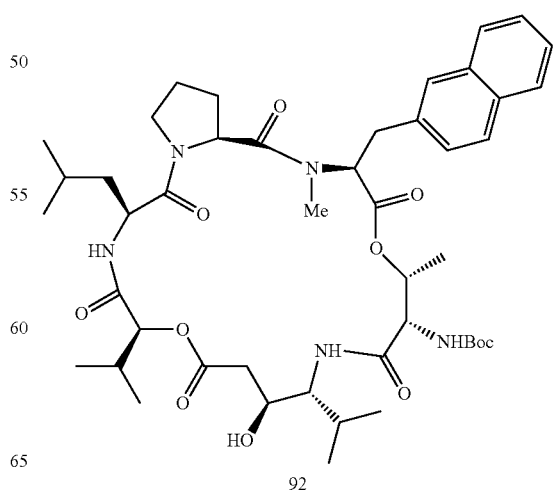

Scheme 26

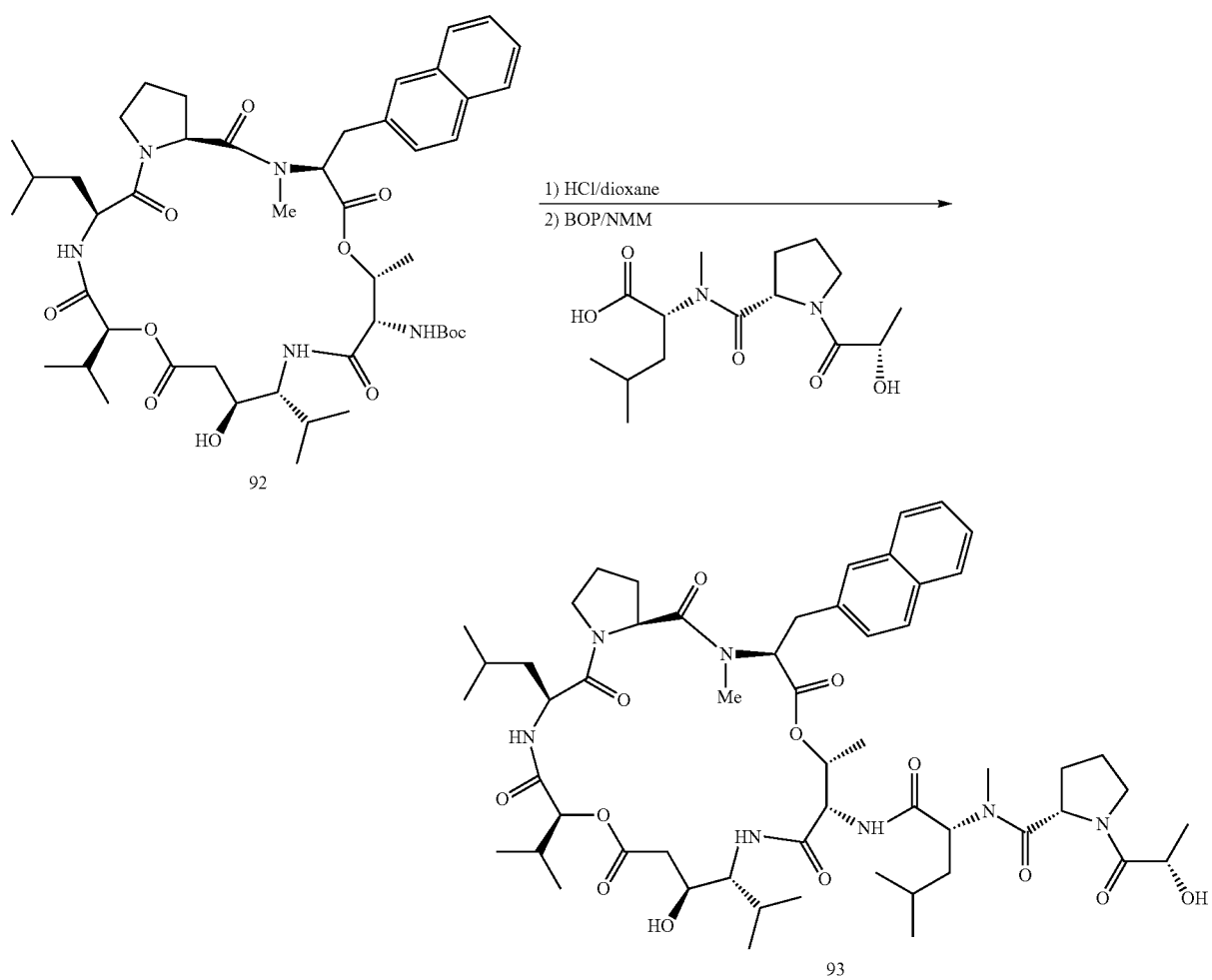

L-N-Boc-Threonine Phenacyl Ester (86): To a stirred suspension of L-N-Boc-threonine (2 g, 9.13 mmol) in EtOAc (20 mL), cooled to 0° C., Et₃N (1.31 mL, 9.13 mmol) and bromoacetophenone (1.82 g, 9.13 mmol) were added. The resulting mixture was stirred at room temperature for 2 days, diluted with EtOAc (50 mL) and washed with 10% HCl (20 mL), 5% NaHCO₃ (20 mL) and saturated NaCl (20 mL) solutions. The organic layer was dried (Na₂SO₄), and the solvent was evaporated. The residue was triturated with ether and filtered to afford 86 (2.8 g, 83%) as yellow foam. $R_f$=0.55 (AcOEt/Hexanes 1/1). $[\alpha]_D^{20}$=−29.4 (c=2, AcOEt). ¹H-NMR (300 MHz, CDCl₃): 1.31 (d, J=6.6 Hz, 3H), 1.46 (s, 9H), 3.77 (s, 1H), 4.44 (m, 1H), 4.60 (m, 1H), 5.34 (d, J=16.5 Hz, 1H), 5.37 (m, 1H), 5.68 (d, J=16.7 Hz, 1H), 7.51 (m, 2H), 7.65 (m, 1H), 7.92 (m, 1H).

L-N-Cbz-N-Methyl-2-naphthylalanine (87): To a stirred solution of L-N-Cbz-2-naphthylalanine (0.80 g, 2.29 mmol) in THF (40 mL), at 0° C., finely powered KOH (0.89 g, 16.0 mmol) was added in portions, followed by the addition of tetrabutylammonium hydrogen sulfate (80 mg, 10% by weight). Then, dimethyl sulfate (0.86 mL, 9.16 mmol) was added dropwise over 15 min. The reaction was stirred for an additional 30 min and H₂O (50 mL) was added. After stirring 5 h at room temperature, 20% aqueous ammonium hydroxide solution was added (10 mL). The reaction was diluted with ether (50 mL), the aqueous layer was separated and the organic layer was extracted with saturated aq NaHCO₃ (2×20 mL). The combined aqueous layers were acidified to pH 1 with 1M KHSO₄ and extracted with EtOAc (2×100 mL). The organic layers were combined, dried (Na₂SO₄), filtered and concentrated. The resulting acid 87 (832 mg, 90%) was obtained as a yellow oil and used in the next step without purification. ¹H-NMR (500 MHz, CDCl₃): 2.89 and 2.94 (s, 3H), 2.27-3.32 (m, 1H), 3.46-3.55 (m, 1H), 4.97-5.09 (m, 3H), 7.12-7.52 (m, 12H).

O-(L-N-Cbz-N-Methyl-2-naphthylalanine)-L-N-Boc-threonine Phenacyl Ester (88): To a solution of L-N-Boc-threonine phenacyl ester 86 (852 mg. 2.29 mmol) in CH₂Cl₂ (15 mL), cooled to 0° C., DMAP (84 mg, 0.68 mmol) and L-N-Cbz-N-methylnaphthylalanine 87 (832 mg, 2.29 mmol) were added. After stirring 10 min at 0° C., DCC (519 mg, 2.52 mmol) was added. The reaction mixture was stirred overnight at room temperature. The mixture was filtered, and the filtrate was concentrated to dryness. The residue was dissolved in CH₃CN (15 mL), filtered again, and evaporated. The crude oil was dissolved in EtOAc (50 mL) and washed with 10% KHSO₄ (50 mL), NaHCO₃ (50 mL, sat) and NaCl (50 mL, sat). The organic layer was dried (Na₂SO₄), and the solvent was evaporated. The crude oil was purified by column chromatography (silica gel, grad EtOAc/Hexanes 3/1) to yield the dipeptide 88 (1.02 g, 68%) as a pale yellow oil. $R_f$ 0.25 (AcOEt/Hexanes 1:3). $[\alpha]_D^{20}$=−27.6 (c=1, $CH_2Cl_2$). $^1$H-NMR (500 MHz, $CDCl_3$): 1.22 (d, J=6.9 Hz, 3H), 1.49 (s, 9H), 2.77 and 2.92 (m, 3H), 3.21-3.31 (m, 1H), 3.50-3.56 (m, 1H), 3.75 (m, 1H), 4.46-4.48 (m, 1H), 4.67-4.69 (m, 1H), 5.00-5.71 (m, 4H), 7.16-7.46 (m, 3H), 7.47-7.64 (m, 4H), 7.51-7.94 (m, 5H). $^{13}$C-NMR (125 MHz, $CDCl_3$): 17.0, 17.3, 28.7, 35.3, 31.7, 32.0, 35.38, 39.8, 50.1, 57.5, 59.8, 66.9, 67.3, 67.6, 68.7, 80.0, 125.9, 126.4, 127.5, 127.8, 127.9, 128.0, 128.2, 128.4, 128.8, 129.3, 129.5, 132.7, 133.8, 133.9, 134.4, 135.0, 169.3, 169.7, 171.5, 193.6. IR (neat) 3433.6, 2977.9, 1753.9, 1707.6, 1598.4, 1510.7, 1450.0, 1367.5, 1314.5, 1161.2.

O-(L-N-Cbz-N-Methylnaphthylalanine)-L-N-Boc-threonine (89): To a solution of serine phenacyl ester 88 (500 mg, 0.75 mmol) in aq. AcOH (7 mL, 90%), cooled to 0° C., powdered Zn (383 mg, 5.48 mmol) was added. The resulting mixture was stirred 3 h at 0° C., filtered over Celite®, and the Celite® washed with EtOAc (25 mL). The filtrate was washed with 10% $KHSO_4$ (20 mL), $NaHCO_3$ (20 mL, sat), and NaCl (20 mL, sat). The organic layer was dried ($Na_2SO_4$), and the solvent was evaporated. The crude oil was purified by column chromatography (silica gel, MeOH/$CH_2Cl_2$ 1/9) to yield the acid 89 (248 mg, 60%) as white foam. $R_f$ 0.35 (MeOH/$CH_2Cl_2$ 1/9). $[\alpha]_D^{20}$=+7.10 (c=0.7, $CH_2Cl_2$). $^1$H-NMR (500 MHz, $CDCl_3$): 1.29-1.32 (m, 3H), 1.48 (s, 9H), 2.78-2.80 (m, 3H), 3.17-3.22 (m, 1H), 3.25-3.54 (m, 1H), 4.52-4.53 (m, 1H), 5.03-5.15 (m, 2H), 5.44-5.64 (m, 2H), 7.19-7.36 (m, 5H), 7.50-7.54 (m, 3H), 7.71-7.89 (m, 4H). $^{13}$C-NMR (125 MHz, $CDCl_3$): 16.4, 16.7, 20.7, 28.1, 31.7, 32.0, 34.6, 34.9, 39.8, 50.1, 57.3, 60.6, 66.4, 72.2, 80.0, 125.4, 125.9, 126.7, 127.5, 127.9, 128.2, 128.8, 132.2, 133.4, 134.2, 136.1, 156.1, 156.9, 169.3, 169.7, 169.8. IR (neat) 3435.1, 2978.4, 1743.4, 1709.6, 1499.9, 1402.2, 1315.6, 1217.1, 1162.0, 1060.6, 752.2.

[2-Naphthylala$^5$]-Tamandarin B Protected Linear Precursor (90): To a solution of 56 (110 mg, 0.14 mmol) in dioxane (5 mL), cooled to 0° C., was added a solution of HCl in dioxane (5 mL). The resulting solution was stirred at room temperature for 2 h. The solution was concentrated, and the residue was diluted with $CH_2Cl_2$ and concentrated again to yield the hydrochloride salt (85 mg, quantitative yield) as a white solid, which was used directly in the next step. To a mixture of hydrochloride salt (85 mg, 0.14 mmol) HBTU (53 mg, 0.14 mmol), HOBt (19 mg, 0.14 mmol) and acid 89 (79 mg, 0.14 mmol), cooled to −5° C., a solution of $CH_2Cl_2$/DMF 2/1 (4 mL) was added. The reaction was stirred 5 min, and DIPEA (72 µL, 0.56 mmol) was added. The resulting solution was stirred at −5° C. overnight, diluted with t-BuOMe (10 mL), washed with 10% $KHSO_4$ (10 mL), $NaHCO_3$ (10 mL, sat) and NaCl (10 mL, sat), dried ($Na_2SO_4$), filtered, and concentrated. The crude oil was purified by column chromatography (silica gel, grad EtOAc/Hex 1/1) to yield 90 (60 mg, 54%). $R_f$ 0.23 (AcOEt/Hexanes 1:1). $[\alpha]_D^{20}$=−34.6 (c=1, $CH_2Cl_2$). $^1$H-NMR (500 MHz, $CDCl_3$): 0.89-1.01 (m, 18H), 1.26-1.29 (m, 5H), 1.48 (s, 9H), 1.70-1.62 (m, 2H), 2.03-2.22 (m, 5H), 2.21-2.25 (m, 3H), 2.55-2.60 (m, 1H), 2.82-2.93 (m, 3H), 3.03-3.18 (m, 1H), 3.45-3.49 (m, 1H), 3.60-3.79 (m, 2H), 4.12-4.15 (m, 1H), 4.50-4.51 (m, 1H), 4.92-5.34 (m, 6H), 5.34-5.47 (m, 1H), 7.16-7.35 (m, 9H), 7.44-7.85 (m, 8H). $^{13}$C-NMR (125 MHz, $CDCl_3$): 14.1, 16.9, 17.9, 18.4, 19.0, 18.7, 20.2, 20.9, 21.6, 23.7, 24.5, 24.7, 25.5, 28.1, 28.2, 28.9, 29.6, 30.4, 30.6, 33.9, 38.7, 41.0, 43.0, 44.1, 46.8, 48.4, 57.9, 60.3, 60.5, 66.9, 67.0, 67.3, 68.6, 70.3, 77.9, 78.2, 79.1, 125.5, 125.9, 127.0, 127.2, 127.5, 127.7, 127.8, 128.0, 128.3, 128.5, 130.1, 132.2, 133.4, 135.1, 135.2, 136.9, 142.0, 157.0, 157.2, 157.3, 169.9, 171.3, 171.9, 180.8. IR (neat) 3326.4, 3062.0, 2961.1, 2873.6, 2248.6, 1743.7, 1681.9, 1635.0, 1537.2, 1453.5, 1367.4, 1170.2. HRMS m/z cald for $C_{61}H_{81}N_5O_{14}Na$ (M+Na): 130.5677 found 130.5634.

[2-Naphthylala$^5$]-Tamandarin B macrocycle (92): To a solution of protected linear precursor 90 (60 mg, 0.054 mmol) in MeOH under argon, Pd(OH)$_2$ (21 mg) was added. The reaction was purged with H$_2$ and stirred overnight under H$_2$ atmosphere (1 atm). The mixture was filtered through Celite®. The filtrate was concentrated to yield the free linear precursor 91 (45 mg, 96%) as a yellow oil, which was used in the next step without purification.

The crude amino acid linear precursor (45 mg, 0.050 mmol) was dissolved in $CH_3CN$ (10 mL) and cooled to 0° C. HATU (46 mg, 0.12 mmol) was added followed by the dropwise addition of NNM 0.10 mmol). The reaction mixture was stirred at 0° C. for 1 h and then overnight. The reaction mixture was concentrated in vacuo, diluted with EtOAc (10 mL), washed with 10% $KHSO_4$ (10 mL), 5% $NaHCO_3$ (10 mL) and NaCl (10 mL, sat), dried ($Na_2SO_4$), filtered, and concentrated. The crude oil was purified by column chromatography (silica gel, EtOAc/Hexanes 2/1) to yield protected macrocycle 92 (28 mg, 65%) as white foam. $R_f$ 0.26 (AcOEt/Hexanes 1/2). $[\alpha]_D^{20}$=−55.2 (c=1, $CHCl_3$). $^1$H-NMR (500 MHz, $CDCl_3$): 0.90-1.02 (m, 24H), 1.29 (d, 6.6 Hz, 3H), 1.48 (s, 9H), 1.71-1.85 (m, 2H), 2.05-2.09 (m, 2H), 2.19-2.23 (m 0.2H), 2.52 (s, 3H), 2.96 (dd, J=4.7 and 16.9 Hz, 1H), 3.46 (dd, J=10.7 and 14.0 Hz, 1H), 3.67 (dd, J=4.3 and 13.9 Hz, 1H), 3.73-3.77 (m, 2H), 3.78-3.83 (m, 1H), 3.99-4.05 (m, 1H), 4.39 (dd, J=3.1 and 10.3 Hz, 1H), 4.56-4.59 (m, 1H), 4.92 (t, J=12.0 Hz, 1H), 4.97-5.00 (m, 2H), 5.00-5.02 (m, 1H), 7.36-7.37 (m, 1H), 7.49-7.52 (m, 2H), 7.56-7.58 (m, 2H), 7.72-7.74 (m, 1H), 7.76-7.79 (m, 2H), 7.98-8.00 (m, 1H). $^{13}$C-NMR (125 MHz, $CDCl_3$): 15.6, 18.4, 189, 18.9, 20.6, 21.2, 23.9, 25.3, 25.4, 28.0, 28.4, 28.5, 30.8, 35.6, 39.0, 39.3, 39.5, 47.2, 48.8, 56.3, 57.5, 60.7, 66.0, 69.3, 71.9, 79.6, 80.7, 126.3, 126.9 127.5, 127.8, 128.2, 128.5, 128.9, 132.8, 133.9, 135.9, 156.2, 169.0, 170.1, 170.9, 171.7, 172.0 173.2. IR (neat) 3339.5, 2962.0, 2872.0, 2248.4, 1742.0, 1665.7, 1635.5, 1529.6, 1451.1, 1167.4, 851.3.

[2-Naphthylala$^5$]-Tamandarin B (93): To a solution of Boc protected macrocycle 92 (28 mg, 0.032 mmol) in HPLC dioxane (3 mL) was added a solution of HCl in dioxane (3 mL). The resulting solution was stirred at room temperature for 2 h. The solution was concentrated and the residue diluted with $CH_2Cl_2$ and concentrated again to yield the hydrochloride salt (quantitative yield) as a white solid, which was used directly in the next step. To a mixture of the macrocycle amine salt (25 mg, 0.031 mmol) and side chain (14.6 mg, 0.046 mmol) in $CH_2Cl_2$ (4 mL) at 0° C. was added BOP (20.3 mg, 0.046 mmol) and NMM (14 µL, 0.12 mmol). After 30 min at 0° C., the reaction was stirred at rt overnight. The reaction was treated with NaCl solution (2 mL, sat) and extracted with EtOAc (2×10 mL) The organic layers were washed with 10% HCl (5 mL), 5% $NaHCO_3$ (5 mL), and NaCl (5 mL, sat), dried ($Na_2SO_4$), filtered, and concentrated. The crude oil (8 mg, 61%) was purified by HPLC. $^1$H-NMR (300 MHz, $CDCl_3$): δ 0.82-0.96 (m, 24H), 1.09-1.28 (m, 14H), 1.31 (d, J=6.8, 3H), 1.39 (d, J=6.8, 3H), 1.64 (m, 3H), 2.10 (m, 4H), 2.48 (s, 3H), 3.10 (s, 3H), 3.09-3.15 (m, 2H), 3.35-3.41 (m, 2H), 3.43-3.82 (m, 5H), 4.29-4.33 (m, 1H), 4.42-4.47 (m, 1H), 4.65-4.70 (m, 1H), 4.72 (t, J=6.8, 1H), 4.87 (t, J=8.3, 1H), 5.02 (d, J=5.3, 1H), 5.29-5.32 (m, 2H), 7.24-7.27 (m, 1H), 7.45-7.63 (m, 4H), 7.67-7.83 (m, 4H). HRMS m/z/z calcd for $C_{56}H_{83}N_7O_{13}Na$ (M+Na): 1084.5946 found 1084.5987.

Example 9

Replacement of an Ester Bond by an Amide Bond in the Tamandarin Macrocycle

The preparation of a compound according to Formula XXX was accomplished as shown in Schemes 27 and 28.

Scheme 27

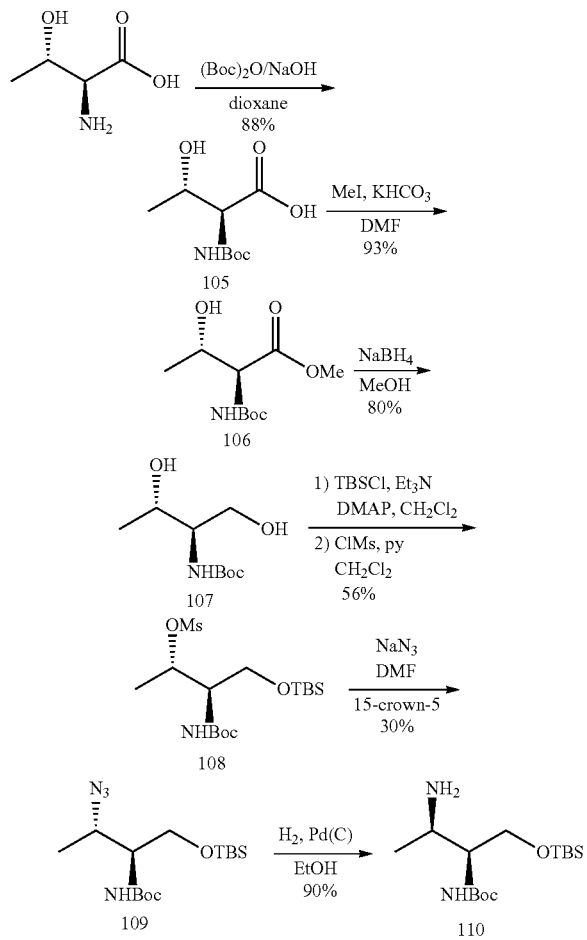

Scheme 28

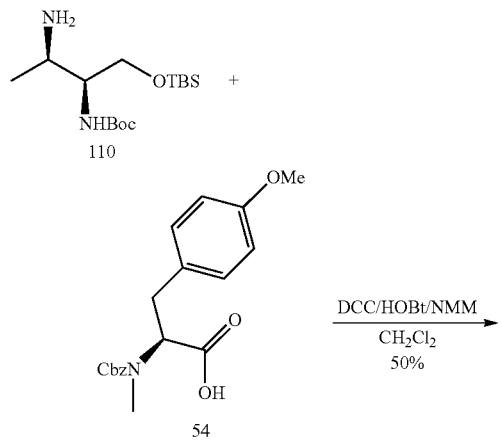

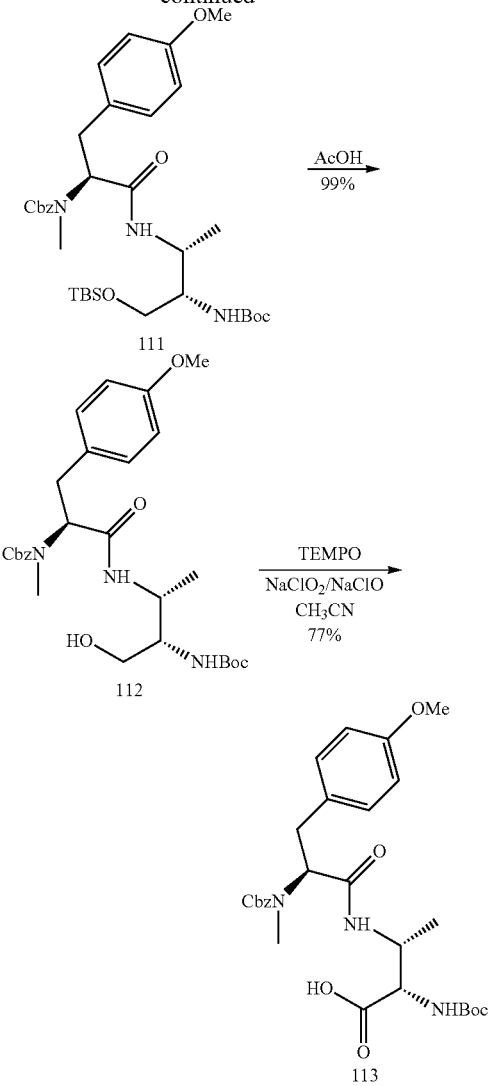

N-Boc-L-allo-Threonine Methyl Ester (106): To a solution of N-Boc-L-allo-threonine (500 mg, 2.28 mmol) in DMF (5 mL), KHCO$_3$ (637 mg, 4.56 mmol) and MeI (227 µl, 3.65 mmol) were added and the reaction was stirred 5 h at rt. Water (20 mL) was added and the mixture was extracted with ether (3×20 mL), dried (Na$_2$SO$_4$) and evaporated to afford the methyl ester 106 (494 mg, 93%) that was used without purification in the next step. $^1$H-NMR (500 MHz, CDCl$_3$): 1.19-1.25 (m, 3H), 1.48 (s, 9H), 3.78 (s, 3H), 4.05-4.10 (m, 1H), 4.32-4.40 (m, 1H), 4.45-4.54 (m, 1H).

2-tert-Butoxycarbonylamino-1,3-butanodiol (107): To a solution of methyl ester 106 (450 mg, 1.93 mmol) in HPLC EtOH (7 mL), cooled to 0° C., sodium borohydride (146 mg, 3.86 mmol) was added in portions. The reaction mixture was stirred at 0° C. for 2 h and at room temperature for 2 h. The reaction was quenched with NH$_4$Cl (sat, 15 mL), extracted with AcOEt (3×10 mL), dried (Na$_2$SO$_4$) and evaporated. The crude oil was purified by column chromatography (silica gel, EtOAc/Hexanes 2/1) to yield the diol 107 (347 mg, 87%) as colorless oil. R$_f$ 0.21 (AcOEt/Hexanes 2/1). [α]$_D^{20}$=−10.7 (c=1, CHCl$_3$). $^1$H-NMR (500 MHz, CDCl$_3$): 1.28 (d, J=6.9 Hz, 3H), 1.48 (s, 9H), 3.43-3.54 (m, 1H), 3.73 (dd, J=4.0 and 14.1 Hz, 1H), 3.98 (dd, J=5.9 and 13.1 Hz, 1H), 4.00-4.05 (m, 1H), 5.33-5.40 (m, 1H). $^{13}$C-NMR (125 MHz, CDCl$_3$): 20.3, 28.2, 28.3, 56.1, 62.4, 69.9, 79.8, 153.3. IR (neat) 3343.8, 2975.1, 2931.7, 1686.4, 1520.0, 1366.6, 1248.9, 1171.1, 1046.3.

2-tert-Butoxycarbonylamino-1-(tert-butyldimethylsilanyloxy)-3-butanol: To a solution of diol 107 (340 mg, 1.65 mmol) in $CH_2Cl_2$ (4 mL), cooled to 0° C., $Et_3N$ (274 µL, 1.98 mmol) and DMAP (8 mg, 0.04 mmol) were added. The solution was stirred 5 min, and TBSCl (248 mg, 1.65 mmol) was added. The reaction was stirred 18 h at room temperature quenched with $NH_4Cl$ (sat, 15 mL) and extracted with $CH_2Cl_2$ (3×10 mL), dried ($Na_2SO_4$) and evaporated. The crude oil was purified by column chromatography (silica gel, EtOAc/Hexanes 1/9) to yield the TBS alcohol (300 mg, 56%) as colorless oil. $R_f$ 0.37 (AcOEt/Hexanes 1/9). $[α]_D^{20}=-24.7$ (c=1, $CHCl_3$). $^1$H-NMR (500 MHz, $CDCl_3$): 0.05 (s, 6H), 0.86 (s, 9H), 1.30 (d, J=6.8 Hz, 3H), 1.47 (s, 9H), 3.46-3.51 (m, 1H), 4.75-4.80 (m, 1H), 4.89-4.92 (m, 1H), 3.98 (dd, J=1.9 and 11.5 Hz, 1H), 5.22-5.30 (m, 1H). IR (neat) 3447.8, 2954.8, 2857.1, 2362.1, 1699.0, 1498.3, 1254.3, 1173.8, 1108.1, 836.9, 777.5.

2-tert-Butoxycarbonylamino-1-(tert-butyldimethylsilanyloxy)-3-methylsulphonyloxybutane (108): To a solution of alcohol (100 mg, 0.31 mmol) in $CH_2Cl_2$ (10 mL), cooled to 0° C., $Et_3N$ (64 µL, 0.46 mmol) and MsCl (31 µL, 0.40 mmol) were added. The solution was stirred 1 h at room temperature quenched with $NH_4Cl$ (sat, 15 mL) and extracted with AcOEt (3×10 mL), dried ($Na_2SO_4$) and evaporated to afford 108 (113 mg, 91%). The crude residue was used with further purification in the next step. $^1$H-NMR (500 MHz, $CDCl_3$): 0.04 (s, 6H), 0.88 (s, 9H), 1.45-1.50 (m, 12H), 2.99 (s, 3H), 3.66-3.71 (m, 1H), 4.85-4.90 (m, 1H), 4.80-4.92 (m, 1H).

3-Azido-2-tert-butoxycarbonylamino-1-(tert-butyldimethyl-silanyloxy)butane (109): To a solution of mesylate 108 (500 mg, 1.26 mmol) in HMPA (2 mL), $NaN_3$ (409 mg, 6.29 mmol) and 15-crown-5 ether (252 mg, 1.26 mmol) were added. The solution was stirred at 55° C. for 3 h. The reaction mixture was added to EtOAc (30 mL), washed with brine (10 mL), dried ($Na_2SO_4$) and evaporated. The crude oil was purified by column chromatography (silica gel, EtOAc/Hexanes 1/15) to afford azide 109 (160 mg, 34%) as a colorless oil. $R_f$ 0.33 (AcOEt/Hexanes 1/15). $[α]_D^{20}=-46.6$ (c=0.4, $CHCl_3$). $^1$H-NMR (500 MHz, $CDCl_3$): 0.04 (s, 6H), 0.88 (s, 9H), 1.32 (d, J=6.7 Hz, 3H), 1.48 (s, 9H), 3.51-3.61 (m, 1H), 4.75-4.90 (m, 2H), 4.50-4.62 (m, 1H). $^{13}$C-NMR (125 MHz, $CDCl_3$): −5.5, 14.1, 16.5, 25.8, 28.3, 31.6, 55.2, 57.2, 62.4, 174.3. IR (neat) 3326.1, 2954.0, 2931.1, 2857.9, 2359.9, 2107.2, 1718.2, 1005.7, 1471.2, 1366.0, 1254.5, 1167.7, 1098.0, 838.1.

3-Amino-2-tert-Butoxycarbonylamino-1-(tert-butyldimethyl-silanyloxy)butane (110): To a solution of azide 109 (35 mg, 0.10 mmol) in EtOH (1 mL), under argon, 10% Pd/c (7 mg) was added. The reaction was purged with $H_2$ and stirred overnight under $H_2$ atmosphere (1 atm). The mixture was filtered through Celite®. The filtrate was concentrated to yield the amine 110 (29 mg, 90%). The crude residue was used without further purification in the next step. $^1$H-NMR (500 MHz, $CDCl_3$): 0.05 (s, 6H), 0.90 (s, 9H), 1.12 (d, J=6.7 Hz, 3H), 1.47 (s, 9H), 3.21-3.31 (m, 1H), 3.42-3.48 (m, 1H), 3.63-3.82 (m, 2H), 5.01-5.10 (m, 1H). $^{13}$C-NMR (125 MHz, $CDCl_3$): −5.1, 19.1, 21.3, 26.2, 28.8, 47.1, 56.9, 64.5, 176.5.

3-(N-Cbz-N,O-Dimethyltyrosyl)amino-2-tert-butoxycarbonylamino-1-(tert-butyl-dimethylsilanyloxy)butane (111): To a solution of amine 110 (20 mg, 0.062 mmol) in $CH_2Cl_2$ (1 mL), cooled to 0° C., NMM (7 µL, 0.069 mmol) and HOBt (25 mg, 0.18 mmol) were added. The solution was stirred at 0° C. for 15 minutes, and a solution of N-Cbz-N,O-dimethyltyrosine (21) (21 mg, 0.062 mmol) in $CH_2Cl_2$ (1 mL) was added. Finally a solution of DCC (14.2 mg, 0.069 mmol) in $CH_2Cl_2$ (1 mL) was added. The mixture was stirred 16 h at room temperature and filtered to remove the precipitate. The filtrate was diluted with $CH_2Cl_2$ (10 mL) and washed with 10% $KHSO_4$ (10 mL), 5% $NaHCO_3$ (10 mL) and NaCl (10 mL, sat), dried ($Na_2SO_4$), filtered, and concentrated. The crude oil was purified by column chromatography (silica gel, EtOAc/Hexanes 1/3) to yield 111 (26 mg, 70%) as a white foam. $R_f$ 0.36 (AcOEt/Hexanes 1/3). $[α]_D^{20}=-40.1$ (c=0.5, $CHCl_3$). $^1$H-NMR (500 MHz, $CDCl_3$): 0.09 (s, 6H), 0.95 (s, 9H), 1.14-1.17 (m, 3H), 1.43 (s, 9H), 2.86 (s, 3H), 3.29-3.32 (m, 1H), 3.42-3.48 (m, 1H), 3.60-3.68 (m, 2H), 3.82 (s, 3H), 4.17-4.18 (m, 1H), 4.87-4.89 (m, 1H), 4.95-4.96 (m, 1H), 5.02-5.14 (m, 2H), 5.21-5.22 (m, 2H), 6.34-6.37 (m, 1H), 6.79-6.83 (m, 2H), 6.98-7.00 (m, 1H), 7.01-7.17 (m, 2H), 7.20-7.36 (m, 5H). $^{13}$C-NMR (125 MHz, $CDCl_3$): −5.5, 17.9, 18.2, 25.8, 28.3, 33.2, 44.5, 55.12, 62.6, 67.3, 57.1, 66.1, 113.8, 127.5, 127.9, 128.4, 129.8, 158.2, 171.5. IR (neat) 3328.5, 2930.3, 2856.3, 2361.0, 2346.6, 2249.0, 1708.8, 1513.7, 1452.5, 1449.5. HRMS m/z cald for $C_{34}H_{53}N_5O_7Na$ (M+Na): 666.3550 found 666.3571.

3-(N-Cbz-N,O-Dimethyltyrosyl)amino-2-tert-butoxycarbonylamino-1-butanol (112): A solution of 111 (15 mg, 0.086 mmol) in AcOH (1 mL) was stirred 15 h. at room temperature. The reaction was concentrated to yield 112 (11 mg, 90%) as a colorless oil. The crude residue was used with further purification in the next step. $^1$H-NMR (500 MHz, $CDCl_3$): 1.04 (d, J=6.9 Hz, 3H), 1.45 (s, 9H), 2.81 (s, 3H), 2.88-2.92 (m, 1H), 3.02-3.09 (m, 1H), 3.29-3.33 (m, 1H), 3.51-3.62 (m, 1H), 3.70-3.79 (m, 1H), 3.78 (s, 3H), 4.02-4.08 (m, 1H), 4.43-4.47 (m, 1H), 4.51-4.55 (m, 1H), 5.05-5.18 (m, 2H), 5.22 (s, 2H), 5.98-5.99 (m, 1H), 6.72 ((d, J=7.9 Hz, 2H), 6.90-7.01 (m, 2H), 7.22-7.38 (m, 5H).

Example 10

Modification to the $Lac^9$ Unit

A compound according to Formula I, wherein $R^5$ contains a modified lactate unit is prepared as described here.

(R)-glycidic acid (117) was prepared from (S)-serine following the procedure described by Petit and Larcheveque, *Org. Synth.* 75:37-44 (1998).

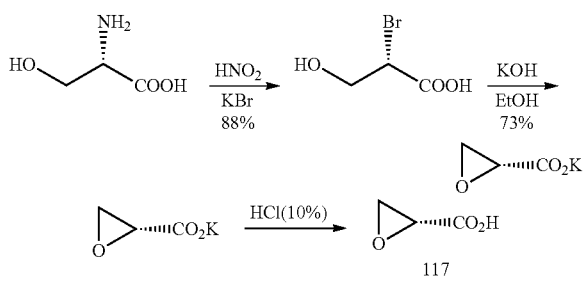

The trifluoroacetate salt of L-proline benzyl ester (118) was prepared by reaction of N-Boc-proline with benzyl bromide in the presence of $Et_3N$. The Boc group was removed using trifluoroacetic acid. Subsequently, the reaction of (R)-glycidic acid (117) with 119 afforded the proline derivative 120.

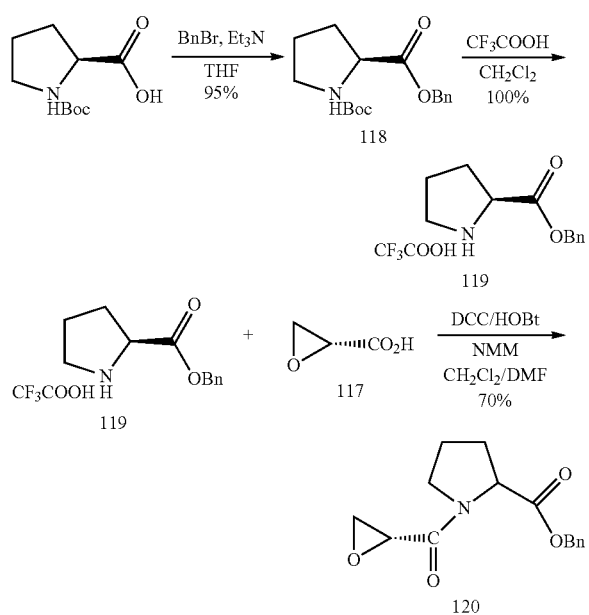

The benzyl ester is removed without opening of the epoxide moiety using LiOH in MeOH. N-Glycidyl-L-proline is then used to prepare suitable $R^5$ moieties to prepare a compound according to Formula I, IA, or II, or alternatively, N-Glycidyl-L-proline is coupled directly with the free amine of the macrocycle, e.g., compound 35, deprotected 61.

N-Glycidyl-L-Proline Benzyl Ester (120): To a solution of L-proline benzyl ester (156 mg, 0.49 mmol) in DMF (2 mL), cooled to 0° C., NMM (56 µL, 0.53 mmol) and HOBt (198 mg, 1.47 mmol) were added. The solution was stirred at 0° C. for 15 minutes and a solution of glycidic acid[21] (100 mg, 1.13 mmol) in $CH_2Cl_2$ (2 mL) was added. Finally a solution of DCC (253 mg, 1.23 mmol) in $CH_2Cl_2$ (2 mL) was added. The mixture was stirred 16 h at room temperature and filtered to remove the precipitate. The residue was diluted with $CH_2Cl_2$ (10 mL) and washed with 10% $KHSO_4$ (10 mL), 5% $NaHCO_3$ (10 mL) and NaCl (10 mL, sat), dried ($Na_2SO_4$), filtered and concentrated. The crude oil was purified by column chromatography (silica gel, EtOAc/Hexanes 1/1) to yield 120 (95 mg, 70%) as white foam. $R_f$ 0.26 (AcOEt/Hexanes 1/1). $^1$H-NMR (500 MHz, $CDCl_3$): mixture of rotamers 1.87-1.92 (m, 2H), 1.91-1.98 (m, 2H), 1.99-2.03 (m, 1H), 2.19-2.20 (m, 2H), 2.20-2.22 (m, 1H), 2.66-2.68 (m, 1H), 2.80-2.82 (m, 1H), 2.94-2.95 (m, 2H), 3.30-3.31 (m, 1H), 3.56-3.57 (m, 2H), 357-370 (m, 2H), 3.72-3.85 (m, 1H), 4.57-4.59 (m, 1H), 4.70-4.72 (m, 1H), 5.16 (s, 2H), 5.22-5.29 (m, 2H), 7.25-7.38 (m, 10H). $^{13}$C-NMR (125 MHz, $CDCl_3$): 22.2, 24.9, 28.7, 30.9, 31.5, 45.9, 46.3, 46.4, 47.2, 48.0, 48.5, 58.7, 59.3, 66.9, 67.4, 128.1, 128.2, 128.4, 128.5, 128.7, 170.0, 182.3. HRMS m/z cald for $C_{15}H_{17}NO_4a$ (M+Na): 298.1055 found 298.1047.

N-Glycidyl-L-proline is prepared from compound 120 by hydrolyzing the benzyl ester with $LiOH/H_2O$ in methanol.

Example 11

Biological Activity of Tamandarin Analogs

The experiments described in this example demonstrate that the tamandarin analogs have the desired bioactivity.

As used herein, "$GI_{50}$" refers to the dose of a compound which is capable of producing 50% inhibition of cell growth. $GI_{50}$ is assessed by comparing growth of cells to which a compound has been administered with growth of the same cells to which the compound has not been administered.

As used herein, "$LC_{50}$" refers to the dose of a compound which is capable of producing 50% lethality in cells. $LC_{50}$ is assessed by comparing death of cells in a population of cells to which a compound has been administered with the death of cells in a population of the same cells to which the compound has not been administered.

"NCI-60" refers to a 60 tumor cell line panel which from the National Cancer Institute (NCI, Frederick, Md.). "NCI-60 Mean" is the average $GI_{50}$ or $LC_{50}$ for the panel treated with the selected compound.

The data for the compounds are disclosed in the following tables.

TABLE 1

In vitro results of tamandarin B (units: Molar)

| | DU145 | LN-caP | IGROV | IGROV-ET | SK-BR3 | SK-MEl28 | A549 |
|---|---|---|---|---|---|---|---|
| GI50 | 7.08E−09 | 5.84E−09 | 7.31E−09 | 1.73E−07 | 5.44E−09 | 3.03E−09 | 7.62E−09 |
| TGI | 2.41E−08 | 2.13E−08 | 2.91E−08 | 2.04E−06 | 2.49E−08 | 1.19E−08 | 4.01E−08 |
| LC50 | 7.97E−08 | 1.42E−07 | 1.33E−07 | 9.59E−06 | 2.36E−07 | 1.19E−07 | 7.66E−07 |

| | K562 | PANC1 | HT29 | LOVO | LOVO-DOX | HFLA | HELA APL |
|---|---|---|---|---|---|---|---|
| GI50 | 8.47E−09 | 1.40E−08 | 6.32E−09 | 3.05E−08 | 1.25E−06 | 3.90E−09 | 5.97E−08 |
| TGI | 2.63E−08 | 5.69E−08 | 4.32E−08 | 1.61E−07 | 9.59E−06 | 1.76E−08 | 1.16E−06 |
| LC50 | 7.82E−08 | 4.13E−07 | 9.59E−06 | 9.59E−06 | 9.59E−06 | 1.20E−07 | 9.59E−06 |

TABLE 2

In vitro results of Phe5 tamandarin B (units: Molar)

| | DU145 | LN-caP | IGROV | IGROV-ET | SK-BR3 | SK-MEl28 | A549 |
|---|---|---|---|---|---|---|---|
| GI50 | 2.37E−09 | 1.52E−09 | 2.49E−09 | 2.15E−07 | 6.58E−10 | 2.74E−09 | 4.56E−09 |
| TGI | 1.02E−08 | 8.32E−09 | 1.28E−08 | 7.88E−07 | 4.49E−09 | 1.88E−08 | 3.90E−08 |
| LC50 | 2.68E−07 | 1.01E−07 | 1.24E−07 | 6.35E−06 | 3.12E−07 | 2.05E−07 | 9.35E−07 |

TABLE 2-continued

In vitro results of Phe5 tamandarin B (units: Molar)

| | K562 | PANC1 | HT29 | LOVO | LOVO-DOX | HELA | HELA APL |
|---|---|---|---|---|---|---|---|
| GI50 | 2.32E−08 | 3.81E−09 | 4.77E−09 | 2.61E−08 | 3.58E−07 | 1.17E−09 | 4.45E−08 |
| TGI | 9.88E−07 | 3.28E−08 | 7.89E−08 | 8.81E−08 | 1.97E−06 | 4.61E−09 | 4.23E−07 |
| LC50 | 9.88E−06 | 9.88E−06 | 9.88E−06 | 5.22E−06 | 9.88E−06 | 5.55E−08 | 9.88E−06 |

Cell Lines

| Name | N° ATCC | Species | Tissue | Characteristics |
|---|---|---|---|---|
| A549 | CCL-185 | human | lung | lung carcinoma "NSCL" |
| SK-MEL-28 | HTB-72 | human | melanoma | malignant melanoma |
| HT29 | HTB-38 | human | colon | colon adenocarcinoma |
| LoVo | CCL-229 | human | colon | colon adenocarcinoma |
| LoVo-Dox | | human | colon | colon adenocarcinoma (MDR) |
| DU-145 | HTB-81 | human | prostate | prostate carcinoma, not androgen receptors |
| LN-caP | CRL-1740 | human | prostate | prostate adenocarcinoma, with androgen receptors |
| SK-BR3 | HTB-30 | human | breast | breast adenocarcinoma, Her2/neu+, (pleural effusion) |
| IGROV | | human | ovary | ovary adenocarcinoma |
| IGROV-ET | | human | ovary | ovary adenocarcinoma, characterized as ET-743 resistant cells |
| HeLa | CCL-2 | human | cervix | cervix epitheloid carcinoma |
| HeLa-APL | CCL-3 | human | cervix | cervix epitheloid carcinoma, characterized as aplidine resistant cells |
| PANC1 | CRL-1469 | human | pancreas | pancreatic epitheloid carcinoma |

Inhibition of Cells Growth by Colorimetric Assay.

A colorimetric type of assay, using sulforhodamine B (SRB) reaction has been adapted for a quantitative measurement of cell growth and viability [following the technique described by Philip Skehan, et al. (1990), New colorimetric cytotoxicity assay for anticancer drug screening, *J. Natl. Cancer Inst.* 82:1107-1112].

This form of assay employs 96 well cell culture microplates of 9 mm diameter (Faircloth, 1988; Mosmann, 1983). Most of the cell lines are obtained from American Type Culture Collection (ATCC) derived from different human cancer types.

Cells are maintained in RPMI 1640 10% FBS, supplemented with 0.1 g/l penicillin and 0.1 g/l streptomycin sulfate and then incubated at 37° C., 5% CO2 and 98% humidity. For the experiments, cells were harvested from subconfluent cultures using trypsin and resuspended in fresh medium before plating.

Cells are seeded in 96 well microtiter plates, at 5×103 cells per well in aliquots of 195 μl medium, and they are allowed to attach to the plate surface by growing in drug free medium for 18 hours. Afterward, samples are added in aliquots of 5 μl in a ranging from 10 to 10-8 μg/ml, dissolved in DMSO/EtOH/ PBS (0.5:0.5:99). After 48 hours exposure, the antitumor effect are measured by the SRB methodology: cells are fixed by adding 50 μl of cold 50% (wt/vol) trichloroacetic acid (TCA) and incubated for 60 minutes at 4° C. Plates are washed with deionised water and dried. One hundred μl of SRB solution (0.4% wt/vol in 1% acetic acid) is added to each microtiter well and incubated for 10 minutes at room temperature. Unbound SRB is removed by washing with 1% acetic acid. Plates are air dried and bound stain is solubilized with Tris buffer. Optical densities are read on a automated spectrophotometric plate reader at a single wavelength of 490 nm.

The values for mean+/−SD of data from triplicate wells are calculated. Some parameters for cellular responses can be calculated: GI=growth inhibition, TGI=total growth inhibition (cytostatic effect) and LC=cell killing (cytotoxic effect).

Table 1 illustrates data on the biological activity of the compounds (in Molar units) of the present invention.

| | | Compound 62 | Compound 75 | Compound 93 |
|---|---|---|---|---|
| DU-145 | GI50 | 6.79E−09 | 1.81E−06 | 2.17E−09 |
| | TGI | 2.49E−08 | 4.95E−06 | 4.39E−09 |
| | LC50 | 8.26E−08 | 9.84E−06 | 8.83E−09 |
| LN-caP | GI50 | 2.71E−09 | 5.48E−07 | 1.98E−09 |
| | TGI | 7.24E−09 | 2.97E−06 | 4.33E−09 |
| | LC50 | 5.84E−08 | 9.84E−06 | 9.70E−09 |
| IGROV | GI50 | 1.99E−06 | 1.99E−06 | 2.09E−09 |
| | TGI | 5.29E−06 | 5.29E−06 | 1.28E−08 |
| | LC50 | 9.84E−06 | 9.84E−06 | 6.66E−07 |
| IGROV-ET | GI50 | 4.56E−07 | 6.86E−06 | 1.59E−07 |
| | TGI | 1.90E−06 | 9.84E−06 | 6.54E−07 |
| | LC50 | 6.95E−06 | 9.84E−06 | 2.81E−06 |
| SK-BR-3 | GI50 | 3.74E−09 | 7.89E−07 | 1.83E−09 |
| | TGI | 4.05E−08 | 3.39E−06 | 1.89E−08 |
| | LC50 | 9.73E−06 | 9.84E−06 | 4.65E−06 |
| MEL-28 | GI50 | 1.66E−08 | 1.50E−06 | 4.14E−09 |
| | TGI | 8.24E−08 | 3.46E−06 | 1.52E−08 |
| | LC50 | 6.75E−07 | 8.00E−06 | 8.79E−08 |
| A-549 | GI50 | 5.15E−08 | 5.85E−06 | 6.96E−09 |
| | TGI | 3.51E−07 | 9.84E−06 | 4.86E−08 |
| | LC50 | 2.90E−06 | 9.84E−06 | 5.95E−07 |
| K-562 | GI50 | 7.80E−08 | 5.87E−06 | 2.00E−08 |
| | TGI | 3.03E−07 | 9.46E−06 | 4.73E−08 |
| | LC50 | 2.39E−06 | 9.84E−06 | 1.98E−07 |
| PANC-1 | GI50 | 3.49E−08 | 3.75E−06 | 6.24E−09 |
| | TGI | 8.82E−07 | 9.84E−06 | 9.00E−08 |
| | LC50 | 9.73E−06 | 9.84E−06 | 9.41E−06 |
| HT-29 | GI50 | 2.37E−08 | 4.22E−06 | 4.60E−09 |
| | TGI | 2.03E−07 | 9.84E−06 | 6.98E−08 |
| | LC50 | 9.73E−06 | 9.84E−06 | 5.58E−06 |
| LOVO | GI50 | 3.89E−08 | 3.55E−06 | 6.84E−09 |
| | TGI | 2.31E−07 | 9.84E−06 | 4.27E−08 |
| | LC50 | 3.66E−06 | 9.84E−06 | 2.49E−06 |
| LOVO-DOX | GI50 | 2.39E−06 | 9.84E−06 | 4.29E−07 |
| | TGI | 8.40E−06 | 9.84E−06 | 2.33E−06 |
| | LC50 | 9.73E−06 | 9.84E−06 | 9.41E−06 |
| HELA | GI50 | 3.76E−09 | 1.18E−06 | 2.81E−09 |
| | TGI | 2.61E−08 | 3.60E−06 | 9.79E−09 |
| | LC50 | 3.68E−07 | 9.84E−06 | 5.49E−08 |
| HELA-APL | GI50 | 4.11E−07 | 9.84E−06 | 3.64E−08 |
| | TGI | 5.41E−06 | 9.84E−06 | 1.68E−07 |
| | LC50 | 9.73E−06 | 9.84E−06 | 2.28E−06 |

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:
1. A compound of Formula I:

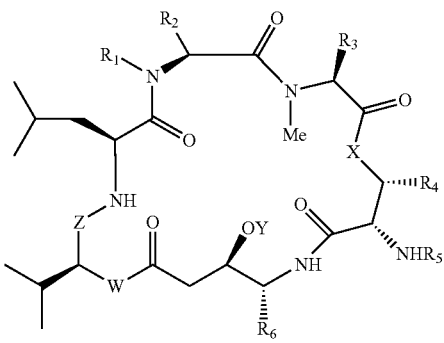

or a pharmaceutically acceptable salt thereof, wherein
$R^1$ and $R^2$ are independently H or $C_{1-4}$ alkyl, or $R^1$ and $R^2$ together form the alkyl ring of a proline or homoproline residue;
$R^3$ is selected from the group consisting of a side chain of an amino acid and a first fluorophore;
$R^4$ is H or $CH_3$;
$R^5$ is H, an amine protecting group, an amino acid residue, a polypeptide, a peptide which contains a second fluorophore, a chemical moiety bound to a solid support, or a moiety containing from about 1 to about 50 non-hydrogen atoms;
$R^6$ is an isoleucine side chain or a valine side chain;
W is O or NH;
X is O; and
Y is H or a hydroxyl protecting group;
Z is C(O) or C(O)—CH(CH$_3$)—C(O);
provided that when $R^1$ and $R^2$ together form the alkyl ring of a proline residue, then $R^4$ is H.

2. The compound according to claim 1 having the formula

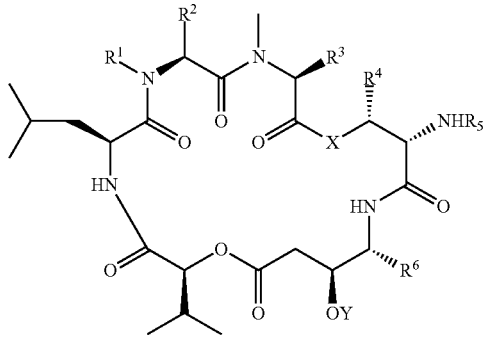

or a pharmaceutically acceptable salt thereof, wherein
$R^1$ and $R^2$ are independently H or $C_{1-4}$ alkyl, or $R^1$ and $R^2$ together form the alkyl ring of a proline residue;
$R^3$ is selected from the group consisting of a side chain of an amino acid and a first fluorophore;
$R^4$ is H or $CH_3$;
$R^5$ is H, an amine protecting group, an amino acid residue, a polypeptide, a peptide which contains a second fluorophore, a chemical moiety bound to a solid support, or a moiety containing from about 1 to about 50 non-hydrogen atoms;
$R^6$ is an isoleucine side chain or a valine side chain;
X is O; and
Y is H or a hydroxyl protecting group;

provided that when $R^1$ and $R^2$ together form the alkyl ring of a proline residue, then $R^4$ is H.
3. The compound according to claim 2, wherein $R^1$ is H and $R^2$ is methyl.
4. The compound according to claim 2, wherein $R^1$ and $R^2$ are methyl.
5. The compound according to claim 2, wherein $R^1$ and $R^2$ together form the alkyl ring of a proline residue.
6. The compound according to claim 2, wherein $R^3$ is a side chain of an amino acid.
7. The compound according to claim 2, wherein $R^3$ is naphtylmethyl.
8. The compound according to claim 2, wherein $R^3$ is a benzyl group optionally substituted with OH, OCH$_3$, CO(C$_6$H$_5$), F, Cl, Br, I, CH$_3$, or C$_2$H$_5$.
9. The compound according to claim 2, wherein $R^3$ contains a fluorophore.
10. The compound according to claim 2, wherein $R^4$ is CH$_3$.
11. The compound according to claim 2, wherein $R^4$ is H.
12. The compound according to claim 2, wherein $R^5$ is H.
13. The compound according to claim 2, wherein $R^5$ is an amine protecting group.
14. The compound according to claim 2, wherein $R^5$ is an amino acid residue or a polypeptide.
15. The compound according to claim 2, wherein $R^5$ contains a fluorophore.
16. The compound according to claim 2, wherein $R^5$ is selected from the group consisting of —(N-methyl)leucine;
  —(N-methyl)leucine-proline;
  —(N-CBz-N-methyl)leucine;
  —(N-methyl)leucine-proline-lactate;
  —(N-methyl)leucine-proline-pyruvate;
  —(N-methyl)leucine-proline-lactate-glutamine-pyroglutamate;
  —(N-methyl)leucine-proline-lactate-glutamine-cyclopentanoate;
  —(N-methyl)leucine-proline-lactate-leucine-pyroglutamate;
  —(N-methyl)leucine-proline-lactate-glutamine-cyclopentanoate;
  —(N-methyl)leucine-proline-alanine-leucine-pyroglutamate, and
  —(N-methyl)leucine-proline-(N-methyl)alanine-leucine-pyroglutamate.
17. The compound according to claim 2, wherein $R^6$ is a valine side chain.
18. The compound according to claim 2, wherein $R^6$ is a leucine side chain.
19. The compound according to claim 2, wherein Y is H.
20. The compound according to claim 2, wherein Y is a hydroxyl protecting group.
21. The compound according to claim 2, wherein $R^1$ and $R^2$ together form the alkyl ring of a proline residue; $R^3$ is a benzyl group optionally substituted with one or more selected from the group consisting of OH, OCH$_3$, CO(C$_6$H$_5$), F, Cl, Br, I, CH$_3$, and C$_2$H$_5$; $R^4$ is H; $R^6$ is a valine side chain; X is O; and Y is H.
22. The compound according to claim 2, wherein $R^1$ is H; $R^2$ is CH$_3$; $R^3$ is a benzyl group optionally substituted with one or more selected from the group consisting of OH, OCH$_3$, CO(C$_6$H$_5$), F, Cl, Br, I, CH$_3$, and C$_2$H$_5$; $R^4$ is CH$_3$; $R^5$ is as defined above; $R^6$ is a valine side chain; X is O; and Y is H.
23. The compound according to claim 2, wherein $R^1$ is CH$_3$; $R^2$ is CH$_3$; $R^3$ is a benzyl group optionally substituted with one or more selected from the group consisting of OH, OCH$_3$, CO(C$_6$H$_5$), F, Cl, Br, I, CH$_3$, and C$_2$H$_5$, preferably OCH$_3$; $R^4$ is CH$_3$; $R^6$ is a valine side chain; X is O; and Y is H.
24. The compound according to claim 2, wherein $R^5$ consists of 1-5 amino acid residues.

25. The compound according to claim 2, having the structure
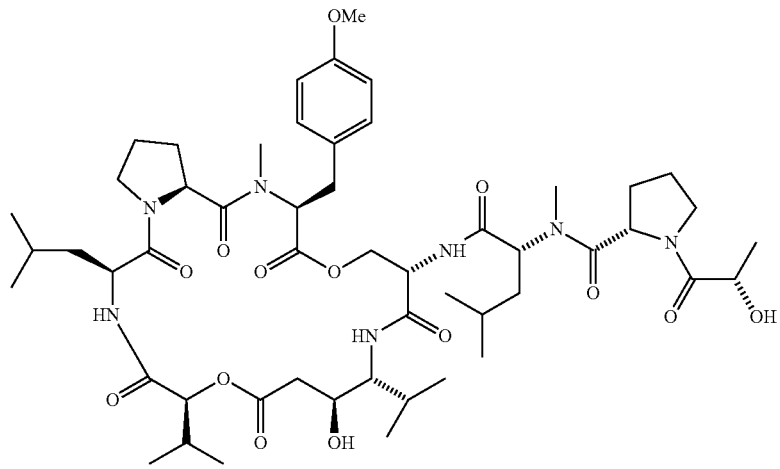
or a pharmaceutically acceptable salt thereof.
26. The compound according to claim 2, having the structure
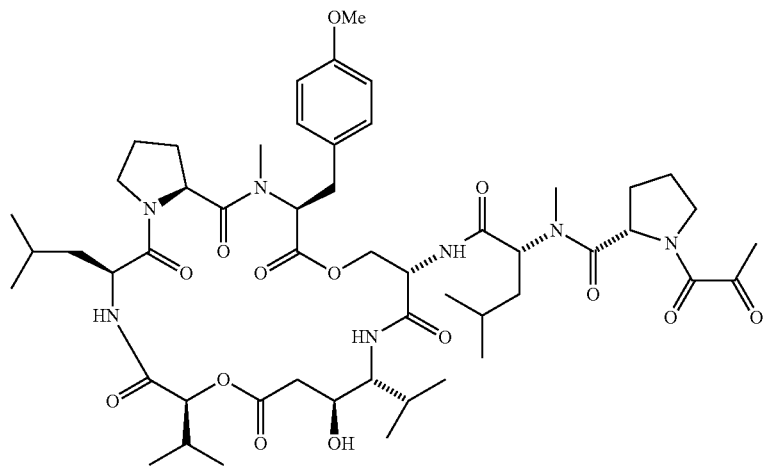
or a pharmaceutically acceptable salt thereof.
27. The compound according to claim 2, having the structure
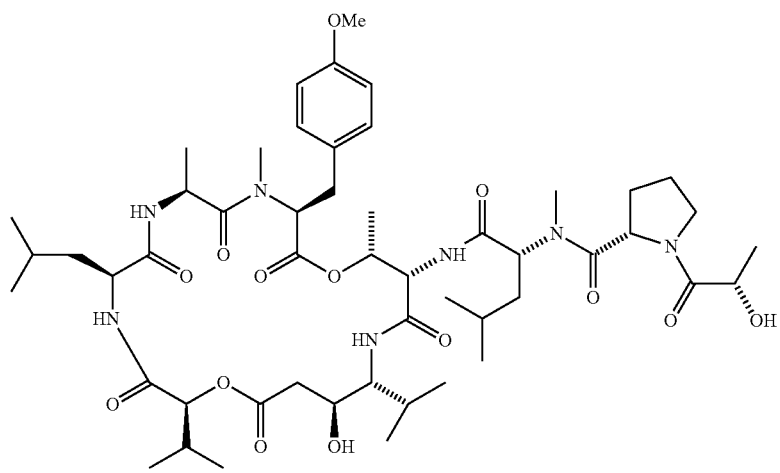
or a pharmaceutically acceptable salt thereof.

28. The compound according to claim 2, having the structure

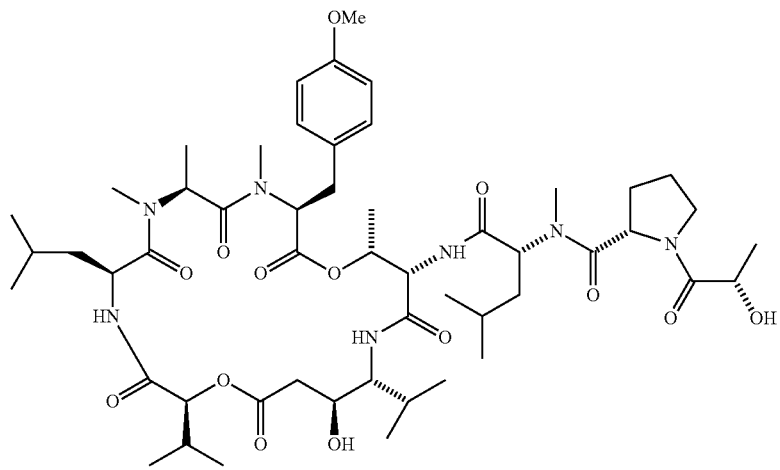

or a pharmaceutically acceptable salt thereof.

29. A composition comprising a compound according to claim 1 and a pharmaceutically compatible excipient or carrier.

30. A method of inhibiting, treating tumorigenesis, comprising contacting a cell with an effective amount of a compound according to claim 1.

31. A method of inhibiting the growth of a cancer cell, comprising contacting a cancer cell with an effective amount of a compound according to claim 1.

32. A method of inhibiting protein synthesis, comprising contacting a cell or cellular component with an effective amount of a compound of claim 1.

33. A method of enhancing apoptosis, comprising contacting a cell or cellular component with an effective amount of a compound according to claim 1.

34. A method of providing immunosuppresive therapy, comprising administering to a subject in need thereof an effective amount of a compound according to claim 1.

* * * * *